United States Patent [19]
Dominguez et al.

[11] Patent Number: 6,043,257
[45] Date of Patent: Mar. 28, 2000

[54] AMIDINOINDOLES, AMIDINOAZOLES, AND ANALOGS THEREOF

[75] Inventors: Celia Dominguez, Newark; Qi Han; Daniel Emmett Duffy, both of Wilmington; Jeongsook Maria Park, Bear; Mimi Lifen Quan, Newark; Karen Anita Rossi; Ruth Richmond Wexler, both of Wilmington, all of Del.

[73] Assignee: E. I. du Pont de Nemours and Company, Wilmington, Del.

[21] Appl. No.: 09/176,037

[22] Filed: Oct. 21, 1998

Related U.S. Application Data

[62] Division of application No. 08/916,736, Aug. 18, 1997, Pat. No. 5,886,191.

[51] Int. Cl.[7] .......................... A01N 43/40; A01N 43/38; C07D 401/12; C07D 235/26
[52] U.S. Cl. .................. 514/338; 546/275.7; 546/273.4; 546/273.7; 548/309.4; 548/362.5; 548/491; 548/484; 549/467; 549/58; 514/397; 514/399; 514/400
[58] Field of Search .................... 546/275.7; 514/338

[56] References Cited

U.S. PATENT DOCUMENTS 5,328,920  7/1994  Effland et al. ..................... 514/339

FOREIGN PATENT DOCUMENTS

| 0540051 | 5/1993 | European Pat. Off. . |
|---|---|---|
| 0655439 | 5/1995 | European Pat. Off. . |
| 06227971 | 8/1994 | Japan . |
| 9508540 | 3/1995 | WIPO . |
| 9627588 | 9/1996 | WIPO . |

OTHER PUBLICATIONS

Tidwell et al, *Journal of Medicinal Chemistry,* 1983, 26, 294–298, "Aromatic Amidines: Comparison of Their Ability to Block Respiratory Syncytial Virus Induced Cell Fusion and to Inhibit Plasmin, Urokinase, Thrombin, and Trypsin."

Fairley et al, *Journal of Medicinal Chemistry,* 1993, 36, 1746–1753, "Structure, DNA Minor Groove Binding, and Base Pair Specificity of Alkyl–and Aryl–Linked Bis (amidinobenzimidazoles) and Bis (amidinoindoles). "

Geratz et al, *Thrombosis Research,* 1981, 24, 73–83, "Inhibitory Effect of Amidino–Substituted Heterocyclic Compounds on The Amidase Activity of Plasmin and of High and Low Molecular Weight Urokinase and on Urokinase–Induced Plasminogen Activat ion. "

*Primary Examiner*—Johann Richter
*Assistant Examiner*—Dominic Keating
*Attorney, Agent, or Firm*—David H. Vance

[57] ABSTRACT

The present application describes amidinoindoles, amidinoazoles, and analogs thereof of formula I:

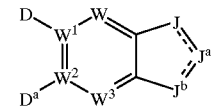

wherein W, $W^1$, $W^2$, and $W^3$ are selected from CH and N, provided that one of $W^1$ and $W^2$ is C(C(=NH)$NH_2$) and at most two of W, $W^1$, $W^2$, and $W^3$ are N and one of $J^a$ and $J^b$ is substituted by —$(CH_2)_n$—Z—A—B, which are useful as inhibitors of factor Xa or thrombin.

7 Claims, No Drawings

AMIDINOINDOLES, AMIDINOAZOLES, AND ANALOGS THEREOF

This application is a divisional of U.S. application Ser. No. 08/916,736 filed Aug. 18, 1997, now U.S. Pat. No. 5,886,191.

FIELD OF THE INVENTION

This invention relates generally to amidinoindoles, amidinoazoles, and analogs which are inhibitors of trypsin-like serine protease enzymes, especially thrombin and factor Xa, pharmaceutical compositions containing the same, and methods of using the same as anticoagulant agents for treatment and prevention of thromboembolic disorders.

BACKGROUND OF THE INVENTION

EP 0,540,051 and JP 06227971 describe a series of compounds useful as factor Xa inhibitors or to treat influenza based on the formula:

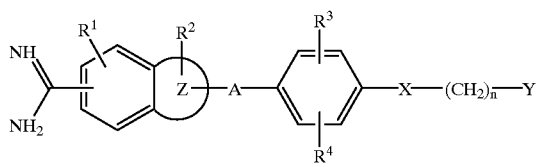

wherein A is an alkylene linker optionally substituted by hydroxyalkyl, carboxyl, alkoxycarbonyl, alkoxycarbonylalkyl, or carboxyalkyl, X is a bond, O, S, or carbonyl, n is 0–4, and Y is an optionally substituted carbocycle or heterocycle. The present invention does not involve compounds containing the above noted combination of A, X, n, and Y.

Tidwell et al, *Thrombosis Research* 1981, 24, 73–83, describe factor Xa inhibitory activity of a series of aromatic mono- and di-amidines. The amidino aromatic moieties are include indole, indoline, benzofuran and benzimidazole.

Tidwell et al, *J. Med. Chem.* 1983, 26, 294–298, report a series of amidinoindoles of the formula:

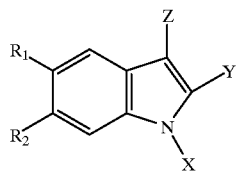

wherein one of $R^1$ and $R^2$ is amidine, X may be methyl or ethyl when Y and Z are H, Y may be $C(O)CH_2CH_3$ when X and Z are H, and Z may be CHO, $COCH_3$, $COCF_3$, or C(O)Ph when X and Y are H. Thrombin inhibition constants are given for these compounds.

EP 0,655,439 discuss IIb/IIIa antagonists of the formula:

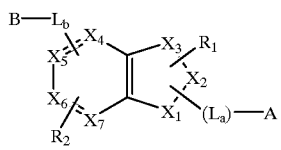

wherein the core ring is a heterocycle, B is a basic group, A is an acidic group, $R_1$ is an optional substituent, $R_2$ is an optional substituent, and $L_a$ and $L_b$ are linkers which may optionally be substituted. The present invention does not contain the $L_a$-A group.

Fairley et al, *J. Med. Chem.* 1993, 36, 1746–1753, illustrate a series of bis(amidinobenzimidazoles) and bis (amidinoindoles) of the formulae:

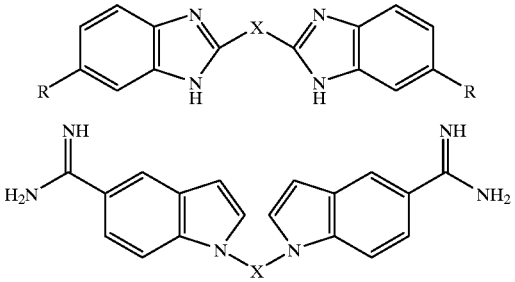

wherein R is an amidine or derivative thereof and X is an alkylene, alkenylene, phenylene or phenylenedimethylene linker. The DNA binding capabilities of these compounds were studied and reported, but inhibition of trypsin-like enzymes was not discussed.

WO 95/08540 depicts bis(amidinobenzimidazolyl) alkanes of the formula:

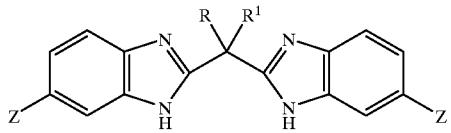

wherein Z is an amidine derivative and R and $R^1$ are selected from a variety of substituents including hydroxyl, amino, and alkoxy. These compounds are said to be useful in the treatment of viruses, specifically HIV. No mention is made of Xa or thrombin inhibition.

Trypsin-like enzymes are a group of proteases which hydrolyzed peptide bonds at basic residues liberating either a C-terminal arginyl or lysyl residue. Among these are enzymes of the blood coagulation and fibrinolytic system required for hemostasis. They are Factors II, X, VII, IX, XII, kallikrein, tissue plasminogen activators, urokinase-like plasminogen activator, and plasmin. Elevated levels of proteolysis by these proteases can result in disease states. For example, consumptive coagulopathy, a condition marked by a decrease in the blood levels of enzymes of both the coagulation system, the fibrinolytic system and accompanying protease inhibitors is often fatal. More specifically, proteolysis by thrombin is required for blood clotting. Inhibition of thrombin results in an effective inhibitor of blood clotting. The importance of an effective inhibitor of thrombin is underscored by the observation that conventional anticoagulants such as heparin (and its complex with the protein inhibitor, antithrombin III) are ineffective in blocking arterial thrombosis associated with myocardial infarctions and other clotting disorders. However, a low molecular weight thrombin inhibitor, containing a different functionality, was effective in blocking arterial thrombosis (Hanson and Harker, *Proc. Natl. Acad. Sci.* U.S.A. 85, 3184 (1988).

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: *Optimization of conditions for the catalytic effect of the factor IXa-factor VIII Complex: Probable role of the complex in the amplification of blood coagulation. Thromb. Res.* 1979, 15, 617–629), inhibition of factor Xa may be more efficient that inactivation of thrombin in interrupting the blood coagulation system.

Therefore, efficacious and specific inhibitors of factor Xa or thrombin are needed as potentially valuable therapeutic agents for the treatment of thromboembolic disorders. It is thus desirable to discover new thrombin or factor Xa inhibitors.

SUMMARY OF THE INVENTION

Accordingly, one object of the present invention is to provide novel amidinoindoles and analogs thereof which are useful as factor Xa or thrombin inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating thromboembolic disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of formula (I):

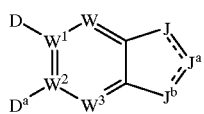

I or pharmaceutically acceptable salt or prodrug forms thereof, wherein D, $D^a$, J, $J^a$, $J^b$, W, $W^1$, $W^2$, and $W^3$, are defined below, are effective factor Xa or thrombin inhibitors.

DETAILED DESCRIPTION OF PREFERRED EMBODIMENTS

[1] Thus, in a first embodiment, the present invention provides a novel compound of formula I:

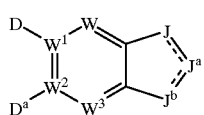

I or stereoisomer or pharmaceutically acceptable salt form thereof wherein:

W and $W^3$ are selected from CH and N;
$W^1$ and $W^2$ are selected from C, CH, and N;
provided that from 0–2 of W, $W^1$, $W^2$, and $W^3$ are N;
one of D and $D^a$ is selected from H, $C_{1-4}$ alkoxy, CN, $C(=NR^7)NR^8R^9$, $NHC(=NR^7)NR^8R^9$, $NR^8CH(=NR^7)$, $C(O)NR^8R^9$, and $(CH_2)_rNR^8R^9$, and the other is absent;

provided that if one of D and $D^a$ is H, then at least one of W, $W^1$, $W^2$, and $W^3$ is N;

one of $J^a$ and $J^b$ is substituted by $-(CH_2)_n-Z-A-B$;

J, $J^a$, and $J^b$ combine to form an aromatic heterocyclic system containing from 1–2 heteroatoms selected from the group consisting of N, O, and S substituted with 0–2 $R^1$, provided that $J^b$ can only be C or N;

J, $J^a$, and $J^b$ can, alternatively, combine to form a heterocyclic ring wherein $J^b$ is N and J and $J^a$ are $CH_2$ substituted with 0–1 $R^1$;

J, $J^a$, and $J^b$ can, alternatively, combine to form a heterocyclic ring wherein $J^b$ is CH, J is $NR^1$ and $J^a$ is $CH_2$ substituted with 0–1 $R^1$;

$R^1$ is selected from H, $C_{1-4}$ alkyl, $(CH_2)_rOR^3$, $(CH_2)_rNR^3R^{3'}$, $(CH_2)_rC(=O)R^2$, $(CH_2)_r(CH=CH)(CH_2)_rC(=O)R^2$, $(CH_2)_rNR^3C(=O)R^2$, $(CH_2)_rSO_2R^4$, $(CH_2)_rNR^3SO_2R^4$, and $(CH_2)_r$-5-membered heterocyclic system having 1–4 heteroatoms selected from N, O, and S;

$R^2$ is selected from H, $OR^3$, $C_{1-4}$ alkyl, $NR^3R^{3'}$, $CF_3$, and $C_{3-10}$ carbocyclic residue substituted with 0–2 $R^6$;

$R^3$ and $R^{3'}$ are independently selected from H, $C_{1-4}$ alkyl, and $C_{3-10}$ carbocyclic residue substituted with 0–2 $R^6$;

$R^4$ is selected from $C_{1-4}$ alkyl, $NR^3R^{3'}$, and $C_{3-10}$ carbocyclic residue substituted with 0–2 $R^6$;

Z is selected from CH=CH, $CH((CH_2)_mQ(CH_2)_mR^5)$, $CH((CH_2)_mQ(CH_2)_mR^5)C(O)NR^3$, $CH((CH_2)_mC(O)(CH_2)_mR^{5a})$, $N((CH_2)_qQ(CH_2)_mR^5)$, $N(Q'(CH_2)_mR^5)$, $C(O)N((CH_2)_mQ'(CH_2)_mR^{5a})$, $C(O)(CH_2)_r$, $C(O)O(CH_2)_r$, $OC(O)(CH_2)_r$, $C(O)(CH_2)_rNR^3(CH_2)_r$, $NR^3C(O)(CH_2)_r$, $OC(O)NR^3(CH_2)_r$, $NR^3C(O)O(CH_2)_r$, $NR^3C(O)NR^3(CH_2)_r$, $S(O)_p(CH_2)_r$, $SO_2CH_2$, $SCH_2C(O)NR^3$, $SO_2NR^3(CH_2)_r$, $NR^3SO_2(CH_2)_r$, and $NR^3SO_2NR^3(CH_2)_r$;

Q is selected from a bond, O, $NR^3$, C(O), $C(O)NR^3$, $NR^3C(O)$, $SO_2$, $NR^3SO_2$, and $SO_2NR^3$;

Q' is selected from a bond, C(O), $C(O)NR^3$, $SO_2$, and $SO_2NR^3$;

$R^5$ is selected from H, $C_{1-4}$ alkyl, $C_{3-10}$ carbocyclic residue substituted with 0–2 $R^6$, and 5–10 membered heterocyclic system containing from 1–3 heteroatoms selected from the group consisting of N, O, and S substituted with 0–2 $R^6$, provided that when Q is $SO_2$ or $NR^3SO_2$, $R^5$ is other than H and when Q' is $SO_2$, $R^5$ is other than H;

$R^{5a}$ is selected from $NHR_5$, $OR^5$, and $R^5$;

A is selected from:
  benzyl substituted with 0–2 $R^6$,
  phenethyl substituted with 0–2 $R^6$,
  phenyl-CH= substituted with 0–2 $R^6$,
  $C_{3-10}$ carbocyclic residue substituted with 0–2 $R^6$, and
  5–10 membered heterocyclic system containing from 1–3 heteroatoms selected from the group consisting of N, O, and S substituted with 0–2 $R^6$;

B is selected from:
  X—Y, $C_{3-6}$ alkyl, $NR^3R^{3'}$, $C(=NR^3)NR^3R^{3'}$, $NR^3C(=NR^3)NR^3R^{3'}$,
  benzyl substituted with 0–2 $R^6$, $C_{3-10}$ carbocyclic residue substituted with 0–2 $R^6$, and 5–10 membered heterocyclic system containing from 1–3 heteroatoms selected from the group consisting of N, O, and S substituted with 0–2 $R^6$;

A and B can, alternatively, combine to form a $C_{9-10}$ carbocyclic residue substituted with 0–2 $R^6$ or a 9–10 membered heterocyclic system containing from 1–3 heteroatoms selected from the group consisting of N, O, and S substituted with 0–2 $R^6$;

X is selected from $C_{1-4}$ alkylene, —C(O)—, —C(O)$CR^3R^{3'}$—, —$CR^3R^{3'}$C(O), —S(O)$_p$—, —S(O)$_p$$CR^3R^{3'}$—, —$CR^3R^{3'}$S(O)$_p$—, —S(O)$_2$$NR^3$—, —$NR^3$S(O)$_2$—, —C(O)$NR^3$—, —$NR^3$C(O)—, —$NR^3$—, —$NR^3CR^3R^{3'}$—, —$CR^3R^{3'}NR^3$—, O, —$CR^3R^{3'}$O—, and —$OCR^3R^{3'}$—;

Y is selected from:
$C_{3-10}$ carbocyclic residue substituted with 0–2 $R^6$, and 5–10 membered heterocyclic system containing from 1–3 heteroatoms selected from the group consisting of N, O, and S substituted with 0–2 $R^6$;

$R^6$ is selected from H, OH, $(CH_2)_nOR^3$, halo, $C_{1-4}$ alkyl, CN, $NO_2$, $(CH_2)_rNR^3R^{3'}$, $(CH_2)_rC(O)R^3$, $NR^3C(O)R^{3'}$, $NR^3C(O)NR^3R^{3'}$, CH(=NH)$NH_2$, NHC(=NH)$NH_2$, $SO_2NR^3R^{3'}$, $CONHSO_2R^4$, $NR^3SO_2NR^3R^{3'}$, $NR^3SO_2$—$C_{1-4}$ alkyl, and ($C_{1-4}$ alkyl)-tetrazolyl;

$R^7$ is selected from H, OH, $C_{1-6}$ alkyl, $C_{1-6}$ alkylcarbonyl, $C_{1-6}$ alkoxy, $C_{1-4}$ alkoxycarbonyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$ is selected from H, $C_{1-6}$ alkyl and $(CH_2)_n$-phenyl;
$R^9$ is selected from H, $C_{1-6}$ alkyl and $(CH_2)_n$-phenyl;
n is selected from 0, 1, 2, 3, and 4;
m is selected from 0, 1, and 2;
p is selected from 0, 1, and 2;
q is selected from 1 and 2; and,
r is selected from 0, 1, 2, 3, and 4;
provided that:
(a) Z is other than $CH_2$; and,
(b) if Z is $CH((CH_2)_mQ(CH_2)_mR^5)$ or $CH((CH_2)_mC(O)(CH_2)_mR^{5a})$, then B is other than X—Y, a $C_{3-10}$ carbocyclic residue or a 5–10 membered heterocyclic system.

[2] In a preferred embodiment, the present invention provides compounds of formula II:

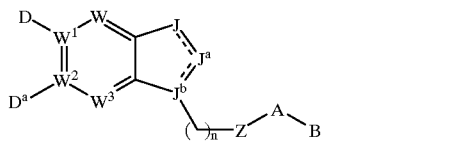

II wherein: from 0–1 of W, $W^1$, $W^2$, and $W^3$ are N;
$R^1$ is selected from H, $C_{1-4}$ alkyl, $(CH_2)_rOR^3$, $(CH_2)_rNR^3R^{3'}$, $(CH_2)_rC(=O)R^2$, $(CH_2)_rNR^3C(=O)R^2$, $(CH_2)_rSO_2R^4$, $(CH_2)_rNR^3SO_2R^4$, and $(CH_2)_r$-5-membered heterocyclic system having 1–4 heteroatoms selected from N, O, and S;
$R^2$ is selected from H, $OR^3$, $C_{1-4}$ alkyl, $NR^3R^{3'}$, and $CF_3$;
$R^3$ and $R^{3'}$ are independently selected from H, $C_{1-4}$ alkyl, and phenyl;

$R^4$ is selected from $C_{1-4}$ alkyl, phenyl and $NR^3R^{3'}$;
Z is selected from CH=CH, $CH((CH_2)_mQ(CH_2)_mR^5)$, $CH((CH_2)_mQ(CH_2)_mR^5)C(O)NR^3$, $CH((CH_2)_mC(O)(CH_2)_mR^{5a})$, $N((CH_2)_qQ(CH_2)_mR^5)$, $N(Q'(CH_2)_mR^5)$, $C(O)N((CH_2)_mQ'(CH_2)_mR^{5a})$, C(O), C(O) $CH_2$, C(O) O, OC(O), $C(O)(CH_2)_rNR^3(CH_2)_r$, $NR^3C(O)$, OC(O)$NR^3$, $NR^3C(O)O$, $NR^3C(O)NR^3$, $S(O)_p$, $SO_2CH_2$, $SO_2NR^3$, $NR^3SO_2$, and $NR^3SO_2NR^3$;

B is selected from:
X—Y, $C_{3-6}$ alkyl,
benzyl substituted with 0–2 $R^6$,
$C_{3-10}$ carbocyclic residue substituted with 0–2 $R^6$, and 5–10 membered heterocyclic system containing from 1–3 heteroatoms selected from the group consisting of N, O, and S substituted with 0–2 $R^6$;

A and B can, alternatively, combine to form a $C_{9-10}$ carbocyclic residue substituted with 0–2 $R^6$ or a 9–10 membered heterocyclic system containing from 1–3 heteroatoms selected from the group consisting of N, O, and S substituted with 0–2 $R^6$; and, $R^6$ is selected from H, OH, $(CH_2)_nOR^3$, halo, $C_{1-4}$ alkyl, CN, $NO_2$, $(CH_2)_rNR^3R^{3'}$, $(CH_2)_rC(O)R^3$, $NR^3C(O)R^{3'}$, $NR^3C(O)NR^3R^{3'}$, $SO_2NR^3R^{3'}$, $CONHSO_2R^4$, $NR^3SO_2NR^3R^{3'}$, $NR^3SO_2$—$C_{1-4}$ alkyl and ($C_{1-4}$ alkyl)-tetrazolyl.

[3] In a more preferred embodiment, the present invention provides compounds of formula II, wherein:
J, $J^a$, and $J^b$ combine to form an aromatic heterocyclic system containing from 1–2 nitrogen atoms, substituted with 0–1 $R^1$;
J, $J^a$, and $J^b$ can, alternatively, combine to form a heterocyclic ring wherein $J^b$ is N and J and $J^a$ are $CH_2$ substituted with 0–1 $R^1$;
J, $J^a$, and $J^b$ can, alternatively, combine to form a heterocyclic ring wherein $J^b$ is CH, J is $NR^1$ and $J^a$ is $CH_2$ substituted with 0–1 $R^1$;
$R^1$ is selected from H, $C_{1-4}$ alkyl, $(CH_2)_rOR^3$, $(CH_2)_rNR^3R^{3'}$, $(CH_2)_rC(=O)R^2$, $(CH_2)_rNR^3C(=O)R^2$, $(CH_2)_rSO_2R^4$, and $(CH_2)_rNR^3SO_2R^4$;
Z is selected from $CH((CH_2)_mQ(CH_2)_mR^5)$, $CH((CH_2)_mQ(CH_2)_mR^5)C(O)NR^3$, $CH((CH_2)_mC(O)(CH_2)_mR^{5a})$, $N((CH_2)_qQ(CH_2)_mR^5)$, $N(Q'(CH_2)_mR^5)$, $C(O)N((CH_2)_m Q'(CH_2)_mR^{5a})$, C(O), C(O) $CH_2$, $C(O)(CH_2)_rNR^3(CH_2)_r$, $NR^3C(O)$, $NR^3C(O)NR^3$, $S(O)_2$, $SO_2CH_2$, $SO_2NR^3$, $NR^3SO_2$, and $NR^3SO_2NR^3$;

A is selected from:
benzyl substituted with 0–2 $R^6$,
$C_{3-10}$ carbocyclic residue substituted with 0–2 $R^6$, and 5–10 membered heterocyclic system containing from 1–3 heteroatoms selected from the group consisting of N, O, and S substituted with 0–2 $R^6$;

B is selected from:
X—Y, $C_{3-6}$ alkyl,
benzyl substituted with 0–2 $R^6$,
$C_{5-6}$ carbocyclic residue substituted with 0–2 $R^6$, and 5–6 membered heterocyclic system containing from 1–3 heteroatoms selected from the group consisting of N, O, and S substituted with 0–2 $R^6$;

X is selected from —C(O)—, —C(O)$CR^3R^{3'}$—, —S(O)$_2$—, —S(O)$_p$$CR^3R^{3'}$—, —S(O)$_2NR^3$—, —C(O)$NR^3$—, —$NR^3$—, —$NR^3CR^3R^{3'}$—, and O;

Y is selected from:
$C_{5-6}$ carbocyclic residue substituted with 0–2 $R^6$, and 5–6 membered heterocyclic system containing from 1–3 heteroatoms selected from the group consisting of N, O, and S substituted with 0–2 $R^6$;

$R^6$ is selected from H, OH, $(CH_2)_nOR^3$, halo, $C_{1-4}$ alkyl, CN, $NO_2$, $(CH_2)_rN^3R^{3'}$, $(CH_2)_rC(O)R^3$, $NR^3C(O)R^{3'}$, $NR^3C(O)NR^3R^{3'}$, $SO_2NR^3R^{3'}$, $CONHSO_2R^4$, $NR^3SO_2NR^3R^{3'}$, $NR^3SO_2-C_{1-4}$ alkyl and $(C_{1-4}$ alkyl)-tetrazolyl;

n is selected from 0, 1, and 2; and, r is selected from 0, 1, and 2.

[4] In an even more preferred embodiment, the present invention provides compounds of formula II:

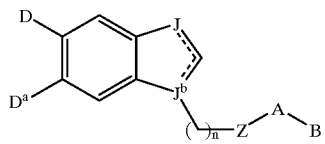

III wherein:

J and $J^b$ combine to form an aromatic heterocyclic system containing from 1–2 nitrogen atoms, substituted with 0–1 $R^1$;

J and $J^b$ can, alternatively, form a heterocyclic ring wherein $J^b$ is N and J is $CH_2$ substituted with 0–1 $R^1$;

J and $J^b$ can, alternatively, form a heterocyclic ring wherein $J^b$ is CH and J is $NR^1$;

Z is selected from $C(O)N(Q'R^{5a})$, $C(O)$, $C(O)NR^3$, $NR^3C(O)$, and $SO_2NR^3$;

Q' is selected from $C(O)$ and $C(O)NR^3$;

$R^5$ is selected from H and $C_{1-4}$ alkyl;

$R^{5a}$ is selected from $NHR^5$, $OR^5$, and $R^5$;

A is selected from:
 benzyl substituted with 0–1 $R^6$,
 phenyl substituted with 0–1 $R^6$,
 piperidinyl substituted with 0–1 $R^6$,
 piperazinyl substituted with 0–1 $R^6$, and
 pyridyl substituted with 0–1 $R^6$;

B is selected from:
 X—Y,
 benzyl substituted with 0–1 $R^6$,
 phenyl substituted with 0–2 $R^6$,
 cyclohexyl substituted with 0–1 $R^6$, and
 pyridyl substituted with 0–1 $R^6$;

X is selected from: —C(O)—, —S(O)$_2$—, SO$_2$CH$_2$, —S(O)$_2$NR$^3$—, —NR$^3$— and —C(O)NR$^3$—;

Y is selected from:
 phenyl substituted with 0–2 $R^6$, and
 pyridyl substituted with 0–1 $R^6$;

$R^6$ is selected from H, OH, $(CH_2)_nOR^3$, halo, $C_{1-4}$ alkyl, CN, $NO_2$, $(CH_2)_rNR^3R^{3'}$, $(CH_2)_rC(O)R^3$, $NR^3C(O)R^{3'}$, $NR^3C(O)NR^3R^{3'}$, $SO_2NR^3R^{3'}$, $CONHSO_2R^4$, $NR^3SO_2NR^3R^{3'}$, $NR^3SO_2-C_{1-4}$ alkyl and $(C_{1-4}$ alkyl)-tetrazolyl;

n is selected from 0, 1, and 2.

[5] In a further preferred embodiment, the present invention provides compounds of formula IV:

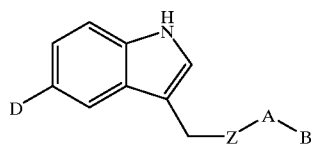

IV wherein A, B, D, and Z are as defined above.

[6] In a still further preferred embodiment, the present invention provides compounds selected from:

3-((4-cyclohexyl)phenylaminomethylcarbonyl)methyl-5-amidinoindole 3-(4-p-toluenesulfonyl-piperazinecarbonyl)methyl-5-amidinoindole 3-(4-(2-aminosulfonylphenyl)pyridine-2-aminocarbonyl)methyl-5-amidinoindole;

3-(4-[2-tetrazole]phenyl)phenylaminocarbonyl)methyl-5-amidinoindole;

3-(4-biphenylaminocarbonyl)methyl-5-amidinoindole;

3-(4-(phenylmethylsulfonyl)piperazinecarbonyl)methyl-5-amidinoindole;

3-(4-cyclohexylphenylaminocarbonyl)methyl-5-amidinoindole;

3-(4-benzylpiperazinecarbonyl)methyl-5-amidinoindole;

3-(3-amidinobenzylamino(methylcarbonylmethoxy)carbonyl)methyl-5-amidinoindole;

3-(4-(2-aminosulfonyl)phenyl)phenylaminocarbonylmethyl-5-amidinoindole;

3-(1-benzylpiperidine-4-aminocarbonyl)methyl-5-amidinoindole;

3-(4-phenylpiperazinecarbonyl)methyl-5-amidinoindole;

3-(4-benzylpiperidinecarbonyl)methyl-5-amidinoindole;

3-{2-bromo-4-(2-aminosulfonyl)phenylphenylaminocarbonyl)methyl-5-cyanoindole;

3-{2-methyl-4-(2-aminosulfonyl)phenylphenylaminocarbonyl)methyl-5-methylamino indole;

3-{2-fluoro-4-(2-aminosulfonyl)phenylphenylaminocarbonyl)methyl-5-amidnoindole;

3-{2-chloro-4-(2-aminosulfonyl)phenylphenylaminocarbonyl)methyl-5-cyanoindole;

3-{2-iodo-4-(2-aminosulfonyl)phenylphenylaminocarbonyl)methyl-5-cyanoindole;

3-{2-methyl-4-(2-aminosulfonyl)phenylphenylaminocarbonyl)methyl-5-amidinoindole;

3-{2-methyl-4-(2-(t-butylaminosulfonyl))phenylphenylaminocarbonyl)methyl-5-amidinoindole;

3-{4-(2-aminosulfonyl)phenyl)phenylaminocarbonylmethyl-α-(methylcarboxy methyl ether)-5-amidinoindole;

3-{4-(2-aminosulfonyl)phenyl)phenylaminocarbonylmethyl-α-(benzyl)-5-amidinoindole;

3-{4-(2-trifluoromethyl)phenyl)pyrid-2-ylaminocarbonylmethyl-5-amidinoindole;

3-{4-(2-ethylaminosulfonyl)phenyl)phenylaminocarbonylmethyl-5-amidinoindole;

3-{4-(2-propylaminosulfonyl)phenyl)phenyl}aminocarbonylmethyl-5-amidinoindole;

2-methyl-3-{2-iodo-4-(2-aminosulfonyl)phenyl)phenyl}aminocarbonylmethyl-5-amidinoindole;

2-methyl-3-{4-(2-aminosulfonyl)phenyl)phenyl}aminocarbonylmethyl-5-amidinoindole;

3-{4-(2-aminosulfonyl)phenyl)phenyl}-N-methylaminocarbonylmethyl-5-amidinoindole;

2-methyl-3-{4-(2-t-butylaminosulfonyl)phenyl)
  phenyl}aminocarbonylmethyl-5-methoxyindole; and,
3-{4-(2-N-methylaminosulfonyl)phenyl)phenyl}-N-
  methylaminocarbonylmethyl-5-amidinoindole;
or a stereoisomer or pharmaceutically acceptable salt form thereof.

[7] In another further preferred embodiment, the present invention provides compounds of formula IVa:

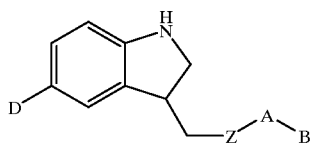

IVa wherein A, B, D, and Z are as defined above.

[8] In another still further preferred embodiment, the present invention provides compounds selected from:
3-{4-(2-(n-butylaminosulfonyl)
  phenylphenylaminocarbonyl)methyl-5-cyanoindoline;
3-{4-(2-(n-propylaminosulfonyl)
  phenylphenylaminocarbonyl)methyl-5-amidinoindoline;
(−)-3-{4-(2-aminosulfonyl)phenyl)pyrid-2-
  ylaminocarbonylmethyl-5-amidinoindoline;
3-{4-(2-aminosulfonyl)phenyl)pyrid-2-
  ylaminocarbonylmethyl-5-amidinoindoline;
3-{4-(2-dimethylaminosulfonyl)phenyl)
  phenylaminocarbonylmethyl-5-amidinoindoline;
(+)-3-{4-(2-t-butylaminosulfonyl)phenyl)pyrid-2-
  ylaminocarbonylmethyl-5-amidinoindoline;
(−)-3-{4-(2-t-butylaminosulfonyl)phenyl)pyrid-2-
  ylaminocarbonylmethyl-5-amidinoindoline;
3-{4-(2-aminosulfonyl)phenyl)pyrid-2-yl)
  aminocarbonylmethyl-5-aminocarboxyindoline;
3-{4-(2-t-butylaminosulfonyl)phenyl)
  phenyl}aminocarbonylmethyl-5-amidinoindoline; and,
3-{4-(2-t-butylaminosulfonyl)phenyl)pyrid-2-
  yl}aminocarbonylmethyl-5-amidinoindoline;
or a stereoisomer or pharmaceutically acceptable salt form thereof.

[9] In another further preferred embodiment, the present invention provides compounds of formula IVb:

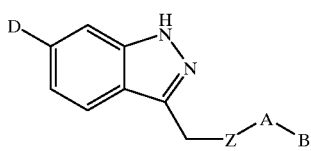

IVb wherein A, B, D, and Z are as defined above.

[10] In another still further preferred embodiment, the present invention provides compounds selected from:
3-{4-(2-aminosulfonyl)phenyl)pyrid-2-
  ylaminocarbonylmethyl-6-amidinoindazole;
3-{4-(2-aminosulfonyl)phenyl)phenyl
  aminocarbonylmethyl-6-amidinoindazole;
3-{4-(2-t-butyl aminosulfonyl)phenyl)pyrid-2-
  ylaminocarbonylmethyl-6-amidinoindazole; and,
3-{4-(2-t-butylaminosulfonyl)phenyl)phenyl
  aminocarbonylmethyl-6-amidinoindazole;
or a stereoisomer or pharmaceutically acceptable salt form thereof.

[11] In another further preferred embodiment, the present invention provides compounds of formula IVc:

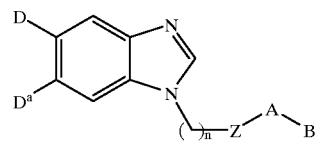

IVc wherein D, Da, Z, A, and B are as defined above.

[12] In another still further preferred embodiment, the present invention provides compounds selected from:
[4-(phenyl)phenylcarbonyl]methyl-6-
  amidinobenzimidazole;
[4-(phenyl)phenylcarbonyl]methyl-5-
  amidinobenzimidazole;
[4-(3-aminophenyl)phenylcarbonyl]methyl-6-
  amidinobenzimidazole;
[4-(3-aminophenyl)phenylcarbonyl]methyl-5-
  amidinobenzimidazole;
[4-(4-fluorophenyl)phenylcarbonyl]methyl-6-
  amidinobenzimidazole;
[4-(4-formylphenyl)phenylcarbonyl]methyl-6-
  amidinobenzimidazole;
[4-(2-aminosulfonylphenyl)phenylcarbonyl]methyl-6-
  amidinobenzimidazole;
[4-(2-tert-butylaminosulfonylphenyl)phenylcarbonyl]
  methyl-6-amidinobenzimidazole;
{4-[(2-tetrazolyl)phenyl]phenylcarbonyl}methyl-6-
  amidinobenzimidazole;
[4-(2-aminosulfonylphenyl)phenylaminocarbonyl]methyl-
  6-amidinobenzimidazole;
[4-(2-aminosulfonylphenyl)phenylaminocarbonyl]methyl-
  5-amidinobenzimidazole;
1-(4-benzylpiperidinecarbonyl)methyl-6-
  amidinobenzimidazole;
1-(4-benzylpiperidinecarbonyl)methyl-5-
  amidinobenzimidazole;
1-(4-benzylpiperidinecarbonyl)methyl-6-
  amidinobenzimidazole;
2-[4-(2-aminosulfonylphenyl)phenylcarbonyl]methyl-6-
  amidinobenzimidazole;
2-[4-(2-tert-butylaminosulfonylphenyl)phenylcarbonyl]
  methyl-5-azabenzimidazole;
2S-[4-(2-tert-aminosulfonylphenyl)phenylaminocarbonyl]
  methyl-thio-1H-imidazo(4,5-C) pyridine; and,
2S-[4-(2-aminosulfonylphenyl)phenylaminocarbonyl]
  methyl-thio-1H-imidazo(4,5-C) pyridine;
or a stereoisomer or pharmaceutically acceptable salt form thereof.

[13] In a preferred embodiment, the present invention provides compounds of formula V:

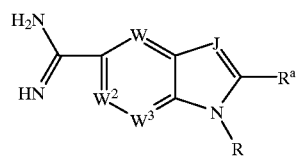

V wherein one of R and $R^a$ is —$(CH_2)_n$—Z—A—B and the other H;
 W, $W^2$, and $W^3$ are selected from CH and N, provided that at most one of W, $W^2$, and $W^3$ can be N;
 J is selected from N and C—$R^1$;

R¹ is selected from H, O, (CH$_2$)$_r$OR³, (CH$_2$)$_r$C(=O)R², (CH=CH)C(=O)R², (CH$_2$)$_r$NR³C(=O)R², (CH$_2$)$_r$SO$_2$R⁴, (CH$_2$)$_r$NR³SO$_2$R⁴, and (CH$_2$)$_r$-5-membered heterocyclic system having 1–4 heteroatoms selected from N, O, and S;

R² is selected from H, OR³, C$_{1-4}$ alkyl, NR³R³', CF$_3$, and C$_{3-10}$ carbocyclic residue substituted with 0–2 R⁶;

R³ and R³' are independently selected from H, C$_{1-4}$ alkyl, and C$_{3-10}$ carbocyclic residue substituted with 0–2 R⁶;

R⁴ is selected from OR³, C$_{1-4}$ alkyl, NR³R³', and C$_{3-10}$ carbocyclic residue substituted with 0–2 R⁶;

Z is selected from CH=CH, CH(CH$_2$)$_m$Q(CH$_2$)$_m$R⁵, CH((CH$_2$)$_m$Q(CH$_2$)$_m$R⁵)C(O)NR³, CH(CH$_2$)$_m$C(O)(CH$_2$)$_m$R$^{5a}$, N(CH$_2$)$_q$Q(CH$_2$)$_m$R⁵, NQ'(CH$_2$)$_m$R⁵, C(O)N((CH$_2$)$_m$Q'(CH$_2$)$_m$R$^{5a}$), C(O), C(O)CH$_2$, C(O)O, OC(O), C(O)NR³(CH$_2$)$_r$, NR³C(O), OC(O)NR³, NR³C(O)O, NR³C(O)NR³, S(O)$_p$, SO$_2$CH$_2$, SO$_2$NR³, NR³SO$_2$, and NR³SO$_2$NR³;

Q is selected from a bond, O, NR³, C(O), C(O)NR³, NR³C(O), SO$_2$, NR³SO$_2$, and SO$_2$NR³;

Q' is selected from a bond, C(O), C(O)NR³, SO$_2$, and SO$_2$NR³;

R⁵ is selected from H, C$_{1-4}$ alkyl, C$_{3-8}$ carbocyclic residue substituted with 0–2 R⁶, and 5–10 membered heterocyclic system containing from 1–3 heteroatoms selected from the group consisting of N, O, and S substituted with 0–2 R⁶, provided that when Q is SO$_2$ or NR³SO$_2$, R⁵ is other than H and when Q' is SO$_2$, R⁵ is other than H;

R$^{5a}$ is selected from NHR$_5$, OR⁵, and R⁵;

A is selected from:
  benzyl substituted with 0–2 R⁶,
  C$_{3-10}$ carbocyclic residue substituted with 0–2 R⁶, and
  5–10 membered heterocyclic system containing from 1–3 heteroatoms selected from the group consisting of N, O, and S substituted with 0–2 R⁶;

B is selected from:
  H, X—Y NR³R³', C(=NR³)NR³R³', NR³C(=NR³)NR³R³',
  benzyl substituted with 0–2 R⁶,
  C$_{3-10}$ carbocyclic residue substituted with 0–2 R⁶, and
  5–10 membered heterocyclic system containing from 1–3 heteroatoms selected from the group consisting of N, O, and S substituted with 0–2 R⁶;

X is selected from C$_{1-4}$ alkylene, —C(O)—, —C(O)CR³R³'—, —CR³R³'C(O), —S(O)$_p$—, —S(O)$_p$CR³R³'—, —CR³R³'S(O)$_p$—, —S(O)$_2$NR³—, —NR³S(O)$_2$—, —C(O)NR³—, —NR³C(O)—, —NR³—, —NR³CR³R³'—, —CR³R³'NR³—, O, —CR³R³'—, and —OCR³R³'—;

Y is selected from:
  C$_{3-10}$ carbocyclic residue substituted with 0–2 R⁶, and
  5–10 membered heterocyclic system containing from 1–3 heteroatoms selected from the group consisting of N, O, and S substituted with 0–2 R⁶;

R⁶ is selected from H, OH, (CH$_2$)$_n$OR³, halo, C$_{1-4}$ alkyl, CN, NO$_2$, (CH$_2$)$_r$NR³R³', (CH$_2$)$_r$C(O)R³, NR³C(O)R³', NR³C(O)NR³R³', CH(=NH)NH$_2$, NHC(=NH)NH$_2$, C(=O)R³, SO$_2$NR³R³', NR³SO$_2$NR³R³', and NR³SO$_2$—C$_{1-4}$ alkyl;

n is selected from 0, 1, 2, 3, and 4;
m is selected from 0, 1, and 2;
p is selected from 0, 1, and 2;
q is selected from 1 and 2; and,
r is selected from 0, 1, 2, 3, and 4.

[14] In another more preferred embodiment, the present invention provides compounds of formula VI:

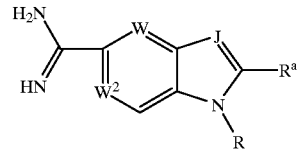

VI wherein one of R and R$^a$ is —(CH$_2$)$_n$—Z—A—B and the other H;

W and W² are selected from CH and N, provided that at most one of W and W² can be N;

J is selected from N and C—R¹;

R¹ is selected from H, (CH$_2$)$_r$OR³, (CH$_2$)$_r$C(=O)R², (CH$_2$)$_r$NR³C(=O)R², (CH=CH)C(=O)R², (CH$_2$)$_r$SO$_2$R⁴, and (CH$_2$)$_r$NR³ SO$_2$R⁴;

R² is selected from H, OR³, C$_{1-4}$ alkyl, NR³R³', and CF$_3$;

R³ and R³' are independently selected from H, C$_{1-4}$ alkyl, and phenyl;

R⁴ is selected from OR³, C$_{1-4}$ alkyl, NR³R³', and phenyl;

Z is selected from C(O), C(O)CH$_2$, C(O)NR³, NR³C(O), S(O)$_2$, SO$_2$CH$_2$, SO$_2$NR³, NR³SO$_2$, and NR³SO$_2$NR³;

A is selected from:
  C$_{3-10}$ carbocyclic residue substituted with 0–2 R⁶, and
  5–10 membered heterocyclic system containing from 1–3 heteroatoms selected from the group consisting of N, O, and S substituted with 0–2 R⁶;

B is selected from:
  X—Y,
  C$_{3-10}$ carbocyclic residue substituted with 0–2 R⁶, and
  5–10 membered heterocyclic system containing from 1–3 heteroatoms selected from the group consisting of N, O, and S substituted with 0–2 R⁶;

X is selected from —C(O)—, —C(O)CR³R³'—, —CR³R³'C(O), —S(O)$_p$—, —S(O)$_p$CR³R³'—, —CR³R³'S(O)$_p$—, —S(O)$_2$NR³—, —NR³S(O)$_2$—, —C(O)NR³—, —NR³—, —NR³CR³R³'—, and —CR³R³'NR³—;

Y is selected from:
  C$_{3-10}$ carbocyclic residue substituted with 0–2 R⁶, and
  5–10 membered heterocyclic system containing from 1–3 heteroatoms selected from the group consisting of N, O, and S substituted with 0–2 R⁶;

R⁶ is selected from H, OH, (CH$_2$)$_n$OR³, halo, C$_{1-4}$ alkyl, CN, NO$_2$, (CH$_2$)$_r$NR³R³', (CH$_2$)$_r$C(O)R³, NR³C(O)R³', NR³C(O)NR³R³', C(=O)R³, SO$_2$NR³R³', NR³SO$_2$NR³R³', and NR³SO$_2$—C$_{1-4}$ alkyl;

n is selected from 0, 1, 2, 3, and 4;
p is selected from 0, 1, and 2; and,
r is selected from 0, 1, 2, 3, and 4.

[15] In another even more preferred embodiment, the present invention provides compounds of formula VII:

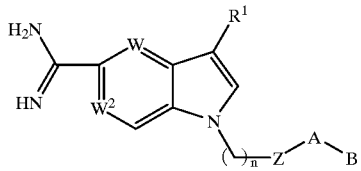

VII wherein, W and $W^2$ are selected from CH and N, provided that at most one of W and $W^2$ can be N;

$R^1$ is selected from H, $(CH_2)_rOR^3$, $(CH_2)_rC(=O)R^2$, $(CH_2)_rNR^3C(=O)R^2$, $(CH=CH)C(=O)R^2$, $(CH_2)_rSO_2R^4$, and $(CH_2)_rNR^3SO_2R^4$;

$R^2$ is selected from H, $OR^3$, $C_{1-4}$ alkyl, $NR^3R^{3'}$, and $CF_3$;

$R^3$ and $R^{3'}$ are independently selected from H, $C_{1-4}$ alkyl, and phenyl;

$R^4$ is selected from $OR^3$, $C_{1-4}$ alkyl, $NR^3R^{3'}$, and phenyl;

Z is selected from C(O), $C(O)CH_2$, $C(O)NR^3$, $S(O)_2$, $SO_2CH_2$, $SO_2NR^3$, and $NR^3SO_2NR^3$;

A is selected from:
$C_{3-10}$ carbocyclic residue substituted with 0–2 $R^6$, and 5–10 membered heterocyclic system containing from 1–3 heteroatoms selected from the group consisting of N, O, and S substituted with 0–2 $R^6$;

B is selected from:
X—Y,
$C_{3-10}$ carbocyclic residue substituted with 0–2 $R^6$, and 5–10 membered heterocyclic system containing from 1–3 heteroatoms selected from the group consisting of N, O, and S substituted with 0–2 $R^6$;

X is selected from $-S(O)_p-$, $-S(O)_pCR^3R^{3'}-$, $-CR^3R^{3'}S(O)_p-$, $-S(O)_2NR^3-$, $-NR^3S(O)_2-$, and $-C(O)NR^3-$;

Y is selected from:
$C_{3-10}$ carbocyclic residue substituted with 0–2 $R^6$, and 5–10 membered heterocyclic system containing from 1–3 heteroatoms selected from the group consisting of N, O, and S substituted with 0–2 $R^6$;

$R^6$ is selected from H, OH, $(CH_2)_nOR^3$, halo, $C_{1-4}$ alkyl, CN, $NO_2$, $(CH_2)_rNR^3R^{3'}$, $(CH_2)_rC(O)R^3$, $NR^3C(O)R^{3'}$, $NR^3C(O)NR^3R^{3'}$, $C(=O)R^3$, $SO_2NR^3R^{3'}$, $NR^3SO_2NR^3R^{3'}$, and $NR^3SO_2$–$C_{1-4}$ alkyl;

n is selected from 0, 1, 2, 3, and 4;

p is selected from 0, 1, and 2; and, r is selected from 0, 1, 2, 3, and 4.

[16] In another further preferred embodiment, the present invention provides compounds selected from:

1-(4-benzylpiperidinecarbonyl)methyl-5-amidinoindole;
1-(4-benzylpiperidinecarbonyl)ethyl-5-amidinoindole;
1-(4-(3-fluoro)benzylpiperidinecarbonyl)methyl-5-amidinoindole;
1-(1-(4-amidino)benzyl-N-(methylacetate)aminocarbonyl) methyl-5-amidinoindole;
methyl 1-(4-benzylpiperidinecarbonyl)methyl-5-amidinoindole-3-propanoate;
1-((4-benzylpiperidinecarbonyl)methyl-(3-ethanehydroxyl)-5-amidinoindole;
1-(4-benzylpiperidine-1-carbonyl)methyl-3-methylcarboxylic acid-5-amidinoindole;
1-(1-benzylpiperidine-4-aminocarbonyl)methyl-5-amidinoindole;
1-(4-benzoylpiperidinecarbonyl)methyl-5-amidinoindole;
1-(4-(3-fluoro)benzylpiperazinecarbonyl)methyl-5-amidinoindole;
1-(4-phenylbenzylaminocarbonyl)methyl-5-amidinoindole;
methyl 1-(4-benzylpiperidinecarbonyl)methyl-5-amidinoindole-3-propenoate; and,
1-(4-(2-fluoro)benzylpiperidinecarbonyl)methyl-5-amidinoindole;

or a stereoisomer or pharmaceutically acceptable salt form thereof.

In a second embodiment, the present invention provides novel pharmaceutical compositions, comprising: a pharmaceutically acceptable carrier and a therapeutically effective amount of a compound of formula (I) or a pharmaceutically acceptable salt or prodrug form thereof.

In a third embodiment, the present invention provides a novel method for treating or preventing a thromboembolic disorder, comprising: administering to a patient in need thereof a therapeutically effective amount of a compound of formula (I) or a pharmaceutically acceptable salt or prodrug form thereof.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

When any variable (e.g., $R^6$) occurs more than one time in any constituent or formula for a compound, its definition on each occurrence is independent of its definition at every other occurrence. Thus, for example, if a group is shown to be substituted with 0–2 $R^6$, then said group may optionally be substituted with up to two $R^6$ and $R^6$ at each occurrence is selected independently from the defined list of possible $R^6$. Also, combinations of substituents and/or variables are permissible only if such combinations result in stable compounds.

As used herein, "$C_{1-4}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, and t-butyl; "Alkenyl" is intended to include hydrocarbon chains of either a straight or branched configuration and one or more unsaturated carbon-carbon bonds which may occur in any stable point along the chain, such as ethenyl, propenyl, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "carbocycle" or "carbocyclic residue" is intended to mean any stable 3- to 7-membered monocyclic or bicyclic or 7- to 10-membered bicyclic or tricyclic, any of which may be saturated, partially unsaturated, or aromatic.

Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, [4.4.0]bicyclodecane (decalin), [2.2.2]bicyclooctane, phenyl, naphthyl, indanyl, adamantyl, or tetrahydronaphthyl (tetralin).

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another.

As used herein, the term "aromatic heterocyclic system" is intended to mean a stable 5- to 7-membered monocyclic or bicyclic or 7- to 10-membered bicyclic heterocyclic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiophenyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindolinyl, isoindolyl, isoquinolinyl (benzimidazolyl), isothiazolyl, isoxazolyl, morpholinyl, naphthyridinyl, octahydroisoquinolinyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, thianthrenyl, thiazolyl, thienyl, thienothiazole, thienooxazole, thienoimidazole, thiophenyl, triazinyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

When a bond to a substituent is shown to cross the bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The term "substituted", as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like. Preferred prodrugs are amidine prodrugs wherein either D or $D^a$ is $C(=NH)N(H)R^{10}$, and $R^{10}$ is selected from OH, $C_{1-4}$ alkoxy, $C_{6-10}$ aryloxy, $C_{1-4}$ alkoxycarbonyl, $C_{6-10}$ aryloxycarbonyl, $C_{6-10}$ arylmethylcarbonyl, $C_{1-4}$ alkylcarbonyloxy $C_{1-4}$ alkoxycarbonyl, and $C_{6-10}$ arylcarbonyloxy $C_{1-4}$ alkoxycarbonyl. More preferred prodrugs are where $R^7$ is OH, methoxy, ethoxy, benzyloxycarbonyl, methoxycarbonyl, and methylcarbonyloxymethoxycarbonyl.

"Stable compound" and "stable structure" are meant to indicate a compound that is sufficiently robust to survive isolation to a useful degree of purity from a reaction mixture, and formulation into an efficacious therapeutic agent.

SYNTHESIS

Compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those methods described below. Each of the references cited below are hereby incorporated herein by reference. All the temperatures are reported herein in degrees Celsius.

The compounds of Formula I can be prepared using the reactions and techniques described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis,* Wiley and Sons, 1991).

The following descriptions detail general methods of making benzimidazoles, indazoles and indoles through a variety of intermediates. These methods are not intended to represent all of the possible means of making the above compounds, merely a broad representation. One of ordinary skill in the art would readily understand what starting groups would be necessary to make all of the present compounds.

Intermediate 1 which can be formed via acylation of 4-amino-3-nitrobenzonitrile (Aldrich Chemical Co.) with an acyl chloride ($R^1$CHO) or an anhydride (($R^1$CO)$_2$O) in the presence of a base, followed by hydrogenation is shown below in Scheme 1. Reductive amination of an aldehyde (RCHO) in the presence of 1 using borane-pyridine in acetic acid can afford N-alkylated product 2. Alkylation of 1 with a halide ($P_3$X) in the presence of a base, such as $Cs_2CO_3$, can provide compound 3. Compounds 2 and 3 can be subjected to the Pinner reaction to give 6-amidino-benzimidazole derivative 4 and 5-amidino-benzimidazole derivative 5, respectively (see Khanna et al *J. Org. Chem.* 1995, 60, 960).

Scheme 1: Amidino-benzimidazoles via 4-amino-3-nitrobenzonitrile

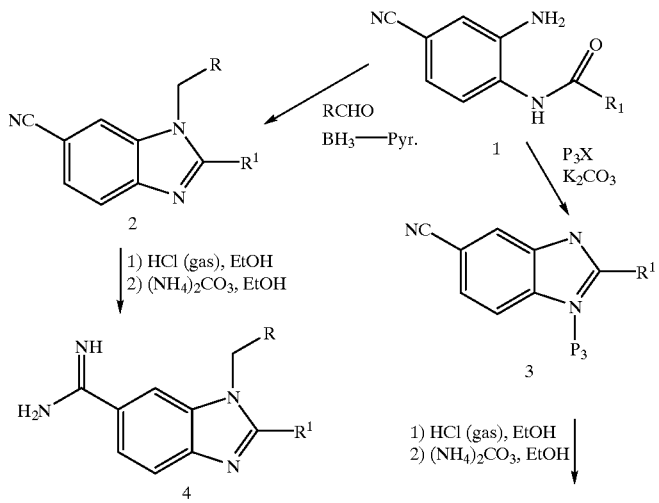

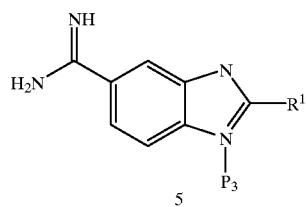

R = (CH$_2$)$_{n-1}$—Z—A—B
P$_3$ = (CH$_2$)$_n$—Z—A—B

Scheme 2 shows palladium (0) catalyzed coupling of 3-amino-4-nitrophenyl halides with zinc cyanide in DMF under reflux can provide compound 6 (see Lawton et al *J. Org. Chem.* 1959, 24, 26). Acylation of 6 with an acyl chloride or anhydride in the presence of base, followed by hydrogenation can form compound 7. Alkylation of 7 with a halide in the presence of a base, such as Cs$_2$CO$_3$, can provide compound 8. Reductive amination of an aldehyde with 7 using borane-pyridine in acetic acid can afford N-alkylated product 9. Compounds 8 and 9 can be converted to either their 6-amidino-benzimidazole or 5-amidino-benzimidazole derivatives, respectively via the Pinner reaction.

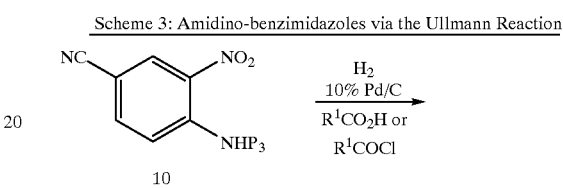

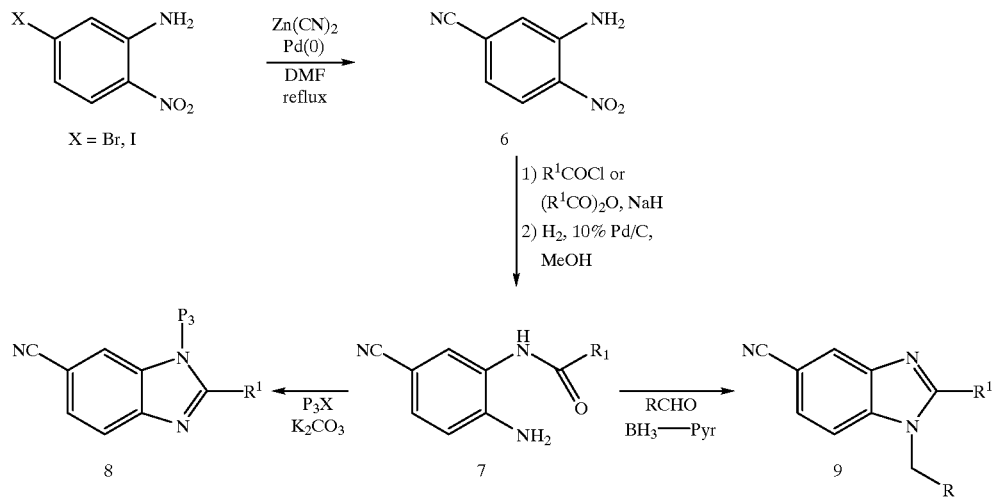

Ullmann reaction of 4-chloro-3-nitrobenzonitrile with an amine (P$_3$NH$_2$) in the presence of a base, such as NaHCO$_3$, can form compound 10 shown in Scheme 3. Hydrogenation of 10, followed by cyclization with an acid, such as formic acid, can give compound 5, which can be converted to its 5-amidino-benzimidazole derivatives as described above. In addition, compound 5 could be derivatized by addition of Br—(CH$_2$)$_n$—Z—A—B and the resulting mixture subjected to the Pinner reaction and separated by standard techniques.

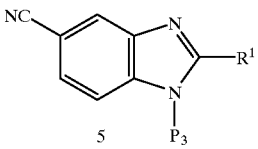

As described in Scheme 4, bromination of 4-aminobenzonitrile with NBS, followed by treatment with NaNO$_2$ and Cu$_2$O in conc. HCl can provide compound 11 (see Tsuji et al *Chem. Pharm. Bull.* 1992, 40, 2399). Ullmann reaction of 11 with an amine in the presence of a base, such as NaHCO$_3$, can form compound 12. Hydrogenation of 11, followed by cyclization with formic acid can give compound 8, which can be converted to its 6-amidino-benzimidazole derivative as described above.

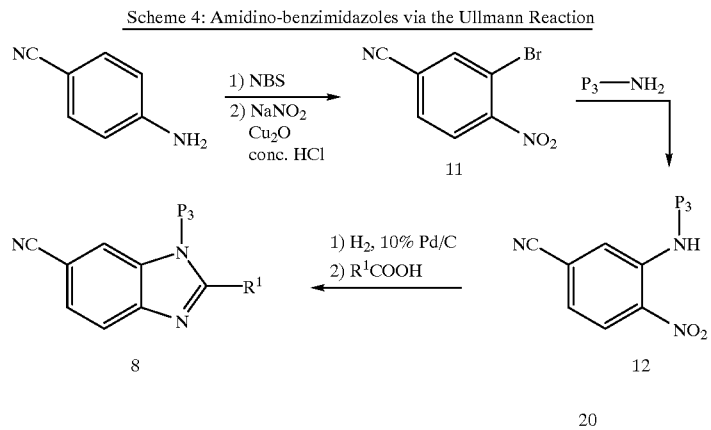

Scheme 5 details the synthesis of 2-substituted-amidino-benzimidazoles from 3,4-diamino-benzonitrile and 3-amino-4-hydroxybenzonitrile 13 which are obtained by hydrogenation of 4-amino-3-nitro-benzonitrile or 4-hydroxy-3-nitrobenzonitrile. Treatment of 13 with an acyl chloride or an acid in the presence of PPA can form compound 14 (see Walker et al *Synthesis* 1981, 303). Compound 14 can be converted to its amidino derivative via the Pinner reaction. Alternatively, when Y is NH, alkylation of 14 with a halide in the presence of a base, such as $K_2CO_3$, can afford a mixture of two regioisomers 15 and 16, which can, after being separated, be subjected to the Pinner reaction to give 2-substituted-6-amidino-benzimidazoles and 2-substituted-5-amidino-benzimidazole derivatives, respectively.

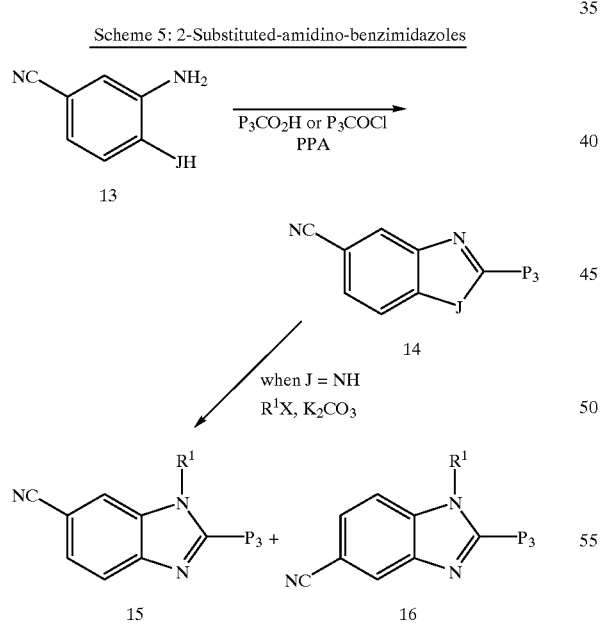

Protection of 6-hydroxy-indazole with pivalic anhydride in the presence of a base, followed by treatment with triflic anhydride can give compound 17 as shown in Scheme 6. Palladium (0) catalyzed coupling of 17 with zinc cyanide can provide compound 18. Deprotection of compound 18 under acidic conditions, followed by alkylation of with a halide in the presence of a base can yield compound 19, which can be converted to its 6-amidino-indazole derivative via the Pinner reaction.

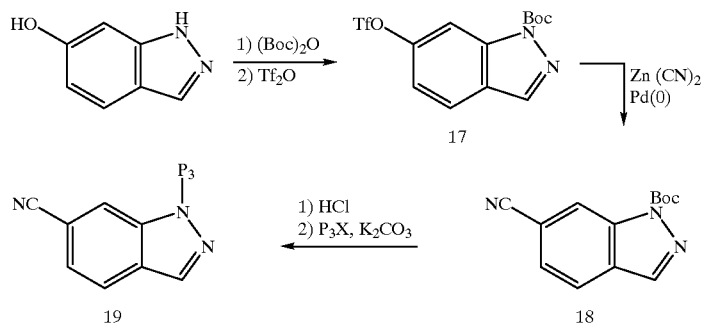

1-Substituted-amidino-indoles and -indazoles could be made from 5-cyanoindole as outlined below in Scheme 7. Intermediate 21 can easily be obtained via alkylation of 20 with Br(CH$_2$)$_n$Z. Peptide coupling with H—A—B using the BOP reagent or alkylation should afford intermediate 22 which is can then be converted to amidine 23 under Pinner conditions.

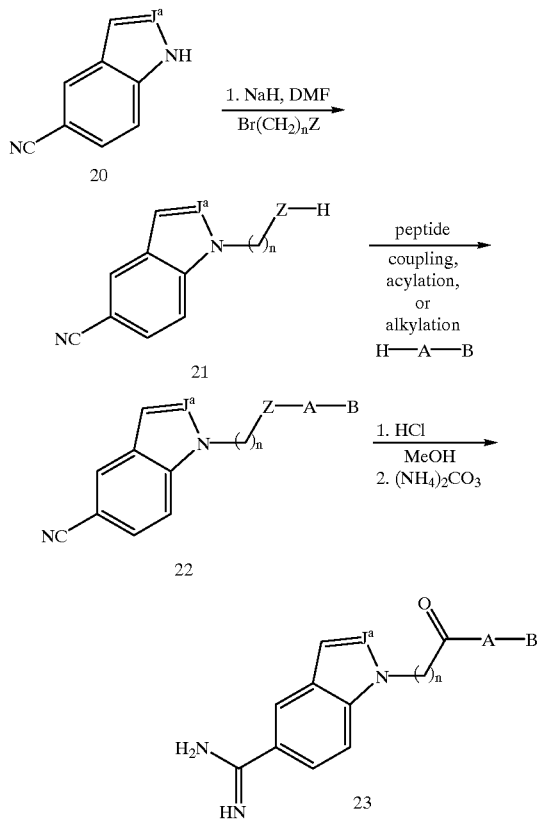

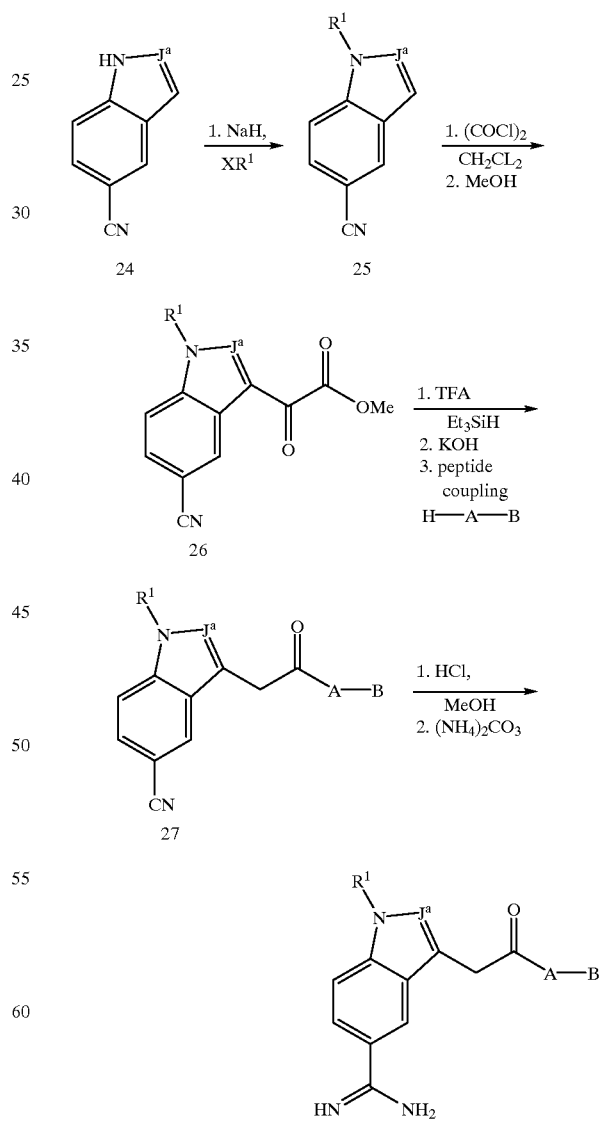

Scheme 8 shows 3-substituted-amidino-indoles and -indazoles are also derivable from 5-cyanoindole. Compound 26 may be obtained by substitution of R$^1$ on 24 to form 25 and acylation of 25 in the presence of oxalyl chloride at r.t. under nitrogen atmosphere. The compound can be subjected to selective ketone reduction with triethylsilane in trifluoroacetic acid for 3 h and then coupled with H—A—B.

The piperazine phenylsulfonamide, 31, and various other sulfonamide analogues can be prepared from commercially available BOC-piperazine via sulfonation with phenylsulfonyl chloride in CH$_2$Cl$_2$ and triethylamine as indicated in Scheme 9.

Compound 38 can be obtained via deprotection of the t-butyl group when R$^6$=SO$_2$NH—t—Bu, with TFA followed by alkylation or acylation with R$^3$X as outlined in Scheme 11.

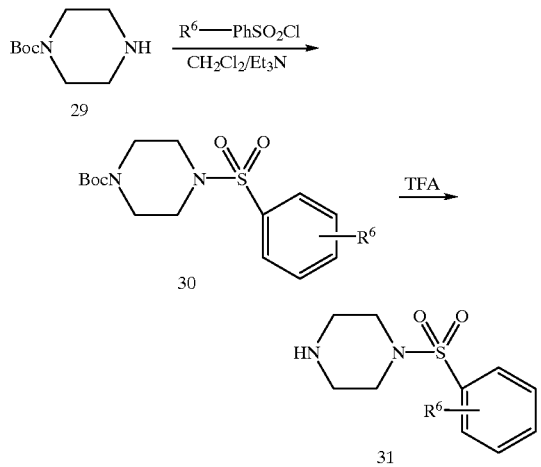

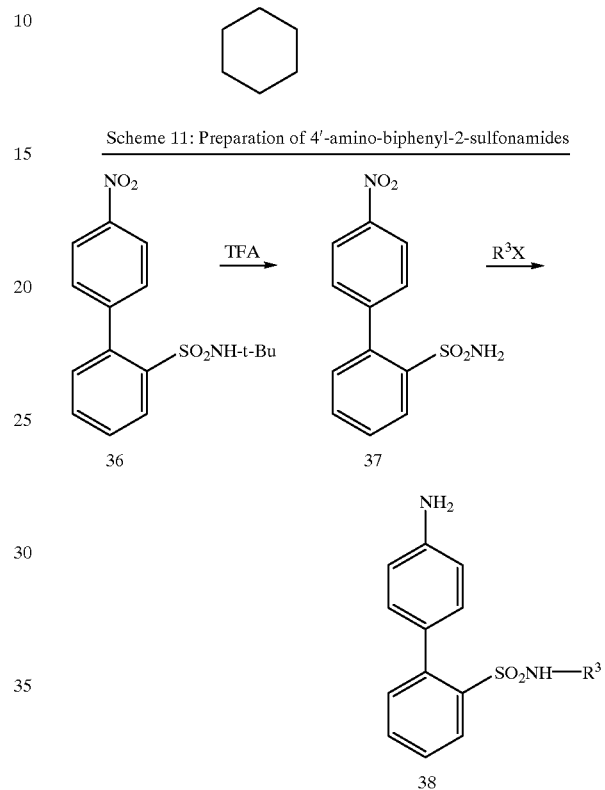

Biphenyl compounds may be prepared by procedures known to those of skill in the art. For example, Scheme 10 shows how to obtain substituted biphenyls via a Suzuki coupling with BOC protected 4-bromoaniline (or 1-bromo-4-nitrobenzene) to afford compound 35.

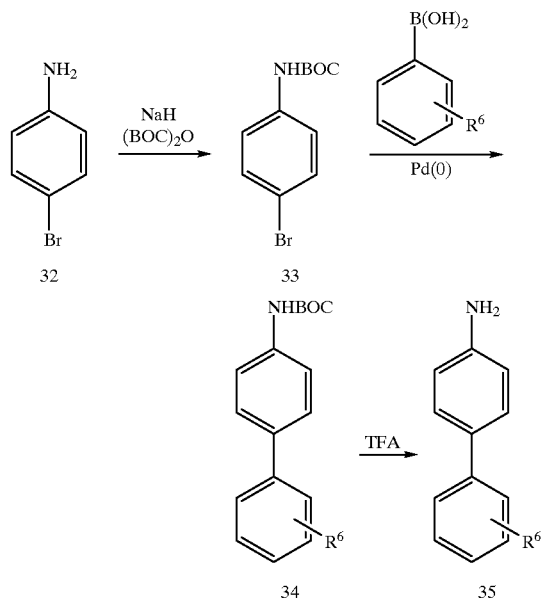

Scheme 12 shows how intermediates 43–45 may be obtained via the same intermediate 39. Acylation with oxalyl chloride followed by addition of methanol should yield ketoester 40 and selective reduction with triethyl silane may afford methyl acetate 42. Reduction with sodium borohydride can give the alcohol which then can be converted to 45 with R$^3$X. Intermediate 43 may be obtained via formylation with POCl$_3$ in DMF to yield aldehyde 41 which could then subjected to a Wittig olefination to afford compound 43.

Scheme 12: Addition of R¹ substituent to 1-substituted indoles or indazoles

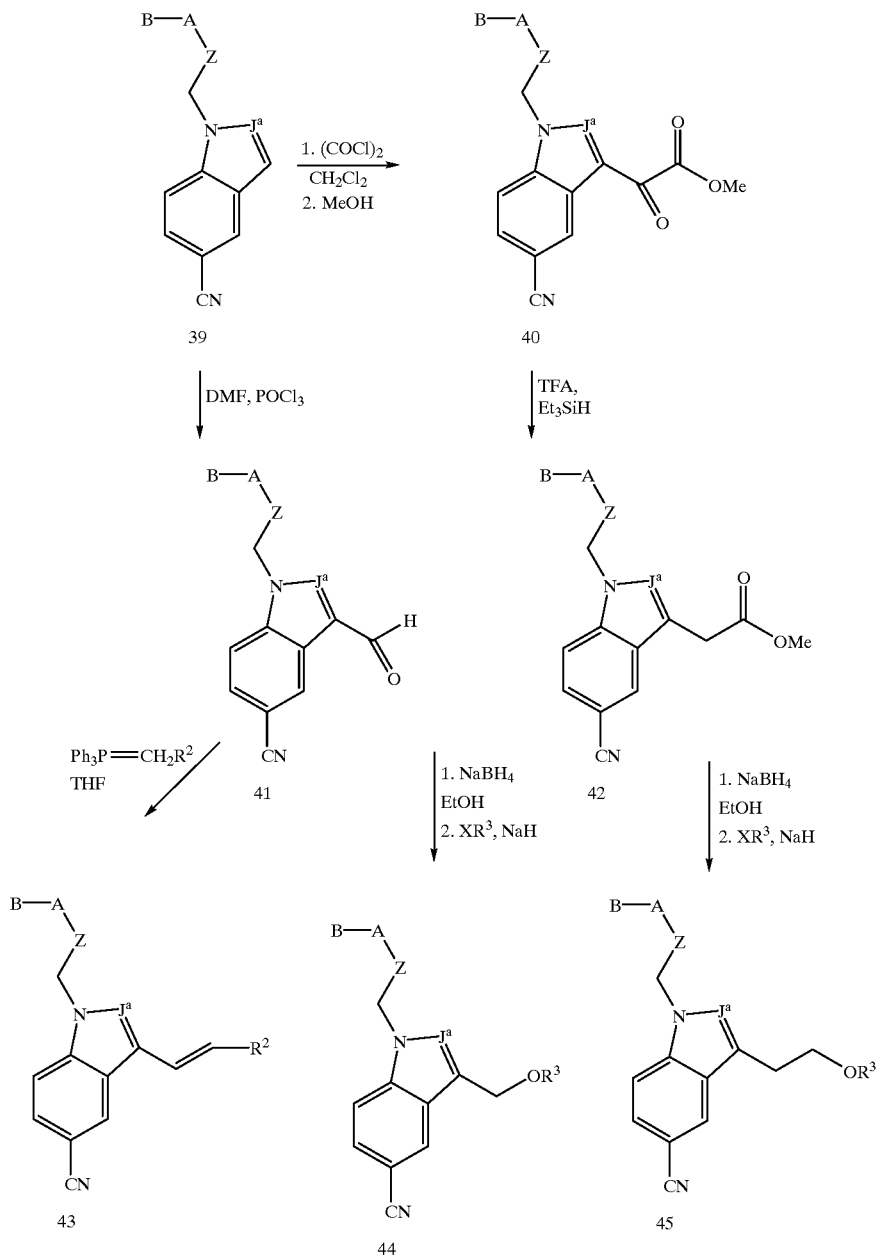

Sulfonyl chloride 49 may be obtained via aldehyde 47. The aldehyde can be reduced with sodium borohydride, sulfonated with methane sulfonyl chloride, and displaced with sodium sulfite in ethanol. Sulfonyl chloride 49 should then be obtained via chlorination with sulfonyl chloride as detailed in Scheme 13.

Scheme 13: Addition of R¹ to 1-protected indoles or indazoles

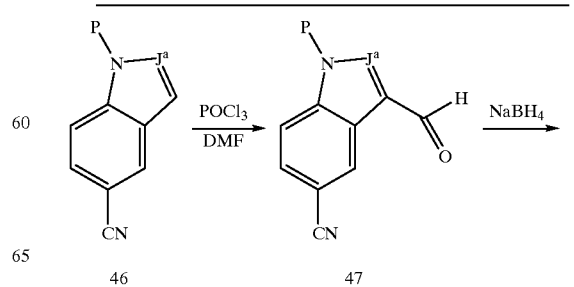

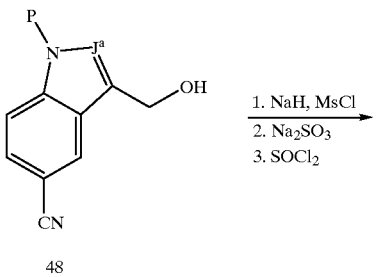

48

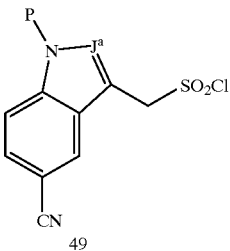

49

P is a protecting group e.g. MEM-group.

Scheme 14 details how substitution at the 2-position of the indole may be acomplished via lithiation with s-BuLi at −78° C. followed by addition of $R^1X$ to yield compound 51. Compound 51 can then converted to compound 52 by the previously mentioned methodology.

Scheme 14: Addition of two $R^1$'s to 1-protected indole

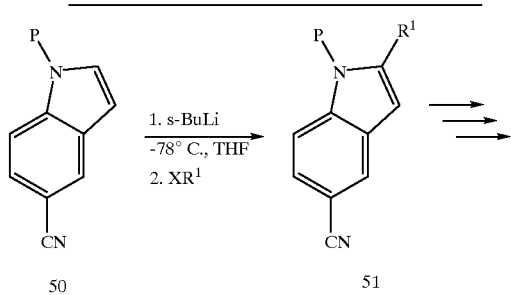

In Scheme 15, it is shown how the 5-cyanoindole compound 54 may be prepared via compound 53 by using sodium methoxide in the presence of nitromethane, followed by Zn reduction and condensation.

Scheme 15: Formation of indoles

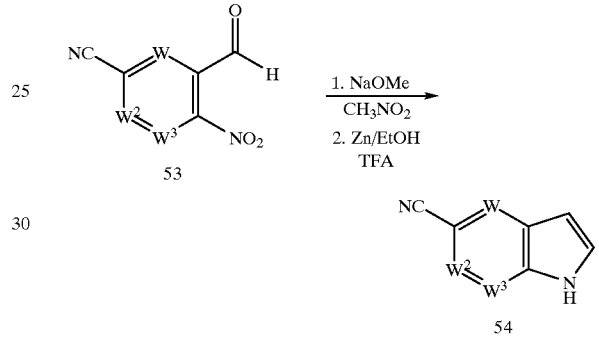

Groups A and B are available either through commercial sources, known in the literature or readily synthesized by the adaptation of standard procedures known to practioners skilled in the art of organic synthesis. The required reactive functional groups appended to analogs of A and B are also available either through commercial sources, known in the literature or readily synthesized by the adaptation of standard procedures known to practioners skilled in the art of organic synthesis. In the tables that follow the chemistry required to effect the coupling of A to B is outlined.

TABLE 1

Preparation of Amide, Ester, Urea, Sulfonamide and Sulfamide linkages between A and B.

| Rxn. No. | if A contains: | then the reactive substituent of Y is: | to give the following product A—X—Y: |
|---|---|---|---|
| 1 | A—$NHR^3$ as a substituent | ClC(O)—Y | A—$NR^3$—C(O)—Y |
| 2 | a secondary NH as part of a ring or chain | ClC(O)—Y | A—C(O)—Y |
| 3 | A—OH as a substituent | ClC(O)—Y | A—O—C(O)—Y |
| 4 | A—$NHR^3$ as a substituent | ClC(O)—$CR^3R^{3'}$—Y | A—$NR^3$—C(O)—$CR^3R^{3'}$—Y |
| 5 | a secondary NH as part of a ring or chain | ClC(O)—$CR^3R^{3'}$—Y | A—C(O)—$CR^3R^{3'}$—Y |
| 6 | A—OH as a | ClC(O)—$CR^3R^{3'}$—Y | A—O—C(O)—$CR^3R^{3'}$—Y |

TABLE 1-continued

Preparation of Amide, Ester, Urea, Sulfonamide and Sulfamide linkages between A and B.

| Rxn. No. | if A contains: | then the reactive substituent of Y is: | to give the following product A—X—Y: |
|---|---|---|---|
| 7 | A—$NHR^3$ as a substituent | $ClC(O)NR^3$—Y | A—$NR^3$—$C(O)NR^3$—Y |
| 8 | a secondary NH as part of a ring or chain | $ClC(O)NR^3$—Y | A—$C(O)NR^3$—Y |
| 9 | A—OH as a substituent | $ClC(O)NR^3$—Y | A—O—$C(O)NR^3$—Y |
| 10 | A—$NHR^3$ as a substituent | $ClSO_2$—Y | A—$NR^3$—$SO_2$—Y |
| 11 | a secondary NH as part of a ring or chain | $ClSO_2$—Y | A—$SO_2$—Y |
| 12 | A—$NHR^3$ as a substituent | $ClSO_2$—$CR^3R^{3'}$—Y | A—$NR^3$—$SO_2$—$CR^3R^{3'}$—Y |
| 13 | a secondary NH as part of a ring or chain | $ClSO_2$—$CR^3R^{3'}$—Y | A—$SO_2$—$CR^3R^{3'}$—Y |
| 14 | A—$NHR^3$ as a substituent | $ClSO_2$—$NR^3$—Y | A—$NR^3$—$SO_2$—$NR^3$—Y |
| 15 | a secondary NH as part of a ring or chain | $ClSO_2$—$NR^3$—Y | A—$SO_2$—$NR^3$—Y |
| 16 | A—C(O)Cl | HO—Y as a substituent | A—C(O)—O—Y |
| 17 | A—C(O)Cl | $NHR^3$—Y as a substituent | A—C(O)—$NR^3$—Y |
| 18 | A—C(O)Cl | a secondary NH as part of a ring or chain | A—C(O)—Y |
| 19 | A—$CR^3R^{3'}C(O)Cl$ | HO—Y as a substituent | A—$CR^3R^{3'}C(O)$—O—Y |
| 20 | A—$CR^3R^{3'}C(O)Cl$ | $NHR^3$—Y as a substituent | A—$CR^3R^{3'}C(O)$—$NR^3$—Y |
| 21 | A—$CR^3R^{3'}C(O)Cl$ | a secondary NH as part of a ring or chain | A—$C(R^3)_2C(O)$—Y |
| 22 | A—$SO_2Cl$ | $NHR^3$—Y as a substituent | A—$SO_2$—$NR^3$—Y |
| 23 | A—$SO_2Cl$ | a secondary NH as part of a ring or chain | A—$SO_2$—Y |
| 24 | A—$CR^3R^{3'}SO_2Cl$ | $NHR^3$—Y as a substituent | A—$CR^3R^{3'}SO_2$—$NR^3$—Y |
| 25 | A—$CR^3R^{3'}SO_2Cl$ | a secondary NH as part of a ring or chain | A—$CR^3R^{3'}SO_2$—Y |

The chemistry of Table 1 can be carried out in aprotic solvents such as a chlorocarbon, pyridine, benzene or toluene, at temperatures ranging from −20° C. to the reflux point of the solvent and with or without a trialkylamine base.

The coupling chemistry of Table 2 can be carried out by a variety of methods. The Grignard reagent required for Y is prepared from a halogen analog of Y in dry ether,

TABLE 2

Preparation of ketone linkages between A and B.

| Rxn. No. | if A contains: | then the reactive substituent of Y is: | to give the following product A—X—Y: |
|---|---|---|---|
| 1 | A—C(O)Cl | BrMg—Y | A—C(O)—Y |
| 2 | A—$CR^3R^{3'}C(O)Cl$ | BrMg—Y | A—$CR^3R^{3'}_2C(O)$—Y |
| 3 | A—C(O)Cl | $BrMgCR^3R^{3'}$—Y | A—$C(O)CR^3R^{3'}$—Y |
| 4 | A—$CR^3R^{3'}C(O)Cl$ | $BrMgCR^3R^{3'}$—Y | A—$CR^3R^{3'}C(O)CR^3R^{3'}$—Y | dimethoxyethane or tetrahydrofuran at 0° C. to the reflux point of the solvent. This Grignard reagent can be reacted directly under very controlled conditions, that is low temeprature (−20° C. or lower) and with a large excess of acid chloride or with catalytic or stoichiometric copper bromide.dimethyl sulfide complex in dimethyl sulfide as a solvent or with a variant thereof. Other methods available include transforming the Grignard reagent to the cadmium reagent and coupling according to the procedure of Carson and Prout (Org. Syn. Col. Vol. 3 (1955) 601) or a coupling mediated by Fe(acac)$_3$ according to Fiandanese et al. (Tetrahedron Lett., (1984) 4805), or a coupling mediated by manganese (II) catalysis (Cahiez and Laboue, Tetrahedron Lett., 33(31), (1992) 4437).

TABLE 3

Preparation of ether and thioether linkages between A and B

| Rxn. No. | if A contains : | then the reactive substituent of Y is : | to give the following product A—X—Y : |
|---|---|---|---|
| 1 | A—OH | Br—Y | A—O—Y |
| 2 | A—CR$^3$R$^{3'}$—OH | Br—Y | A—CR$^3$R$^{3'}$O—Y |
| 3 | A—OH | Br—CR$^3$R$^{3'}$—Y | A—OCR$^3$R$^{3'}$—Y |
| 4 | A—SH | Br—Y | A—S—Y |
| 5 | A—CR$^3$R$^{3'}$—SH | Br—Y | A—CR$^3$R$^{3'}$S—Y |
| 6 | A—SH | Br—CR$^3$R$^{3'}$—Y | A—SCR$^3$R$^{3'}$—Y |

The ether and thioether linkages of Table 3 can be prepared by reacting the two components in a polar aprotic solvent such as acetone, dimethylformamide or dimethylsulfoxide in the presence of a base such as potassium carbonate, sodium hydride or potassium t-butoxide at temperature ranging from ambient temperature to the reflux point of the solvent used.

TABLE 4

Preparation of —SO— and —SO2— linkages from thioethers of Table 3.

| Rxn. No. | if the starting material is : | and it is oxidized with Alumina (wet)/ Oxone (Greenhalgh, Synlett, (1992) 235) the product is : | and it is oxidized with m-chloroperbenzoic acid (Satoh et al., Chem. Lett. (1992) 381, the product is : |
|---|---|---|---|
| 1 | A—S—Y | A—S(O)—Y | A—SO$_2$—Y |
| 2 | A—CR$^3$R$^{3'}$S—Y | A—CR$^3$R$^{3'}$S(O)—Y | A—CR$^3$R$^{3'}$SO$_2$—Y |
| 3 | A—SCR$^3$R$^{3'}$—Y | A—S(O)CR$^3$R$^{3'}$—Y | A—SO$_2$CR$^3$R$^{3'}$—Y |

The thioethers of Table 3 serve as a convenient starting material for the preparation of the sulfoxide and sulfone analogs of Table 4. A combination of wet alumina and oxone provides a reliable reagent for the oxidation of the thioether to the sulfoxide while m-chloroperbenzoic acid oxidation will give the sulfone.

Other features of the invention will become apparent in the course of the following descriptions of exemplary embodiments which are given for illustration fo the invention and are not intended to be limiting thereof.

EXAMPLES

The synthesis of representative compounds according to the invention is described in further detail below with reference to the following specific, but non-limiting examples.

Abbreviations used in the Examples are defined as follows: "°C." for degrees Celsius, "d" for doublet, "dd" for doublet of doublets, "DAST" for diethylaminosulfur trifluoride, "eq" for equivalent or equivalents, "g" for gram or grams, "mg" for milligram or milligrams, "mL" for milliliter or milliliters, "H" for hydrogen or hydrogens, "hr" for hour or hours, "m" for multiplet, "M" for molar, "min" for minute or minutes, "MHz" for megahertz, "MS" for mass spectroscopy, "nmr" or "NMR" for nuclear magnetic resonance spectroscopy, "t" for triplet, "TLC" for thin layer chromatography.

Examples 1–15 were prepared by Michael addition of 5-cyano-benzimidazole to the α,β-unsaturated esters by using K$_2$CO$_3$ (2 mmol) as a base in DMF (10 mL) at 90–110° C. for 16–24 hours, followed by the Pinner reaction. A mixture of meta- and para-isomers was obtained by purification on TLC plates with 10–20% MeOH in CH$_2$Cl$_2$. The pure meta- or para-isomer was separated by HPLC.

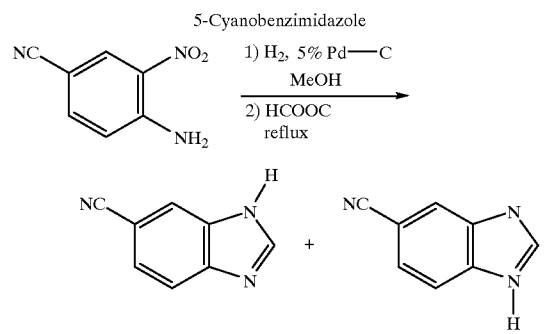

A solution of 4-amino-3-nitrobenzonitrile (20 mmol) in MeOH (300 mL) in the presence of 5% of Pd/C (1 g) was treated with hydrogen at room temperature for 16 hours. The reaction mixture was filtered and concentrated to give 3,4-diaminobenzonitrile (2.4 g, 90% of yield), which was directly treated with formic acid (20 mL) under reflux for 4 hours. After removal of the excess formic acid, the residue was dissolved in EtOAc, washed with 10% sodium bicarbonate and brine, and dried over MgSO$_4$. Concentration gave 5-cyanobenzimidazole (2.2 g, 85%). $^1$H NMR (CD$_3$OD) δ8.39 (s, 1H), 8.05 (s, 1H), 7.76 (d, J=8.4 Hz, 1H), 7.59 (dd, J=8.4 Hz, J=1.1 Hz, 1H); MS: 144 (M+H)$^+$.

Preparation of Ethyl 2-(3-cyanophenyl)ethacrylate and Ethyl 2-(4-cyanophenyl)ethacrylate To a stirred suspension of zinc powder (22 mmol) in THF (10 mL) was added 1,2-dibromoethylene (0.2 g) at room temperature and the mixture was stirred for 30 minutes. A solution of 3-cyanobenzylbromide or 4-cyanobenzylbromide (20 mmol) in THF (25 mL) was slowly added at a rate of one drop per five seconds at 5–10° C. The mixture was stirred for 3 hours, and then transferred into a solution of copper (I) cyanide (20 mmol) and lithium chloride (40 mmol) in THF (20 mL) at −78° C. The resulting mixture was warmed up and stirred at −20° C. for 20 minutes, and was then cooled to −78° C. After ethyl 2-(bromomethyl)acrylate (20 mmol) was slowly added, the mixture was stirred at −78° C. for 2 hours, and then warmed to room temperature overnight. Ether (100 mL) and aqueous saturated ammonium chloride (50 mL) were added to the mixture and the mixture filtered. The filtrate was washed with water and brine, and dried over MgSO$_4$. Concentration gave a residue, which was purified by column chromatography with gradient solvent system (CH$_2$Cl$_2$-EtOAc) to give ethyl 2-(3-cyanophenyl)ethacrylate (1.2 g, 26.2%) and ester ethyl 2-(4-cyanophenyl)ethacrylate (3.6 g, 78.6%).

For ethyl 2-(4-cyanophenyl)ethacrylate: $^1$H NMR (CDCl$_3$) δ7.58 (dd, J=8.4 Hz, J=1.8 Hz, 2H), 7.28 (d, J=8.4

Hz, 2H), 6.17 (d, J=1.1 Hz, 1H), 5.48 (dd, J=2.6 Hz, J=1.1 Hz, 1H), 4.22 (q, J=7.3 Hz, 2H), 2.86 (dd, J=8.6 Hz, J=7.1 Hz, 2H), 2.61 (dd, J=8.6 Hz, J=7.0 Hz, 2H), 1.32 (t, J=7.0 Hz, 3H); MS: 247 (M+NH$_4$)$^+$.

For ethyl 2-(3-cyanophenyl)ethacrylate: $^1$H NMR (CDCl$_3$) δ7.51–7.36 (m, 4H), 6.17 (s, 1H), 5.48 (d, J=1.1 Hz, 1H), 4.22 (q, J=7.3 Hz, 2H), 2.84 (dd, J=8.4 Hz, J=7.0 Hz, 2H), 2.61 (dd, J=8.4 Hz, J=7.0 Hz, 2H), 1.32 (t, J=7.0 Hz, 3H); $^{13}$C NMR (CDCl$_3$) δ166.80, 142.85, 139.41, 133.14, 132.05, 129.85, 129.17, 118.94, 112.43, 60.79, 34.50, 33.57, 14.22; MS 247 (M+NH$_4$)$^+$.

Preparation of Ethyl [3-(4-cyanophenyl)-2-bromomethyl] acrylate

To a solution of 4-cyanobenzylbromide (40 mmol) in xylene (40 mL) was added triphenylphosphine (40 mmol) and the resulting solution was heated at 110° C. for 2 hours. After removal of xylene, a white solid was obtained, which was dissolved in a mixture of THF (40 mL) and EtOH (40 mL), treated with DBU (40 mmol) at room temperature for one hour, and then to it was added ethyl pyruvate (40 mmol). The resulting mixture was stirred at room temperature overnight and filtrated to remove Ph$_3$PO. The filtrate was concentrated, dissolved in EtOAc, washed with 1 N HCl, water and brine, and dried over MgSO$_4$. Concentration gave a mixture of cis and trans olefins in almost quantitative yield. A solution of the olefins (5 mmol), NBS (5 mmol), and AIBN (0.25 mmol) in CCl$_4$ (200 mL) was refluxed under nitrogen for 16 hours, filtered, concentrated and purified by column chromatography with gradient solvent system (CH$_2$Cl$_2$-EtOAc) to give the title compound (1.25 g, 85%) as a white solid. $^1$H NMR (CDCl$_3$) δ7.71 (d, J=1.4 Hz, 1H), 7.68 (d, J=8.8 Hz, 2H), 7.58 (J=8.5 Hz, 2H), 4.29 (q, J=7.3 Hz, 2H), 4.23 (s, 2H), 1.32 (t, J=7.3 Hz, 3H).

Preparation of Ethyl 2-(4-benzyloxyphenyl)methacrylate

A mixture of 4-bromophenol (40 mmol), benzylbromide (40 mmol) and Na$_2$CO$_3$ in DMF (200 mL) was stirred at room temperature for 24 hours and was then poured into water. A solid was collected and was further recrystallized from hexane to give 4-benzyloxybenzene bromide in almost quantitative yield. A solution of the bromide in THF (100 mL) was treated with BuLi (44 mmol) at −78° C. over 30 minutes and then with a solution of ZnI$_2$ (40 mmol) in THF (40 mL) over 20 minutes. After the resulting mixture was warmed to room temperature over an hour, it was cooled to −78° C. and a solution of copper (I) cyanide (40 mmol) and lithium chloride (80 mmol) in THF (50 mL) was slowly added. The resulting mixture was warmed and stirred at −20° C. for 20 minutes, cooled to −78° C., and to it was added ethyl 2-(bromomethyl)acrylate (40 mmol). The resulting mixture was stirred at −78° C. for 2 hours and was then warmed to room temperature overnight. Ether and aqueous saturated ammonium chloride were added and filtered. The filtrate was washed with water and brine, and dried over MgSO$_4$. Concentration gave a residue, which was purified by column chromatography with gradient solvent system (CH$_2$Cl$_2$-EtOAc) to give the title compound (3.6 g, 30.4%): $^1$H NMP (CDCl$_3$) δ7.44–7.26 (m, 5H),7.12 (d, J=8.4 Hz, 2H), 6.91 (d, J=8.4 Hz, 2H), 6.20 (s, 1H), 5.92 (s, 1H), 5.07 (s, 2H), 4.18 (q, J=7.4 Hz, 2H), 3.57 (s, 2H), 1.27 (t, J=7.4 Hz, 3H); MS: 314 (M+NH$_4$)$^+$.

EXAMPLE 1

Preparation of Ethyl 2-(3-amidinophenyl)ethyl-3-(5-amidinobenzimidazole)propionate and Ethyl 2-(3-amidinophenyl)ethyl-3-(6-amidinobenzimidazole) propionate A mixture of 5-cyanobenzimidazole (2 mmol), ethyl 2-(3-cyanophenyl)ethacrylate (2 mmol) and K$_2$CO$_3$ (2 mmol) in DMF (10 mL) was heated at 90° C. under nitrogen for 16 hours. The mixture was diluted with EtOAc (150 mL), washed with 1 N HCl, water, and brine, and dried over MgSO$_4$. After filtration and concentration, a residue was purified by column chromatography with gradient solvent system (CH$_2$Cl$_2$-EtOAc) to give a mixture of ethyl 2-(3-cyanophenyl)ethyl-3-(6-cyanobenzimidazole)propionate and ethyl 2-(3-cyanophenyl)methyl-3-(5-cyanobenzimidazole)propionate (0.57 g, 76.4%) as a colorless oil. $^1$H NMR (CDCl$_3$) δ8.13–7.36 (m, 8H), 4.55 (dd, J=14.3 Hz, J=9.2 Hz, 1H), 4.28 (dd, J=14.3 Hz, J=5.5 Hz, 1H), 4.07 (q, J=7.0 Hz, 2H), 3.00–2.91 (m, 1H), 2.80–2.64 (m, 2H), 2.18–2.07 (m, 1H), 1.92–1.82 (m, 1H), 1.12 (t, J=7.0, 3H).

EXAMPLES 2 AND 3

Preparation of Ethyl 2-(3-amidinophenyl)ethyl-3-(5-amidinobenzimidazole)propionate and Ethyl 2-(3-amidinophenyl)ethyl-3-(6-amidinobenzimidazole) propionate The mixture of esters obtained in Example 1 was treated with HCl (gas) in anhydrous ethanol (10 mL) for 15 minutes at 0° C. and then stirred for 16 hours. After removal of excess HCl (gas) and ethanol, the residue was treated with (NH$_4$)$_2$CO$_3$ (5 equivalents) in anhydrous ethanol (10 mL) at room temperature for 24 hours. Concentration gave a residue, which was purified on TLC plates with 10% MeOH in CH$_2$Cl$_2$ to give a mixture of the title compounds (400 mg, 65.4%): mp 160–165° C.; ESMS: 204.2 (M+2H)$^{2+}$. The mixture was further separated by HPLC on chiral OJ column with CO$_2$/MeOH/TEA (80/20/0.1) to give Example 2, ethyl 2-(3-amidinophenyl)ethyl-3-(5-amidinobenzimidazole) propionate, and Example 3, ethyl 2-(3-amidinophenyl)ethyl-3-(6-amidinobenzimidazole)propionate.

Example 2: $^1$H NMR (CD$_3$OD) δ8.36 (s, 1H), 8.17 (s, 1H), 7.75–7.72 (m, 2H), 7.63 (bs, 2H), 7.50–7.48 (m, 2H), .4.66 (dd, J=9.5 Hz, J=14.3 Hz, 1H), 4.55 (dd, J=5.5 Hz, J=14.2 Hz, 1H), 4.02–3.92 (m, 2H), 3.14–3.08 (m, 1H), 2.81 (t, J=7.0 Hz, 2H), 2.19–1.93 (m, 2H), 1.04 (t, J=7.0 Hz, 3H); ESMS: 204.2 (M+2H)$^{2+}$.

Example 3: $^1$H NMR (CD$_3$OD) δ8.37 (s, 1H), 8.10 (s, 1H), 7.84 (d, J=8.4 Hz, 1H), 7.72 (d, J=8.4 Hz, 1H), 7.65–7.62 (m, 2H), 7.55–7.46 (m, 2H), 4.68 (dd, J=9.5 Hz, J=14.3 Hz, 1H), 4.56 (dd, J=5.5 Hz, J=14.2 Hz, 1H), 4.04–3.94 (m, 2H), 3.24–3.18 (m, 1H), 2.83 (t, J=7.0 Hz, 2H), 2.19–1.95 (m, 2H), 1.05 (t, J=7.0 Hz, 3H); ESMS: 204.2 (M+2H)$^{2+}$.

EXAMPLE 4

Preparation of Ethyl 2-(4-amidinophenyl)ethyl-3-(5-amidinobenzimidazole)propionate and Ethyl 2-(4-amidinophenyl)ethyl-3-(6-amidinobenzimidazole) propionate Example 4 was made using the same method as described for Example 1, except ethyl 2-(4-cyanophenyl)ethacrylate (2 mmol) was used (100 mg, 13% for two steps): mp 230° C. (Dec.); ESMS: 407 (M+H)$^+$; HRMS: 407.2200 (obs.), 407.2195 (calcd.) for C$_{22}$H$_{26}$N$_6$O$_2$. Example 4 was further separated to give Examples 5 and 6.

EXAMPLES 5 AND 6

Preparation of Ethyl 2-(4-amidinophenyl)ethyl-3-(5-amidinobenzimidazole)propionate and Ethyl 2-(4-amidinophenyl)ethyl-3-(6-amidinobenzimidazole) propionate The mixture of compounds obtained in Example 4 were further separated to give Examples 5 and 6.

Example 5, ethyl 2-(4-amidinophenyl)ethyl-3-(5-amidinobenzimidazole)propionate: $^1$H NMR (DMSO-d$_6$):

δ9.43–9.08 (m, 6H), 7.74–7.65 (m, 2H), 7.40–7.38 (m, 2H), 7.35–7.00 (m, 4H), 4.67–4.55 (m, 2H), 4.06 (bs, 2H), 3.48 (bs, 2H), 3.20 (bs, 1H), 2.70 (bs, 2H), 1.00 (bs, 3H); ESMS: 407 (M+H)$^+$.

Example 6, ethyl 2-(4-amidinophenyl)ethyl-3-(6-amidinobenzimidazole)propionate: $^1$H NMR (DMSO-d$_6$): δ9.23–9.12 (m, 6H), 8.41 (s, 1H), 8.21 (s, 1H), 7.84–7.82 (m, 1H), 7.74 (d, J=8.1 Hz, 2H), 7.41 (d, J=7.8 Hz, 2H), 7.24 (bs, 1H), 4.58–4.56 (m, 2H), 3.95–3.89 (m, 2H), 3.10–3.00 (m, 1H), 2.73–2.71 (m, 2H), 1.90–1.88 (m, 2H), 0.98–0.96 (m, 3H); ESMS: 407 (M+H)$^+$.

EXAMPLE 7
Preparation of Ethyl [3-(4-amidinophenyl)-2-(5-amidinobenzimidazole)methyl]acrylate A mixture of 5-cyanobenzimidazole (2 mmol), ethyl [3-(4-cyanophenyl)-2-bromomethyl]acrylate (2 mmol) and K$_2$CO$_3$ (2 mmol) in DMF (10 mL) was heated at 90° C. under nitrogen for 24 hours. The mixture was diluted with EtOAc (150 mL), washed with 1 N HCl, water, and brine, and dried over MgSO$_4$. After filtration and concentration, the residue was purified by column chromatography (CH$_2$Cl$_2$-EtOAc) to give ethyl [3-(4-cyanophenyl)-2-(5-cyanobenzimidazole)methyl]acrylate (0.401 g, 56.3%) as a colorless oil. $^1$H NMR (CDCl$_3$) δ8.10–8.00 (m, 4H), 7.83–7.77 (m,, 2H), 7.52–7.44 (m, 2H), 7.01–6.98 (m, 1H), 5.20 (s, 2H), 4.24 (q, J=7.3 Hz, 2H), 1.25 (t, J=7.3 Hz, 3H); MS: 357 (M+H)$^+$.

The Pinner reaction converted ethyl [3-(4-cyanophenyl)-2-(5-cyanobenzimidazole)methyl]acrylate (0.42 mmol) to the title compound (400 mg, 65.4%): $^1$H NMR (CD$_3$OD) δ8.19–8.12 (m, 2H), 7.92–7.88 (m, 3H), 7.74–7.69 (m, 4H), 4.22–4.19 (m, 2H), 1.24– 1.20 (m, 3H); ESMS: 196.2 (M+2H)$^{2+}$; HRMS: 391.1889 (obs.), 391.1882 (cal'd.).

EXAMPLE 8
Preparation of Ethyl 2-(4-amidinophenyl)methyl-3-(6-amidinobenzimidazole)propionate and Ethyl 2-(4-amidinophenyl)methyl-3-(5-amidinobenzimidazole)propionate Ethyl [3-(4-cyanophenyl)-2-(5-cyanobenzimidazole)methyl]acrylate was hydrogenated in MeOH in the presence of 10% palladium on active carbon to give ethyl 2-(4-cyanophenyl)methyl-3-(6-cyanobenzimidazole)propionate and ethyl 2-(4-cyanophenyl)methyl-3-(5-cyanobenzimidazole)propionate: $^1$H NMR (CDCl$_3$) δ8.24–8.02 (m, 2H), 7.87–7.50 (m,, 4H), 7.34–7.28 (m, 2H), 4.58–4.55 (m, 1H), 4.32–4.27 (m, 1H), 4.12–3.93 (m, 2H), 3.20–2.91 (m, 2H), 2.79–2.72 (m, 1H), 1.10–0.95 (m, 3H).

The mixture obtained (1.5 mmol) was subjected to the Pinner reaction to obtain the title compound (300 mg, 48%): $^1$H NMR (CD$_3$OD): δ8.63 (bs, 1H), 8.27–7.96 (m, 7H), 4.98–4.54 (m, 2H), 3.98–3.80 (m, 2H), 3.53–3.45 (m, 1H), 3.37–3.09 (m, 2H), 1.00–0.96 (m, 3H); ESMS: 197 (M+2H)$^{2+}$.

Examples 51–63 were prepared by Method A, B, or C. All compounds were finally purified by HPLC (CH$_3$CN/H$_2$/ 0.05% TFA).

Method A: Examples 51–59 were made by Suzuki coupling reactions of [(4-bromophenyl)carbonyl]methyl-6-cyanobenzimidazole or [(4-bromophenyl)carbonyl]methyl-5-cyanobenzimidazole with a variety of boronic acids by using Na$_2$CO$_3$ (2–4 equivalents) and Pd(PPh$_3$)$_4$ (5–10% mmol$^{-1}$) as catalyst in THF (80% in H$_2$O, 10 mL/mmol), followed by Pinner reactions.

A mixture of [(4-bromophenyl)carbonyl]methyl-6-cyanobenzimidazole and [(4-bromophenyl)carbonyl]methyl-5-cyanobenzimidazole was made in over 90% yield by alkylation of 5-cyano-benzimidazole (36 mmol) with 2,4'-dibromoacetophenone (36 mmol) by using NaH (48 mmol) as a base in THF (80 mL). The mixture were isolated by HPLC on chiralcel OJ column with MeOH/CO$_2$ (20/80) to give pure individual compounds.

[(4-Bromophenyl)carbonyl]methyl-6-cyanobenzimidazole: $^1$H NMR (CDCl$_3$) δ8.35 (s, 1H), 8.11 (dd, J=1.1 Hz, J=0.7 Hz, 1H), 8.08 (d, J=8.8 Hz, 2H), 7.81 (d, J=8.4 Hz, 2H), 7.56 (dd, J=8.4 Hz, J=1.8 Hz, 1H), 6.16 (s, 1H); ESMS: 340/342 (M+H)$^+$.

[(4-Bromophenyl)carbonyl]methyl-5-cyanobenzimidazole: $^1$H NMR (CDCl$_3$) δ8.31 (s, 1H), 8.13 (t, J=0.7 Hz, 1H), 8.07 (d, J=8.8 Hz, 2H), 7.81 (d, J=8.8 Hz, 2H), 7.75 (dd, J=8.4 Hz, J=0.7 Hz, 1H), 7.57 (dd, J=8.4 Hz, J=1.1 Hz, 1H), 6.15 (s, 1H); ESMS: 340/342 (M+H)$^+$.

EXAMPLE 51
Preparation of [4-(phenyl)phenylcarbonyl]methyl-6-amidinobenzimidazole MP: 155–157° C.; $^1$H NMR (CD$_3$OD) δ8.44 (s, 1H) 8.23 (d, J=8.4 Hz, 1H), 8.07 (d, J=1.1 Hz, 1H), 7.91 (d, J=8.8 Hz, 1H), 7.88 (dd, J=8.4, 2H), 7.72 (dd, J=8.4 Hz, J=1.1 Hz, 3H), 7.52–7.41 (m, 3H), 6.10 (s, 2H); MS: 355 (M+H)$^+$, HRMS: 355.1554 (obs.), 355.1:559 (calcd.); Anal.: (C$_{22}$H$_{18}$N$_4$O$_1$+ 0.9TFA+1.2HCl+0.5H$_2$O) C, H, N, F, Cl.

EXAMPLE 52
Preparation of [4-(phenyl)phenylcarbonyl]methyl-5-amidinobenzimidazole MP: 260–261° C.; $^1$H NMR (CD$_3$OD) δ8.41 (s, 1H), 8.22 (s, 1H), 8.20 (d, J=8.8 Hz, 2H), 7.87 (d, J=8.4 Hz, 2H), 7.73–7.70 (m, 4H), 7.51–7.41 (m, 3H), 6.10 (s, 2H); MS: 355.2 (M+H)$^+$; HRMS: 355.1538 (obs.), 355.1559 (calcd.); Anal.: (C$_{22}$H$_{18}$N$_4$O$_1$+1.5TFA+0.08HCl+1H$_2$O) C, H, N, Cl.

EXAMPLE 53
Preparation of [4-(3-aminophenyl)phenylcarbonyl]methyl-6-amidinobenzimidazole $^1$H NMR (DMSO-d$_6$) δ9.22 (s, 1.5 H), 9.04 (s, 1.5 H), 8.48 (s, 1H), 8.22 (d, J=1.4 Hz, 1H), 8.18 (d, J=8.3 Hz, 2H), 7.91 (d, J=8.5 Hz, 1H), 7.84 (d, J=8.5 Hz, 2H), 7.69 (dd, J=8.6 Hz, 1.7 Hz, 1H), 7.21 (t, J=1.8 Hz, 1H), 7.04 (s, 1H), 7.00 (d, J=8.4 Hz, 1H), 6.73 (d, J=8.1 Hz, 1H), 6.14 (s, 2H); $^{13}$C NMR (DMSO-d$_6$) δ192.4, 165.9, 148.6, 147.6, 146.7, 146.2, 139.3, 134.3, 132.9, 129.7, 128.8, 126.8, 121.8, 121.3, 119.7, 115.6, 115.1, 113.0, 111.8, 51.0; MS: 370 (M+H)$^+$; HRMS: 370.1664 (obs.), 370.1668 (calcd.)

EXAMPLE 54
Preparation of [4-(3-aminophenyl)phenylcarbonyl]methyl-5-amidinobenzimidazole $^1$H NMR (CD$_3$OD) δ8.48 (s, 1H), 8.32 (d, J=8.4 Hz, 2H), 7.87 (d, J=845 Hz, 2H), 7.74 (s, 2H), 7.62–7.56 (m, 2H), 7.53 (d , J=8.4 Hz, 2H), 7.25 (d, J=7.4 Hz, 1H), 6.12 (s, 2H); MS: 370 (M+H)$^+$, HRMS: 370.1664 (obs.), 370.1668 (calcd.)

EXAMPLE 55
Preparation of [4-(4-fluorophenyl)phenylcarbonyl]methyl-6-amidinobenzimidazole MP: 102–105° C.; $^1$H NMR (CD$_3$OD) δ8.54 (bs, 1H), 8.23 (d, J=8.8 Hz, 2H), 8.10 (bs, 1H), 7.92 (bs, 1H), 7.86 (d, J=8.4 Hz, 2H); $^{19}$F NMRδ–116.3, –77.65 (TFA); $^{13}$C NMR (CD$_3$OD) δ192.9, 168.6, 165.0, 163.5, 147.2, 137.1, 134.3, 130.3, 130.2, 130.1, 128.5, 124.7, 123.4, 120.8, 117.1, 116.9, 112.9, 52.5; MS: 373.2 [(M+H)$^+$; HRMS: 373.1481 (obs.), 373.1465 (calcd.); Anal.: (C$_{22}$H$_{17}$N$_4$O$_1$F$_1$+1.9TFA+ 0.1HCl+2H$_2$O) C, H, N, F, Cl.

EXAMPLE 56
Preparation of [4-(4-formylphenyl)phenylcarbonyl]methyl-6-amidinobenzimidazole MP: 125–128° C.; $^1$H NMR (CD$_3$OD) δ10.05 (s, 1H), 8.48 (s, 1H), 8.27 (d, J=8.4 Hz, 1H), 8.07 (bs, 1H), 8.05 (d, J=8.4 Hz, 2H), 7.97 (d, J=8.1 Hz, 2H), 7.95 (d, J=8.1 Hz, 2H), 7.93 (d, J=8.4 Hz, 2H), 7.73 (dd, J=8.4 Hz, J=1.8 Hz, 1H), 6.12 (s, 2H); $^{13}$C NMR (CD$_3$OD) δ192.99, 168.67, 147.86, 140.90, 140.15, 134.44, 130.10, 128.64, 128.57, 128.09, 124.63, 123.41, 120.75, 112.87, 104.26, 54.45; MS: 192.2 (M+2H)$^{2+}$; HRMS: 383.1531 (obs.), 383.1508 (calcd.).

EXAMPLE 57
Preparation of [4-(2-aminosulfonylphenyl)phenylcarbonyl]methyl-6-amidinobenzimidazole MP: 126–128° C.; $^1$H NMR (CD$_3$OD) δ8.55 (bs, 1H), 8.18 (d, J=8.4 Hz, 2H), 8.13 (dd, J=7.7 Hz, J=1.4 Hz, 1H), 8.09 (s, 1H), 7.94 (d, J=8.8 Hz, 1H), 7.71 (dd, J=8.4 Hz, J=1.4 Hz, 1H), 7.67 (d, J=7.8 Hz, 1H), 7.65 (d, J=8.1 Hz, 2H), 7.60 (dd, J=7.8 Hz, J=1.4 Hz, 1H), 7.36 (dd, J=7.3 Hz, J=1.4 Hz, 1H), 6.13 (s, 2H); MS: 217.7 (M+2H)$^{2+}$; HRMS: 434.1303 (obs.), 434.1287 (calcd.)

EXAMPLE 58
Preparation of [4-(2-tert-butylaminosulfonylphenyl)phenylcarbonyl]methyl-6-amidinobenzimidazole MP: 118–120° C.; $^1$H NMR (CD$_3$OD) δ8.60 (bs, 1H), 8.19 (d, J=8.4 Hz, 2H), 8.13 (dd, J=7.7 Hz, J=1.4 Hz, 1H), 8.09 (s, 1H), 7.95 (d, J=8.8 Hz, 1H), 7.76 (dd, J=8.4 Hz, J=1.4 Hz, 1H), 7.67 (d, J=8.4 Hz, 2H), 7.63 (dd, J=7.7 Hz, J=1.5 Hz, 1H), 7.60 (dd, J=7.7 Hz, J=1.4 Hz, 1H), 7.34 (dd, J=7.7 Hz, J=1.4 Hz, 1H), 6.14 (s, 2H), 1.09 (s, 9H); $^{13}$C NMR (CD$_3$OD) δ193.25, 168.78, 149.52, 147.86, 143.50, 140.87, 134.76, 133.27, 133.07, 132.83, 131.58, 130.45, 129.77, 129.49, 128.76, 127.34, 124.45, 123.22, 120.99, 112.68, 55.30, 52.38, 30.22; Anal.: (C$_{26}$H$_{27}$N$_5$O$_3$S$_1$+1.9TFA+1H$_2$O) C, H, N, F, S, Cl.

EXAMPLE 59
Preparation of {4-[(2-tetrazolyl)phenyl]phenylcarbonyl}methyl-6-amidinobenzimidazole MP: 144–145° C.; $^1$H NMR (CD$_3$OD) δ8.56 (bs, 1H), 8.11–8.09 (m, 3H), 7.93 (d, J=8.5 Hz, 1H), 7.76 (dd, J=8.5 Hz, J=1.7 Hz, 1H), 7.73 (d, J=7.3 Hz, 2H), 7.67–7.62 (m, 2H), 7.38 (d, J=8.8 Hz, 2H), 6.09 (s, 2H); $^{13}$C NMR (CD$_3$OD) δ192.97, 168.66, 156.91, 149.40, 147.07, 146.51, 142.32, 135.60, 134.66, 132.64, 131.79, 131.71, 130.90, 129.88, 129.47, 124.56, 123.43, 120.75, 112.87, 52.45; MS: 212.2 (M+2H)$^{2+}$; HRMS: 423.1686 (obs.), 423.1682 (calcd.); Anal.: (C$_{23}$H$_{18}$N$_8$O$_1$+1.9TFA+1 HCl+0.5H$_2$O) C, H, N, F, S, Cl.

Method B: Examples 60, 61 and 62 were made by alkylation of 5-cyanobenzimidazole with [4-(2-tert-butylaminosulfonylphenyl)phenylaminocarbonyl]methylene chloride, or (4-benzylpiperidinecarbonyl)methylene chloride, followed by Pinner reactions.

EXAMPLES 60 AND 61
Preparation of [4-(2-aminosulfonylphenyl)phenylaminocarbonyl]methyl-6-amidinobenzimidazole (Example 60) and [4-(2-aminosulfonylphenyl)phenylaminocarbonyl]methyl-5-amidinobenzimidazole (Example 61)

[4-(2-tert-Butylaminosulfonylphenyl)phenylaminocarbonyl]methylene chloride was prepared by acylation of 4-[(o-SO$_2$NHtBu)phenyl]aniline (3 mmol) with α-chloroacetyl chloride (4 mmol) in CH$_3$CN (100 mL) and K$_2$CO$_3$ (4 mmol).

Alkylation of 5-cyanobenzimidazole (2 mmol) with [4-(2-tert-butylaminosulfonylphenyl)phenyl-aminocarbonyl]methylene chloride (2 mmol) in DMF (10 mL) and K$_2$CO$_3$ (4 mmol) at r.t. over 16 hours, followed by purification on thin layer TLC plates, and further isolation by HPLC gave [4-(2-tert-butylaminosulfonylphenyl)phenylaminocarbonyl]methyl-6-cyanobenzimidazole (240 mg, 56%) and [4-(2-tert-butylaminosulfonylphenyl)phenylaminocarbonyl]methyl-5-cyanobenzimidazole (160 mg, 37%).

[4-(2-tert-Butylaminosulfonylphenyl)phenylaminocarbonyl]methyl-6-cyanobenzimidazole was converted to Example 60 via the Pinner reaction and purified by HPLC: MP: 134–136° C.; $^1$H NMR (CD$_3$OD) δ8.73 (bs, 1H), 8.15 (s, 1H), 8.10 (dd, J=8.6 Hz, J=1.2 Hz, 1H), 7.93 (d, J=8.3 Hz, 1H), 7.75 (d, J=7.4 Hz, 1H), 7.64 (d, J=8.4 Hz, 2H), 7.60 (dd, J=7.6 Hz, J=1.2 Hz, 1H), 7.52 (td, J=7.6, J=1.4 Hz, 1H), 7.40 (d, J=8.8 Hz, 2H), 7.32 (dd, J=7.6 Hz, J=1.2 Hz, 1H), 5.36 (s, 2H); $^{13}$C NMR (CD$_3$OD) δ168.79, 166.75, 143.05, 141.48, 138.93, 137.50, 133.63, 132.92, 131.28, 128.75, 128.59, 124.63, 123.35, 120.96, 120.53, 112.80, 47.51; MS: 449.3 (M+H)$^+$; HRMS: 449.1401 (obs.), 449.1396 (Calcd.); Anal.: (C$_{22}$H$_{20}$N$_6$O$_3$S$_1$+1.8TFA+0.25 HCl+1H$_2$O) C, H, N, F, S, Cl.

[4-(2-tert-Butylaminosulfonylphenyl)phenylaminocarbonyl]methyl-5-cyanobenzimidazole was converted to Example 61 via the Pinner reaction and purified by HPLC: MP: 254° C. (Dec.); $^1$H NMR (CD$_3$OD) δ8.55 (s, 1H), 8.22 (s, 1H), 8.08 (d, J=6.6 Hz, 1H), 7.83–7.75 (m, 2H), 7.62 (d, J=8.8, 2H), 7.59–7.52 (m, 2H), 7.39 (d, J=8.4 Hz, 2H), 7.31 (d, J=7.4 Hz, 1H), 5.33 (s, 2H); $^{13}$C NMR (DMSO-d$_6$) δ165.73, 164.97, 147.72, 142.58, 142.19, 139.43, 138.17, 137.63, 135.23, 132.31, 131.35, 129.69, 127.39, 127.23, 122.20, 121.03, 120.96, 120.17, 118.21, 118.12, 111.24, 47.51; MS: 449.3 (M+H)$^+$; HRMS: 449.1414 (obs.), 449.1396 (calcd.); Anal.: (C$_{22}$H$_{20}$N$_6$O$_3$S$_1$+2TFA+0.15 HCl+1.5H$_2$O) C, H, N, F, S, Cl.

EXAMPLE 62
Preparation of 1-(4-benzylpiperidinecarbonyl)methyl-6-amidinobenzimidazole and 1-(4-benzylperidinecarbonyl)methyl-5-amidinobenzimidazole (4-Benzylpiperidinecarbonyl)methylene chloride was prepared by acylation of 4-benzylpiperidine (100 mmol) with a-chloroacetyl chloride (100 mmol) in THF (250 mL) and K$_2$CO$_3$ (100 mL. Alkylation of 5-cyanobenzimidazole (2 mmol) with (4-benzylpiperidinecarbonyl)methylene chloride (2 mmol) in DMF (5 mL) in the presence of NaH (3 mmol) at from 0° C. to room temperature over 16 hours, followed by purification on TLC plates gave 1-(4-benzylpiperidinecarbonyl)methyl-6-cyanobenzimidazole and 1-(4-benzylpiperidinecarbonyl)methyl-5-cyanobenzimidazole (0.4 g, 56% of yield). This mixture (1.11 mmol) was then carried through the Pinner reaction, followed by purification on TLC plates with 10% MeOH in CH$_2$Cl$_2$, and further purification by HPLC to give the title compounds: MP: 54–56° C.; MS: 376.4 (M+H)$^+$; HRMS:376.2118 (obs.), 376.2137 (calcd.); Anal.: (C$_{22}$H$_{25}$N$_5$O$_1$+1.8TFA+0.1 HCl).

Method C: Example 63 was made by Ulmann coupling reaction of 4-chloro-3-nitrobenzenitrile with (4-benzylpiperidinecarbonyl)methylamine, followed by reduction of 4-[(4-benzylpiperidinecarbonyl)methyl]amino-3-nitrobenzonitrile, cyclization with formic acid, and finally the Pinner reaction.

EXAMPLE 63
Preparation of 1-(4-benzylpiperidinecarbonyl)methyl-6-amidinobenzimidazole (4-Benzylpiperidinecarbonyl)methylamine was made by treatment of (4-benzylpiperidinecarbonyl)methylene chloride with $NaN_3$ in aqueous acetone, followed by hydrogenation with 5% Pd/C. Reaction of (4-benzylpiperidinecarbonyl)methylamine (8.6 mmol) with 4-chloro-3-nitro-benzonitrile (10 mmol) in DMF (10 mL) in the presence of $NaHCO_3$ (10 mmol) at 100° C. for 16 hours gave 4-[(4-benzylpiperidinecarbonyl)methyl]amino-3-nitrobenzonitrile (1.6 g, 49.2% of yield), which was then hydrogenated in MeOH in the presence of 5% of Pd/C (10% w/w) to produce 1-(4-benzylpiperidinecarbonyl)methyl-6-cyanobenzimidazole (1.3 g, 90% of yield). 1-(4-Benzylpiperidinecarbonyl)methyl-6-cyanobenzimidazole (0.57 mmol) was then carried through the Pinner reaction, followed by purification on TLC plates with 10% MeOH in $CH_2Cl_2$, and further purification by HPLC to give the title compound: mp: 68–70° C.; $^1H$ NMR ($CD_3OD$) δ8.52 (s, 1H), 8.20 (s, 1H), 7.75 (s, 2H), 7.29–7.24 (m, 2H), 7.18–7.16 (m, 3H), 5.43 (dd, J=17.2 Hz, J=24.5 Hz, 2H), 4.40 (d, J=12.8 Hz, 1H), 4.00 (d, J=12.8 Hz, 1H), 3.18 (t, J=12.8 Hz, 1H), 2.68 (t, J=12.8 Hz, 1H), 2.59 (d, J=7.00 Hz, 2H), 1.87–1.78 (m, 2H), 1.72–1.68 (m, 1H, 1.42–1.35 (m, 1H), 1.22–1.15 (m, 1H); $^{13}C$ NMR ($CD_3OD$) δ168.76, 166.06, 148.73, 141.23, 139.50, 130.17, 129.45, 129.33, 127.35, 127.11, 124.04, 120.40, 113.19, 47.38, 46.36, 43.93, 43.73, 39.15, 33.35, 32.73; MS: 188.8 $(M+2H)^{2+}$; HRMS:376.2130 (obs.), 376.2137 (calcd.); Anal.: ($C_{22}H_{25}N_5O_1+1.85TFA+0.18HCl+0.5H_2O$).

EXAMPLE 64
Preparation of 2-[4-(2-aminosulfonylphenyl)phenylcarbonyl]methyl-6-amidinobenzimidazole N-ethylmalonyl-4'-aminobiphenyl-2-tert-butylsulfonamide. To a solution of 1.01 g of 4'-aminobiphenyl-2-tert-butylsulfonamide in 30 mL anhydrous methylene chloride and 0.93 mL triethylamine was added 0.43 mL of ethylmalonyl chloride by dropwise addition. Let reaction mixture stir overnight at ambient temperature. Concentrated in vacuo to give a residue which was taked up in 50 mL ethyl acetate. The organics were washed 3×20 mL water. The resulting organics were dried over magnesium sulfate and concentrated under reduced pressure to give the crude product. The crude product was purified via standard chromatographic technique to give 0.70 g of N-ethylmalonyl-4'-aminobiphenyl-2-tert-butylsulfonamide. LRMS($NH_3$–CI): 436(M+$NH_4$). $^1H$ NMR($CDCl_3$, 300 MHz): δ9.42 (s, 1H), 8.18 (d, 1H), 7.79 (d, 2H), 7.52 (m, 3H), 7.49 (d, 1H), 7.30 (d, 1H), 4.30 (q, 2H), 3.60 (s, 1H), 3.50 (s, 2H), 1.35 (t, 3H), 1.0 (s, 9H).

2-[4-(2-aminosulfonylphenyl)phenylcarbonyl]methyl-6-cyanobenzimidazole. A mixture of 0.32 g of 3,4-diaminobenzonitrile and 0.70 g of N-ethylmalonyl-4'-aminobiphenyl-2-tert-butylsulfonamide was heated to 180° C. For 20 h. Let mixture cool to ambient temperature. Concentration and high vacuum gave 0.09 g of crude 2-[4-(2-aminosulfonylphenyl)phenylcarbonyl]methyl-6-cyanobenzimidazole. The crude material was carried through to the next reaction sequence. LRMS(ES+): 431 (M+H).

2-[4-(2-aminosulfonylphenyl)phenylcarbonyl]methyl-6-amidinobenzimidazole. A solution of the crude 2-[4-(2-aminosulfonylphenyl) phenylcarbonyl]methyl-6-cyanobenzimidazole in 10 mL 1:1 anhydrous chloroform to anhydrous ethanol was stirred in an ice bath. Hydrogen choride gas was bubbled into the reaction vessel for 20 minutes. Then the reaction mixture was allowed to warm to ambient temperature over 15 h. Concentrated the reaction mixture under reduced pressure and placed the crude product on high vacuum. The resultant ethylimidate was treated directly with 0.30 g of ammonium carbonate in anhydrous ethanol. The reaction mixture was stirred at ambient temperature for 24 h. Concentrated reaction mixture under reduced pressure and purified crude product via standard HPLC technique to give purified 2-[4-(2-aminosulfonylphenyl)phenylcarbonyl]methyl-6-amidinobenzimid-azole. LRMS(ES+): 449(m+H). HRMS (FAB): calcd 449.139586 mass 449.139273. $^1H$ NMR (DMSO, d6, 300 MHz): δ10.50 (s, 1H), 9.20 (bs, 2H), 8.67 (bs, 2H), 7.79 (d, 2H), 7.55 (m, 4H), 7.25 (m, 4H), 4.05 (s, 2H).

EXAMPLE 65
Preparation of 2-[4-(2-tert-butylaminosulfonylphenyl)phenylcarbonyl]methyl-5-azabenzimidazole N-ethylmalonyl-4'-aminobiphenyl-2-tert-butylsulfonamide. To a solution of 1.01 g of 4'-aminobiphenyl-2-tert-butylsulfonamide in 30 mL anhydrous THF and 0.93 mL of triethylamine was added 0.43 mL of ethylmalonyl chloride by dropwise addition. Let reaction mixture stir for 24 h. Concentrated in vacuo to give a residue which was taked up in 5 mL ethyl acetate. The organics were washed 3×20 mL water. The resultant organics were dried over magnesium sulfate and concentrated under reduced pressure. The crude product was purified via standard chromatographic technique to give 0.63 g of N-ethylmalonyl-4'-aminobiphenyl-2-tert-butylsulfonamide. LRMS($NH_3$–CI): 436(M+$NH_4$). $^1H$ NMR($CDCl_3$, 300 MHz): δ9.42 (s,1H), 8.18 (d,1H), 7.79 (d,2H), 7.52 (m,3H), 7.49 (d,1H), 7.30 (d,1H).

2-[4-(2-tert-butylaminosulfonylphenyl)phenylcarbonyl]methyl-5-azabenzimidazole. A mixture of 0.026 g of 3,4-diaminopyridine and 0.10 g of N-ethylmalonyl-4'-aminobiphenyl-2-tert-butylsulfonamide was heated to 165° C. for 20 h. Let mixture cool to ambient temperature. Purified crude material by standard chromatographic technique to give the 2-[4-(2-tert-butylaminosulfonylphenyl)phenylcarbonyl]methyl-6-azabenzimidazole. LRMS(ES+): 464(M+H). HRMS($NH_4$–CI): Mass 464.175637 Calcd 464.175630. $^1H$ NMR($CDCl_3$, 300 MHz): δ9.49 (s,1H), 8.40 (s,1H), 8.15 (d,1H), 7.98 (s,1H), 7.47 (m,3H), 7.31 (d,2H), 7.25 (d,2H), 4.30 (s,2H), 1.0 (s,9H).

EXAMPLE 66
Preparation of 2S-[4-(2-tert-aminosulfonylphenyl)phenylaminocarbonyl]methyl-thio-1H-imidazo(4,5-C) pyridine To a solution of 1H-imidazo(4,5-C) pyridine-2-thiol (37 mg, 0.245 mmol) in DMF (2.5 mL) was added 4-(2-tert-butylaminosulfonylphenyl)phenylaminocarbonyl]methyl chloride (75 mg, 0.197 mmol) and then $K_2CO_3$ (58 mg, 0.42 mmol), and the resulting mixture was heated at 120° C. for 1 hour. To the mixture at room temperature was added HCl (1 N in $Et_2O$, 1 mL) and then MeOH (6 mL), a clear solution was obtained. To it was then slowly added $Et_2O$ (200 ml), and a white suspension was observed, which was filtered and a white solid (120 mg) was collected. The solid was soluble in DMSO (8 mL), and the resulting solution was purified by HPLC with $H_2O$—$CH_3CN$—TFA to give the title compound (60 mg). HRMS $(M+H)^+$ calc. m/z: 496.1477, obs: 496.1492.

EXAMPLE 67
Preparation of 2S-[4-(2-aminosulfonylphenyl)phenylaminocarbonyl]methyl-thio-1H-imidazo(4,5-C) pyridine A solution of Example 66 (26 mg) in TFA (0.5 mL) was heated for 16 hours. Removed all of the solvent and purified by HPLC with $H_2O$—$CH_3CN$—TFA to give the title compound (13 mg). HRMS $(M+H)^+$ calc. m/z: 440.0851, obs: 440.0831.

EXAMPLE 101

Preparation of 1-(4-benzylpiperidinecarbonyl)methyl-5-amidinoindole

5-Cyanoindole-1-methylacetate. To a stirred solution of 5-cyanoindole (5.0 g, 35.2 mmol) in 10 mL of dry DMF at 0° C. under $N_2$ atmosphere was added NaH (1.1 g, 42.2 mmol). The reaction was stirred for 30 min. and then α-bromomethylacetate (5.4 g, 35.2 mmol) was added and stirred at room temperature for 2 h. It was then quenched with $H_2O$, extracted with ethyl acetate (3×), dried with $Na_2SO_4$, filtered and concentrated in vacuo to afford a light yellow solid (7.5 g, 35.2 mmol). $^1H$ NMR ($CDCl_3$) δppm 3.2 (s, 2H), 3.8 (s, 3H), 7.03 (s, 1H), 7.32 (d, 1H, J=7.5Hz), 7.41 (d, 1H, J=7.5Hz), 7.61 (s, 1H), 7.81 (s, 1H). LRMS $NH_3$–CI m/z $(M+H)^+$ 229, $(M+NH_4)^+$ 246.

3-(5-Cyanoindole) acetic acid. Methyl-5-cyanoindole-1-acetate was saponified in MeOH, KOH (3.3 eq) at rt for 18 h. The mixture was concentrated in vacuo, dissolved in water, extracted with diethylether (2×) and the acidic aqueous layer was acidified with 2 N HCl. The resulting white solid was filtered and dried in a vacuum oven to afford 6.2 g of the title compound. LRMS ESI $(M+H)^+$ 201.

1-(4-Benzylpiperidinecarbonyl)methyl-5-cyanoindole. To a stirred complex of 3-acetic acid-5-cyanoindole (2.0 g, 0.1 mmol) and 1-(3-dimethylaminopropyl)-3-ethylcarbodiimide hydrochloride (DEC) in dry $CH_2Cl_2$ was added 4-benzylpiperidine (1.8 g, 0.01 mmol). The mixture was stirred under $N_2$ atmosphere for 18 h, then concentrated in vacuo, dissolved in ethyl acetate, washed with 1 N HCl (3×), $NaHCO_3$ (3×), brine (2×), dried with $Na_2SO_4$, filtered and concentrated in vacuo to afford a white solid (2.8 g). HRMS for $C_{23}H_{24}N_3O$ $(M+H)^+$ calc. 358.191938, found 358.193278.

1-(4-Benzylpiperidinecarbonyl)methyl-5-amidinoindole. N-1-Acetyl-1-N'-piperidinyl-4-benzyl-5-cyanoindole (500 mg), was dissolved in dry MeOH (30 mL) cooled to 0° C. and saturated with HCl(g). The resulting solution was allowed to warm up to rt over 18 h. The mixture was concentrated in vacuo, re-dissolved in dry MeOH and $(NH_4)_2CO_3$ (672.0 mg) was added, flask sealed and stirred for 18 at rt. The resulting suspension was filtered through Celite®, rinsed with dry MeOH, concentrated in vacuo to afford 997 mg of product (89% by HPLC); 100 mg of which was further purified via prep HPLC to afford 29 mg (100% purity by HPLC). M.p. 214–215° C. HRMS ($NH_3$–CI) for $C_{23}H_{26}N_4O$ $(M+H)^+$ calc. 375.217601, found 375.218487. $^1H$ NMR ($CD_3OD$) δppm 1.05 (qd, 1H, J=7.5 Hz, J=2.5 Hz), 1.25 (qd, 1H, J=7.5, J=2.5 Hz), 1.65 (bd, 1H, J=7.5 Hz), 1.76 (bd, 1H, J=7.5 Hz), 1.83 (m, 1H), 2.58 (d, 2H, J=6.0 Hz0, 2.63 (t, 1H, J=75 Hz), 3.07 (t, 1H, J=7.5 Hz), 4.03 (bd, 1H, J=7.5 Hz), 4.2 (bd, 1H, J=7.5 Hz), 5.21 (qd, 2H, J=7.5 Hz), 6.63 (s, 1H), 7.18 (m, 3H), 7.23 (m, 2H), 7.38 (s, 1H), 7.51 (d, 1H, J=5.0 Hz), 7.58 (d, 1H, J=5.0 Hz), 8.05 (s, 1H).

EXAMPLE 102

Preparation of 1-(4-benzylpiperidinecarbonyl)ethyl-5-amidinoindole

Methyl-5-cyanoindole-3-propionate. To a stirred solution of 5-cyanoindole (1.0 g, 7.0 mmol), $K_2CO_3$ (0.966 g, 7.0 mmol) in acetonitrile was added 3-bromomethylpropionate (1.17 g, 7.0 mmol). The mixture was stirred at reflux for 18 h under a nitrogen atmosphere, cooled, diluted with $H_2O$, extracted with ethyl acetate, dried with $Na_2SO_4$, filtered and concentrated in vacuo to afford 1.59 g of product. $^1H$ NMR ($CD_3OD$) δppm 2.85 (t, 2H, J=6.6 Hz), 3.61 (s, 3H), 4.58 (t, 2H, J=6.6 Hz), 6.61 (s, 1H), 7.42, (m, 3H), 7.62 (d, 1H, J=8.4 Hz), 7.99 (s, 1H).

5-Cyanoindole-3-propionic acid. Methy-5-cyanoindole-3-propionate (200 mg) was saponified in MeOH (10 mL)/KOH (150 mg, 0.88 mmol) at rt for 18 h. The solution was concentrated in vacuo, dissolved in water and washed with chloroform. The acidic layer was acidified and extracted with ethyl acetate, dried with $Na_2SO_4$, filtered and concentrated in vacuo to afford 188 mg of product. $^1H$ NMR ($CD_3OD$) δppm 2.83 (t, 2H, J=6.6Hz), 4.43 (t, 2H, J=6.6 Hz), 6.6 (nd,1H, J3.2 Hz), 7.42 (d, 2H, J=7.3 Hz), 7.43 (s, 1H), 7.61 (d, 1H, J=7.3 Hz), 7.99 (s, 1H); LRMS ESI $(M+H)^+$ 215.

1-(4-Benzylpiperidinecarbonyl)ethyl-5-amidinoindole. Preparation follows the same last two steps of example 101. Afforded 156 mg of the TFA salt $^1H$ NMR (DMSO-$d_6$) δppm 2.42 (m, 4H), 2.89 (m, 4H), 3.21 (d, 2H, J=5.0 Hz), 3.72 (bd, 1H, J=10.0 Hz), 4.12 (m,1H), 4.38 (bd, 1H, J=10 Hz), 4.51 (m, 2H), 6.62 (s, 1H), 7.1–7.31 (m, 5H), 7.62 (m,2H), 7.72 (d, 1H, J=6.0 Hz), 8.21 (bs, 1H); HRMS $(M+H)^+$ for $C_{24}H_{29}N_4O$ calc. 389.234137, found 389.231258.

EXAMPLE 103

Preparation of 1-(4-(3-fluoro)benzylpiperidinecarbonyl)methyl-5-amidinoindole 4-(3-Fluorobenzyl)piperidine. To a stirred solution of 1-benzylpiperidin-4-one (0.99 mL, 5.34 mmol) in THF was added $Ph_3P$=CH-(3-fluoro)phenyl (2.41 g, 5.34 mmol) at 0° C. under a nitrogen atmosphere. After stirring for 4 h at rt, the reaction was quenched with $H_2O$, concentrated in vacuo and the residue was chromatographed on silica gel using 1:1 hexanes:ethyl acetate as the eluant to afford 313 mg of product. LRMS $NH_3$–CI $(M+H)^+$ 282. The product (330 mg) was hydrogenated in MeOH, 10% Pd/C (300 mg) and conc. HCl (5 mL) in a parr shaker at 50 psi for 18 h. The reaction was filtered through Celite® and the filtrate was concentrated in vacuo to afford 250 mg of the title compound. LRMS $NH_3$–CI $(M+H)^+$ 194.

1-(4-(3-Fluoro)benzylpepiridinocarbonyl)methyl-5-cyanoindole. Prepared as in example 101. LRMS ESI $(M+H)^+$ 376.

1-(4-(3-Fluoro)benzylpepiridinocarbonyl)methyl-5-amidinoindole. Example 103 was prepared via the same method as example 101. HRMS FAB glycerol matrix for $C_{23}H_{26}N_4FO$ $(M+H)^+$ calc. 393.209065, found 393.208858.

EXAMPLE 104

Preparation of 1-(1-(4-amidino)benzyl-N-(methylacetate) aminocarbonyl)methyl-5-amidinoindole (4-Cyano)benzyl-N-(methylacetate) amine. α-Bromo-tolunitrile (2.0 g, 10.5 mmol) was dissolved in $CHCl_3$ and glycine methyl ester (2.64 g, 21.0 mmol) and triethyl amine (2.92 mL, 10.5 mmol) was added. The mixture was stirred for 18 h under nitrogen atmosphere, concentrated in vacuo and purified via silica gel column using 1:1 hexanes:ethyl acetate as the eluant to afford 1.07 g of the title compound (5.25 mmol). LRMS ESI $(M+H)^+$ 205. $^1H$ NMR ($CDCl_3$) δppm 3.42 (s, 2H), 3.78 (s, 3H), 3.91 (s, 2H), 7.42 (d, 2H, J=8.0 Hz), 7.62 (d, 2H, J=8.0 Hz).

1-(1-(4-Cyano)benzyl-N-(methylacetate)aminocarbonyl) methyl-5-cyanoindole. Compound was prepared using the same coupling procedure as in example 101. HRMS $NH_3$–CI for $C_{23}H_{20}N_4O_3$ $(M+H)^+$ calc. 401.161366, found 401.159527.

1-(1-(4-Amidino)benzyl-N-(methylacetate) aminocarbonyl)methyl-5-amidinoindole. Prepared by the same Pinner conditions as example 101. LRMS ESI (M+2H)$^{+2}$ 218.

EXAMPLE 105
Preparation of Methyl 1-(4-benzylpiperidine-1-carbonyl) methyl-5-amidinoindole-3-propanoate Methyl 1-(4-benzylpiperidine-1-carbonyl)methyl-5-cyanoindole-3-propanoate. 1-(4-Benzylpiperidine-1-carbonyl)-5-cyanoindole (1.0 g, 2.8 mmol) was dissolved in 20 mL of dry $CH_2Cl_2$, cooled to 0° C. and oxalyl chloride (1.07 g, 8.4 mmol) was added. The reaction stirred for 3 h at rt. It was then concentrated in vacuo and dissolved in dry MeOH (20 mL) and stirred for 18 h. The resulting yellow solution was concentrated in vacuo and 1.0 g (2.3 mmol) was taken up in TFA (20 mL) at 0° C. and triethylsilane (535 mg, 4.6 mmol) was slowly added. The reaction stirred at 0° C. for 3 h and then it was concentrated in vacuo, dissolved in $CH_2Cl_2$ and washed with sat. $NaHCO_3$, dried with sodium sulfate, filtered and concentrated. The resulting residue was chromatographed via silica gel using 7% MeOH/$CHCl_3$ as the eluant to afford 840 mg of the title compound. LRMS ESI (M+H)$^+$ 430.

1-(4-Benzylpiperidine-1-carbonyl)methyl-3-methylacetate-5-amidinoindole. The amidine was prepared as in example 101. HRMS $NH_3$–CI for $C_{26}H_{34}N_4O_3$ (M+H)$^+$ calc. 447.239616, found 447.241907.

EXAMPLE 106
Preparation of 1-((4-benzylpiperidinecarbonyl)methyl-(3-ethanehydroxyl)-5-amidinoindole 1-(4-Benzylpiperidine-1-carbonyl)methyl-3-ethanehydroxyl-5-cyanoindole. Methyl 1-acetyl-(4-benzylpiperidin-1-yl)-3-acetate-5-cyanoindole (100 mg, 0.233 mmol) was dissolved in ethanol and sodium borohydride (20 mg, 0.51 mmol) was added and the solution stirred at rt for 18 h. The reaction was concentrated in vacuo diluted with water and extracted with methylene chloride (3×), dried over sodium sulfate, filtered and concentrated in vacuo to afford 93.0 mg of the title compound. LRMS DCI–$NH_3$ (M+$NH_4$)$^+$ 419.

1-(4-Benzylpiperidine-1-carbonyl)methyl-3-ethanehydroxyl-5-amidinoindole. The amidine was prepared as in example 101. HRMS $NH_3$–CI for $C_{25}H_{31}N_4O_2$ (M+H)$^+$ calc. 419.244702, found 419.245383.

EXAMPLE 107
Preparation of 1-(4-benzylpiperidine-1-carbonyl)methyl-3-methylcarboxylic acid-5-amidinoindole Methyl 1-acetyl-(4-benzylpiperidin-1-yl)-3-acetate-5-amidinoindole was hydrolyzed in TFA/$H_2O$ for 18 h. Purified via prep HPLC to afford the title compound. LRMS (M+H)$^+$ 433.

EXAMPLE 108
Preparation of 1-(1-Benzylpiperidine-4-aminocarbonyl) methyl-5-amidinoindole 1-(1-Benzylpiperidine-4-aminocarbonyl)methyl-5-cyanoindole. To a stirred complex of N-1-methylenecarbohydroxy-5-cyanoindole (300 mg, 1.5 mmol) and DEC was added 4-amino-1 benzylpiperidine and triethylamine (0.209 mL, 1.5 mmol). The reaction was stirred at rt for 18 h. The volatiles were removed in vacuo and the residue was purified via silica gel using 1% MeOH/$CH_2Cl_2$ as the eluant to afford 160 mg of product. HRMS $NH_3$–CI for $C_{23}H_{24}N_4O$ (M+H)$^+$ calc 373.204.204739, found 373.202837.

1-(1-Benzylpiperidine-4-aminocarbonyl)methyl-5-amidinoindole. The amidine was prepared as in example 101 to afford 96 mg of the title compound. HRMS $NH_3$–CI calc. 390.229386, found 390.229386.

EXAMPLE 109
Preparation of 1-(4-benzoylpiperidinecarbonyl)methyl-5-amidinoindole 1-(4-Benzoylpiperidinecarbonyl)methyl-5-cyanoindole. Prepared as in example 108 except using 4-benzoylpiperidine. HRMS $NH_3$–CI (M+H)$^+$ for $C_{23}H_{21}N_3O_2$ calc.372.171702, found 372.171620.

1-(4-Benzoylpiperidinecarbonyl)methyl-5-amidinoindole. The amidine was prepared using the same method as in example 101. HRMS (M+H)$^+$ for $C_{23}H_{24}N_4O_3$ calc. 389.197751, found 389.198109.

EXAMPLE 110
Preparation of 1-(4-(3-fluoro)benzylpiperazinecarbonyl) methyl-5-amidinoindole 1-(4-(3-Fluoro)benzylpiperazinecarbonyl)methyl-5-cyanoindole To a stirred solution of 1-acetyl-(1-piperazine)-5-cyanoindole (400 mg, 1.31 mmol), triethylamine (0.0.36 mL, 2.62 mmol) in diethyl ether was added 3-fluorobenzyl bromide (0.161 mL, 1.31 mmol) and stirred at room temperature under $N_2$ atmosphere for 18 h. The reaction quenched with water, extracted with ethyl acetate, dried with sodium sulfate, filtered and concentrated in vacuo to afford 438 mg product. LRMS (M+H)$^+$ 377.

1-(4-(3-Fluoro)benzylpiperazinecarbonyl)methyl-5-amidinoindole. Prepared as in example 101. HRMS (M+H)$^+$ for $C_{22}H_{24}N_5OF$ calc. 394.204314, found 394.204917.

EXAMPLE 111
Preparation of 1-(4-phenylbenzylaminocarbonyl)methyl-5-amidinoindole 1-(4-Phenylbenzylaminocarbonyl)methyl-5-cyanoindole. To a stirred complex of 1-acetic acid 5-cyanoindole (250 mg, 1.25 mmol) and DEC (239 mg,1.25 mmol) in methylene chloride was added 4-phenybenzylamine (228 mg, 1.25 mmol). After stirring at rt for 18 h under a nitrogen atmosphere, the reaction was concentrated in vacuo, dissolved in ethyl acetate, washed with 1 N HCl, sodium bicarbonate, and brine, dried with sodium sulfate, filtered and concentrated in vacuo to afford 215 mg of product. HRMS (M+H)$^+$ calc. 366.260637, found 366.160323.

1-(4-Phenylbenzylamninocarbonyl)ethyl-5-amidinoindole. Prepared as in example 101. HRMS calc. 383.187187 found 383.189667.

EXAMPLE 112
Preparation of methyl 1-(4-benzylpiperidinecarbonyl) methyl-5-amidinoindole-3-propenoate Methyl 1-(4-benzylpiperidinecarbonyl)methyl-5-cyanoindole-3-propenoate. To a stirred solution of DMF (15 mL) and $POCl_3$ (256 mg, 1.7 mmol) at 0° C. was added 1-(4-benzylpiperidinecarbonyl)methyl-5-cyanoindole (199 mg, 0.56 mmol). After stirring 3 h, the reaction was quenched with 2 N sodium hydroxide and stirred for 30 min. It was then extracted with chloroform, dried with sodium sulfate, filtered and concentrated in vacuo to afford product. LRMS (M+H)$^+$ 386. The product was then refluxed in the presence of triphenyl phosphonium (methylenecarbomethoxy)ylide in THF under a nitrogen atmosphere for 18 h. The reaction was concentrated in vacuo and the residue purified via silica gel chromatography using 7%MeOH/$CHCl_3$ as the eluant to afford 140 mg of product.

Methyl 1-(4-benzylpiperidinecarbonyl)methyl-5-amidinoindole-3-propenoate. Prepared as in example 101. LRMS (M+H)$^+$ 459.

EXAMPLE 113
Preparation of 1-(4-(2-fluoro)benzylpiperidinecarbonyl) methyl-5-amidinoindole 4-(2-Fluoro)benzylpiperidine. To a stirred solution of triphenylphosphonium-2-fluorobenzylbromide in dry THF at −78° C. was added n-buLi (2.5 M, 2.13 mL) and stirred for 30 min. To it was then added 1-benzyl-4-piperidinene (0.99 mL) and the mixture stirred at rt for 4 h. The reaction was quenched with water and concentrated in vacuo. The resulting residue was purified via silica gel chromatrography using 1:1 hexanes:ethyl acetate as the eluant to afford 313 mg. LRMS (M+H)$^+$ 282. The product was hydrogenated in a parr shaker at 50 psi in MeOH (10 mL), 5.0 mL conc. HCl and 10%Pd/C (300 mg) for 18 h. The mixture was filterd through celite® and concentrated in vacuo to afford 250 mg of product. LRMS (M+H)$^+$ 194.

1-(4-(2-Fluoro)benzylpiperidinecarbonyl)methyl-5-cyanoindole. Prepared by coupling 3-acetic acid-5-cyanoindole with 4-(2-fluoro)benzylpiperidine using the method described in example 101. LRMS (M+H)$^+$ 376.

1-(4-(2-Fluoro)benzylpiperidinecarbonyl)methyl-5-amidinooindole. Prepared as in example 101. HRMS (M+H)$^+$ calc. 393.209065, found 393.208858.

EXAMPLE 201
Preparation of 3-((4-cyclohexyl) phenylaminomethylcarbonyl)methyl-5-amidinoindole Methyl 5-cyanoindole-3-acetate. To a stirred solution of 5-cyanoindole (10.0 g) in dry methylene chloride was added (3.0 eq, 61.43 mL) of oxalyl chloride. After stirring for 1 h under a nitrogen atmosphere at rt, the resulting precipitate was filtered and rinsed with diethyl ether. The solids were then taken up in dry MeOH and stirred for 1 h. At this time the solids were filtered and rinsed with MeOH and diethyl ether to afford 5.93 g of methyl α-ketoacetate 5-cyanoindole. LRMS (M+H)$^+$ 229. Methyl α-ketoacetate (4.90 g) was dissolved in 50 mL trifluoro acetic acid at 0° C. and triethyl silane (5.0 g) was slowly added via a drop funnel (20 min.). It was then stirred at 0° C. for 3 h. The resulting yellow solution was concentrated in vacuo, neutralized with sodium bicarbonate, extracted with diethyl acetate, dried with magnesium sulfate filtered and concentrated in vacuo. Purification was accomplished via silica gel chromatography using 1% MeOH/CH$_2$Cl$_2$ as the eluant to afford 2.48 g of product. LRMS (M+H)$^+$ 232.

3-(5-Cyanoindole) acetic acid. The above ester was saponified in KOH/MeOH at rt for 18 h. The solution 3 was then concentrated in vacuo, dissolved in water, extracted with ethylacetate and the acidic layer was then acidified with 1 N HCl at 0° C. The resulting white solids were filtered and further dried under high vacuum to afford the product. M.p. 196.5–198.5; Calc. C66.00 H4.04 N13.99, found C65.71 H4.24 N13.94. $^1$H NMR (CD$_3$OD) δppm 3.78 (s, 2H), 7.28 (s, 1H), 7.38 (d, 1H, J=8.6 Hz), 7.45 (d, 1H, J=8.6 Hz), 7.89 (s, 1H); LRMS (M+)$^+$ 199.

3-(4-Cyclohexylphenylaminomethylcarbonyl)methyl-5-cyanoindole. To a stirred complex of the 5-cyanoindole acetic acid (312 mg, 1.5 mmol) and BOP reagent (1.03 g) in DMF was added 4-cyclohexylphenylaminomethyl. After heating at 50° C. under a nitrogen atmosphere for 18 h, the reaction was cooled to rt diluted with water and extracted with ethyl acetate, washed with 1 N HCl, sat. sodium bicarbonate, and brine, dried with sodium sulfate, filtered and concentrated in vacuo. The residue was purified via chromatography using 100% ethyl acetate as the eluant to afford 210 mg of product. LRMS (M+H)$^+$ 372.

3-((4-Cyclohexyl)phenylaminomethylcarbonyl)methyl-5-amidinoindole. Prepared as in example 101. HRMS (M+H)$^+$ for C$_{24}$H$_{29}$N$_4$O calc. 389.234137, found 389.232086.

EXAMPLE 202
Preparation of 3-(4-p-toluenesulfonyl-piperazinecarbonyl) methyl-5-amidinoindole 3-(4-Paratoluensulfonylpiperazinecarbonyl)methyl-5-cyanoindole. To a stirred solution of 3-(piperazinecarbonyl) methyl-5-cyanoindole hydrochloride (200 mg, 0.66 mmol) and triethylamine (134 mg, 185 μL) in chloroform was added toluenesulfonylchloride (126 mg, 0.66 mmol). After stirring for 18 h at rt under a nitrogen atmosphere, the reaction was quenched with water, extracted with chloroform, washed with 1 N HCl, sat sodium bicarbonate, and brine, dried with sodium sulfate, filtered and concentrated in vacuo to afford 237 mg of product. LRMS (M+H)$^+$ 423.

3-(4-Paratoluensulfonylpiperazinecarbonyl)methyl-5-amidinoindole. Prepared as in example 101. HRMS (M+H)$^+$ for C$_{22}$H$_{26}$N$_5$O$_3$S, calc. 440.174611, found 440.175637.

EXAMPLE 203
Preparation of 3-(4-(2-aminosulfonylphenyl)pyridine-2-aminocarbonyl)methyl-5-amidinoindole 3-(4-(2-Aminosulfonylphenyl)pyridine-2-aminocarbonyl)methyl-5-cyanoindole. To a stirred solution of 5-cyano-3-acetic acid indole (400 mg, 2.0 mmol), BOP (884 mg, 3.0 mmol) in DMF (15 mL) was added 4-(2-aminosulfonyl)phenyl-2-aminopyridine (912 mg, 3.0 mmol) and heated at 50° C. for 3 h. The reaction was diluted with water, extracted with ethyl acetate, washed with 10% HCl, sodium bicarbonate, brine, and water, dried with magnesium sulfate, filtered and concentrated in vacuo to afford 420 mg of product. LRMS 488. The t-butyl group was removed in TFA reflux for 1 h and the product purified via silica gel using 100% ethyl acetate as the eluant to afford 101 mg of product. LRMS 432.

3-(4-(2-Aminosulfonylphenyl)pyridine-2-aminocarbonyl)methyl-5-amidinoindole. Prepared as in example 101. HRMS (M+H)$^+$ for C$_{22}$H$_{22}$N$_5$O$_3$S calc. 449.139586, found 449.139058.

EXAMPLE 204
Preparation of 3-(4-[2-tetrazole]phenyl) phenylaminocarbonyl)methyl-5-amidinoindole 3-(4-[2-Tetrazole]phenyl)phenylaminocarbonyl)methyl-5-cyanoindole. 5-cyanoindole-3-acetic acid was dissolved in DMF/CH$_2$Cl$_2$, DEC (382 mg), and DMAP (10 mg) and the reaction mixture stirred for 15 min. 4-((2-Tetrazole)phenyl) aniline was added and the reactin mixture stirred for 2 h. The reaction was concentrated in vacuo, dissolved in ethylacetate and washed with water and brine, dried with magnesium sulfate, filtered and concentrated in vacuo. Purification was done via silical gel using 1:1 hexanes:ethylacetate to afford 660 mg of product. The trityl group was cleaved in THF (30 mL) and 4 M HCl dioxane (0.988 mL) at rt for 18 h. It was then basified with NaOH to pH 11, washed with ether, acidified to pH 3 with 10% HCl and the precipitate was collected and dried under high vacuum to afford 250 mg of product. LRMS (M+H)$^+$ 420.

3-(4-[2-Tetrazole]phenyl)phenylaminocarbonyl)methyl-5-amidinoindole. Prepared as in example 101. HRMS for C$_{23}$H$_{20}$N$_8$O (M+H)$^+$ calc. 437.183833, found 437.186710.

EXAMPLE 205
Preparation of 3-(4-biphenylaminocarbonyl)methyl-5-amidinoindole

The title compound was prepared as in example 101. HRMS (M+H)$^+$ for C$_{23}$H$_{20}$N$_4$O calc. 369.172173, found 369.171537.

EXAMPLE 206
Preparation of 3-(4-(phenylmethylsulfonyl) piperazinecarbonyl)methyl-5-amidinoindole The title compound was prepared as in example 101. HRMS (M+H)+ $C_{22}H_{25}N_5O_3S$ calc. 440.176204, found 440.175637.

EXAMPLE 207
Preparation of 3-(4-cyclohexylphenylaminocarbonyl) methyl-5-amidinoindole The title compound was prepared as in example 101. HRMS (M+H)+ $C_{23}H_{26}N_4O$ calc. 375.218732. found 375.218487.

EXAMPLE 208
Preparation of 3-(4-benzylpiperazinecarbonyl)methyl-5-amidinoindole The title compound was prepared as in example 101. HRMS (M+H)+ for $C_{22}H_{25}N_5O$ calc. 376.213722, found 376.213736.

EXAMPLE 209
Preparation of 3-(3-amidinobenzylamino (methylcarbonylmethoxy)carbonyl)methyl-5-amidinoindole The title compound was prepared as in example 101. HRMS cal. 435.214464, found 435.216822.

EXAMPLE 210
Preparation of 1-methyl-3-(4-amidinobenzylamino (methylcarbonylmethoxy)carbonyl)methyl-5-amidinoindole The title compound was prepared as in example 101. HRMS calc.435.214464, found 435.213247.

EXAMPLE 211
Preparation of 1-methyl-3-(4-[2-aminosulfonyl] phenylbenzylaminocarbonyl)methyl-5-amidinoindole The title compound was prepared as in example 201. LRMS 476, m.p. 231° C.

EXAMPLE 212
Preparation of 1-methyl-3-(4-phenylbenzylaminocarbonyl)methyl-5-amidinoindole The title compound was prepared as in example 201. HRMS calc. 397.202837, found 397.204520.

EXAMPLE 213
Preparation of 1-methyl-3-(4-phenylpiperazinecarbonyl) methyl-5-amidinoindole The title compound was prepared as in example 201. HRMS calc. 389.234137, found 389.234635.

EXAMPLE 214
Preparation of 3-(4-[2-aminosulfonyl) phenylphenylaminocarbonyl)methyl-5-amidinoindole The title compound was prepared as in example 203. HRMS calc.448.144337 found 448.143656.

EXAMPLE 215
Preparation of 3-(1-benzylpiperidine-4-aminocarbonyl) methyl-5-amidinoindole The title compound was prepared as in example 201. HRMS calc. 390.229386, found 390.230305.

EXAMPLE 216
Preparation of 3-(4-phenylpiperazinecarbonyl)methyl-5-amidinoindole The title compound was prepared as in example 201. HRMS calc. 362.198086, found 362.197315.

EXAMPLE 217
Preparation of 3-(4-benzylpiperidinecarbonyl)methyl-5-amidinoindole The title compound was prepared as in example 201. HRMS calc. 374.210662 found 374.210386.

EXAMPLE 218
Preparation of 1-methyl-3-(5-(2-aminosulfonyl) phenylpyridine-2-aminocarbonyl)methyl-5-amidinoindole The title compound was prepared as in example 201. HRMS calc. 463.155236, found 463.155236.

EXAMPLE 219
Preparation of 3-(2-bromo-4-(2-aminosulfonyl) phenylphenylaminocarbonyl)methyl-5-cyanoindole A solution of 3-{2-bromo-4-(2-aminosulfonyl) phenylphenylaminocarbonyl)methyl-5-cyanoindoline (1.2378 mmol, 0.7 g) in anhydrous methyl acetate (15 mL) and anhydrous methanol (0.5 mL, 10.0 eq) was saturated with dry hydrogen chloride gas at −20° C. for 20 min. The reaction mixture was stoppered tightly and left at ambient temperature for 18 h. This reaction mixture was evaporated and pumped on for several hours to remove any residual HCl. To this imidate in anhydrous methanol (15 mL) was added ammonium carbonate (1.189 g, 10.0 eq.). This reaction mixture was allowed to stir at ambient temperature for 24 h. This final reaction mixture was evaporated and purified by HPLC on a C-18 column eluted with solvent mixture A (water:TFA 99.95:0.05) and solvent mixture B (acetonitrile:TFA 99.95:0.05) using a gradient starting with A at 80% and changing to B at 100% over 60 min. After lyophylization, 0.122 g of pure product (15%) was obtained; HRMS (M+H)+ calc. 526.054848, found 526.053791 for o-Br compound.

EXAMPLE 220
Preparation of 3-(2-methyl-4-(2-aminosulfonyl) phenylphenylaminocarbonyl)methyl-5-methylamino indole To the solution of 3-{2-methyl-4-(2-aminosulfonyl) phenylphenylaminocarbonyl)methyl-5-cyano indole (0.5992 mmol, 0.3 g) in absolute ethanol:TFA 4:6 was added palladium hydroxide on carbon (0.06 g, 20% weight equivalent of starting material used). This reaction mixture was stirred under house vacuum for 10 minutes at ambient temperature to remove oxygen. Then subjected to 1 atm $H_2$ via balloon method for 3 h. The reaction mixture was filtered through celite to remove catalyst and washed with ethanol (20 mL). The filtrate was evaporated to give the desired product with t-butyl sulfonamide. This product was treated with trifluoroacetic acid at 55° C. for 2 h for deprotection of sulfonamide. The reaction mixture was evaporated and purified by HPLC on a C-18 column eluted with solvent mixture A (water:TFA 99.95:0.05) and solvent mixture B (acetonitrile:TFA 99.95:0.05) using a gradient starting with A at 80% and changing to B at 100% over 60 min. to give 10.0 mg of pure product (3%, poor yield due to poor solubility); HRMS (M+H)+ calc. 449.164738, found 449.165207.

EXAMPLE 221
Preparation of 3-{2-fluoro-4-(2-aminosulfonyl) phenylphenylaminocarbonyl)methyl-5-amidinoindole The titled compound was prepared as in Example 203. HRMS (NH$_3$–Cl/DEP) (M+H)+ for $C_{23}H_{21}N_5SO_3F$ calculated 466.134915; found 466.133832.

EXAMPLE 222
Preparation of 3-{2-chloro-4-(2-aminosulfonyl) phenylphenylaminocarbonyl)methyl-5-cyanoindole The titled compound was prepared as in Example 203. HRMS for $C_{25}H_{21}N_5SO_3Cl$ (M+H)$^+$ calc. 482.105364; found 482.103835.

EXAMPLE 223
Preparation of 3-{2-iodo-4-(2-aminosulfonyl) phenylphenylaminocarbonyl)methyl-5-cyanoindole The titled compound was prepared as in Example 203. HRMS for $C_{23}H_{21}IN_5O_3S$ (M+H)$^+$ calc. 574.040989; found 574.042800.

EXAMPLE 224
Preparation of 3-{2-methyl-4-(2-aminosulfonyl) phenylphenylaminocarbonyl)methyl-5-amidinoindole The titled compound was prepared as in Example 203. HRMS for $C_{24}H_{24}N_5O_3S$ (M+H)$^+$ calc. 462.159987; found 462.158553.

EXAMPLE 225
Preparation of 3-{2-methyl-4-(2-(t-butylaminosulfonyl)) phenylphenylaminocarbonyl)methyl-5-amidinoindole The titled compound was prepared as in Example 203. HRMS for $C_{28}H_{32}N_5O_3S$ (M+H)$^+$ calc.518.222587; found 518.221998.

EXAMPLE 226
Preparation of 3-{4-(2-aminosulfonyl)phenyl) phenylaminocarbonylmethyl-α-(methylcarboxy methyl ether)-5-amidinoindole The titled compound (racemic) was prepared as in Example 203. HRMS for $C_{26}H_{25}N_5O_5S$ (M+H)$^+$ calc 520.166599; found 520.165466.

EXAMPLE 227
Preparation of 3-{4-(2-aminosulfonyl)phenyl) phenylaminocarbonylmethyl-α-(benzyl)-5-amidinoindole The titled compound (racemic) was prepared as in Example 203. HRMS for $C_{30}H_{29}N_5O_3S$ (M+H)$^+$ calc. 538.191287; found 538.191263.

EXAMPLE 228
Preparation of 3-{4-(2-trifluoromethyl)phenyl)pyrid-2-ylaminocarbonylmethyl-5-amidinoindole The titled compound was prepared as in Example 203. HRMS for $C_{23}H_{20}N_5O_1F_3$ (M+H)$^+$ 438.154170; found 438.152166.

EXAMPLE 229
Preparation of 3-{4-(2-ethylaminosulfonyl)phenyl) phenylaminocarbonylmethyl-5-amidinoindole The titled compound was prepared as in Example 203. HRMS for $C_{26}H_{27}N_5O_3S_1$ (M+H)$^+$ calc. 476.175637; found 476.175892.

EXAMPLE 230
Preparation of 3-{4-(2-propylaminosulfonyl)phenyl) phenyl}aminocarbonylmethyl-5-amidinoindole The titled compound was prepared as in Example 203. HRMS for $C_{26}H_{27}N_5O_3S$ (M+H)$^+$ calc. 490.191287; found 490.190996.

EXAMPLE 231
Preparation of 2-methyl-3-{2-iodo-4-(2-aminosulfonyl) phenyl)phenyl}aminocarbonylmethyl-5-amidinoindole The titled compound was prepared as in Example 203. HRMS for $C_{24}H_{23}IN_5O_3S_1$ (M+H)$^+$ calc. 558.056639; found 558.057057.

EXAMPLE 232
Preparation of 2-methyl-3-{4-(2-aminosulfonyl)phenyl) phenyl}aminocarbonylmethyl-5-amidinoindole The titled compound was prepared as in Example 203. LRMS for $C_{24}H_{23}N_5O_3S_1$ (M+H)$^+$ 462.

EXAMPLE 233
Preparation of 3-{4-(2-aminosulfonyl)phenyl)phenyl}-N-methylaminocarbonylmethyl-5-amidinoindole The titled compound was prepared as in Example 203. LRMS for $C_{24}H_{24}N_5O_3S_1$ (M+H)$^+$ 462.

EXAMPLE 234
Preparation of 2-methyl-3-{4-(2-t-butylaminosulfonyl) phenyl)phenyl}aminocarbonylmethyl-5-methoxyindole The titled compound was prepared as in Example 203. LRMS for $C_{28}H_{31}N_3O_4S_1$ (M+H)$^+$ 506.

EXAMPLE 235
Preparation of 3-{4-(2-N-methylaminosulfonyl)phenyl) phenyl}-N-methylaminocarbonylmethyl-5-amidinoindole The titled compound was prepared as in Example 203. HRMS for $C_{24}H_{23}N_5O_3S$ (M+H)$^+$ cacl. 462.159987; found 462.159054.

EXAMPLE 236
Preparation of 3-{4-(2-(n-butylaminosulfonyl) phenylphenylaminocarbonyl)methyl-5-cyanoindoline To a solution of 3-acetic acid indoline (0.001 mol, 0.2 g) [or indoline acid (0.001 mol, 0.202 g)] in anhydrous acetonitrile (10 mL) was added thionyl chloride (0.3 mL, 4.0 eq.) [for indoline, 1.0 M HCl in ethyl ether (0.05 mL, 1.0 eq.) was added before thionyl chloride]. This reaction mixture was warmed up at 50° C. for 10 min. then allowed to cool to ambient temperature and stirred for 2 h. The solvent and extra thionyl chloride were removed in vacuo and the residue was pumped on for several hours for further dry. To this dried residue was added a mixture of A-B (0.338 g, 1.0 eq.) and triethyl amine (0.14 mL, 1.0 eq.; 2.0 eq. for HCl salt) in anhydrous methylene chloride (10 mL). This reaction mixture was allowed to stir at ambient temperature for 2 h. The reaction mixture was evaporated and purified by flash chromatography on a silica gel column (50 g) eluted with 3:1 hexane:ethyl acetate to give 0.4 g of pure product with n-butyl sulfonamide (51%).

EXAMPLE 237
Preparation of 3-{4-(2-(n-propylaminosulfonyl) phenylphenylaminocarbonyl)methyl-5-amidinoindoline The titled compound was prepared as in Example 203. HRMS for $C_{26}H_{30}N_5SO_3$ (M+H)$^+$ calc. 492.206937; found 492.207667.

EXAMPLE 238
Preparation of (−)-3-{4-(2-aminosulfonyl)phenyl)pyrid-2-ylaminocarbonylmethyl-5-amidinoindoline The titled compound was prepared as in Example 203. HRMS for $C_{22}H_{24}N_6O_3S_1$ (M+H)$^+$ calc.451.155236; found 451.154317.

EXAMPLE 239
Preparation of 3-{4-(2-aminosulfonyl)phenyl)pyrid-2-ylaminocarbonylmethyl-5-amidinoindoline The titled compound (racemic) was prepared as in Example 203. HRMS for $C_{22}H_{24}N_6O_3S_1$ (M+H)$^+$ calc. 451.155236; found 451.154317.

EXAMPLE 240
Preparation of 3-{4-(2-dimethylaminosulfonyl)phenyl) phenylaminocarbonylmethyl-5-amidinoindoline The titled compound (racemic) was prepared as in Example 203. HRMS for $C_{25}H_{26}N_5O_3S_1$ (M+H)$^+$ calc. 450.159987; found 450.159435.

EXAMPLE 241

Preparation of (+)-3-{4-(2-t-butylaminosulfonyl)phenyl)pyrid-2-ylaminocarbonylmethyl-5-amidinoindoline The titled compound was prepared as in Example 203. HRMS for $C_{26}H_{30}N_6O_3S_1$ (M+H)$^+$ calc. 507.217836; found 507.217901. 98%ee; rotation (+) 19.23.

EXAMPLE 242

Preparation of (−)-3-{4-(2-t-butylaminosulfonyl)phenyl)pyrid-2-ylaminocarbonylmethyl-5-amidinoindoline The titled compound was prepared as in Example 203. HRMS for $C_{26}H_{30}N_6O_3S_1$ (M+H)$^+$ calc.507.217836; found 507.217678. 98%ee; rotaion −16.28.

EXAMPLE 243

Preparation of 3-{4-(2-aminosulfonyl)phenyl)pyrid-2-yl)aminocarbonylmethyl-5-aminocarboxyindoline The titled compound (racemic) was prepared as in Example 203. HRMS for $C_{22}H_{23}N_6O_3S_1$ (M+H)$^+$ calc. 451.1552036; found 451.154691.

EXAMPLE 244

Preparation of 3-{4-(2-t-butylaminosulfonyl)phenyl)phenyl}aminocarbonylmethyl-5-amidinoindoline The titled compound was prepared as in Example 203. LRMS for $C_{27}H_{31}N_5O_3S_1$ (M+H)$^+$ calc.506.3; found 506.4.

EXAMPLE 245

Preparation of 3-{4-(2-t-butylaminosulfonyl)phenyl)pyrid-2-yl}aminocarbonylmethyl-5-amidinoindoline The titled compound (racemic) was prepared as in Example 203. LRMS for $C_{26}H_{30}N_6O_3S_1$ (M+H)$^+$ calc.507.3; found 507.4.

EXAMPLE 246

Preparation of 3-{4-(2-aminosulfonyl)phenyl)pyrid-2-ylaminocarbonylmethyl-6-amidinoindazole The titled compound was prepared as in Example 203. HRMS for $C_{21}H_{21}N_7O_3S_1$ (M+H)$^+$ calc. 450.134835; found 450.134725.

EXAMPLE 247

Preparation of 3-{4-(2-aminosulfonyl)phenyl)phenyl aminocarbonylmethyl-6-amidinoindazole The titled compound was prepared as in Example 203. HRMS for $C_{22}H_{22}N_6O_3S_1$ (M+H)$^+$ calc. 449.139586; found 449.138515.

EXAMPLE 248

Preparation of 3-{4-(2-t-butyl aminosulfonyl)phenyl)pyrid-2-ylaminocarbonylmethyl-6-amidinoindazole The titled compound was prepared as in Example 203. HRMS for $C_{25}H_{29}N_7O_3S_1$ (M+H)$^+$ calc.450.134835; 450.134725

EXAMPLE 249

Preparation of 3-{4-(2-t-butylaminosulfonyl)phenyl)phenyl aminocarbonylmethyl-6-amidinoindazole The titled compound was prepared as in Example 203. HRMS for $C_{26}H_{30}N_6O_3S_1$ (M+H)$^+$ calc.505.202186; found 505.202631.

TABLE 5

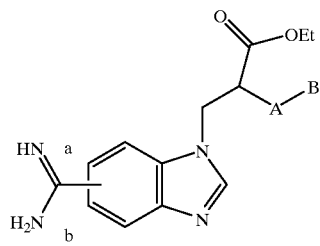

| Ex | Am. Pos. | A | B | MS (100%) or HRMS |
|---|---|---|---|---|
| 1 | a + b | phenethyl | 3-amidino | 204(M+2H)$^{2+}$ |
| 2 | b | phenethyl | 3-amidino | 204.2(M+2H)$^{2+}$ |
| 3 | a | phenethyl | 3-amidino | 204.2(M+2H)$^{2+}$ |
| 4 | a + b | phenethyl | 4-amidino | 407.2200 |
| 5 | b | phenethyl | 4-amidino | 204(M+2H)$^{2+}$ |
| 6 | a | phenethyl | 4-amidino | 204(M+2H)$^{2+}$ |
| 7 | a + b | phenyl-CH= | 4-amidino | 196.2(M+2H)$^{2+}$ |
| 8 | a + b | phenyl | 4-amidino | 197(M+2H)$^{2+}$ |

TABLE 6a

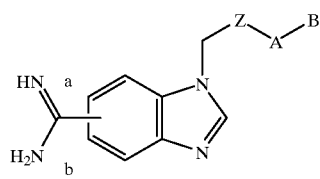

| Ex | Am. Pos. | Z | A | B | MS (100%) or HRMS |
|---|---|---|---|---|---|
| 51 | a | C(O) | phenyl | 4-phenyl | 355.1554 |
| 52 | b | C(O) | phenyl | 4-phenyl | 355.1559 |
| 53 | a | C(O) | phenyl | 4-(3-NH$_2$)phenyl | 370 (M+H)$^+$ |
| 54 | b | C(O) | phenyl | 4-(3-NH$_2$)phenyl | 370 (M+H)$^+$ |
| 55 | a | C(O) | phenyl | 4-(4-F)phenyl | 373.1481 |
| 56 | a | C(O) | phenyl | 4-(4-CHO)phenyl | 383.1531 |
| 57 | a | C(O) | phenyl | 4-(2-NH$_2$SO$_2$)phenyl | 434.1303 |
| 58 | a | C(O) | phenyl | 4-(2-tBuNHSO$_2$)phenyl | |
| 59 | a | C(O) | phenyl | 4-(2-tetrazolyl)phenyl | 423.1686 |
| 60 | a | C(O)NH | phenyl | 4-(2-NH$_2$SO$_2$)phenyl | 449.1414 |
| 61 | b | C(O)NH | phenyl | 4-(2-NH$_2$SO$_2$)phenyl | 449.1401 |
| 62 | a + b | C(O) | 1-piperidine | 4-benzyl | 376.2118 |
| 63 | b | C(O) | 1-piperidine | 4-benzyl | 376.2130 |
| 64 | a | C(O) | phenyl | 4-(2-NH$_2$SO$_2$)phenyl | 449.1393 |
| 65* | 6-aza | C(O) | phenyl | 4-(2-tBuNHSO$_2$)phenyl | 436 |

*Ex. 65 contains the CH$_2$-Z-A-B group at the 2-position.

TABLE 6b

| Ex | Z' | A | B | HRMS |
|---|---|---|---|---|
| 65* | CH$_2$C(O) | phenyl | 4-(2-tBuNHSO$_2$)phenyl | 464.1756 |
| 66 | SCH$_2$C(O)NH | phenyl | 4-(2-tBuNHSO$_2$)phenyl | 496.1477 |
| 67 | SCH$_2$C(O)NH | phenyl | 4-(2-NH$_2$SO$_2$)phenyl | 440.0831 |

TABLE 7

| Ex | R$^1$ | Z' | A | B | MS or HRMS |
|---|---|---|---|---|---|
| 101 | H | C(O) | 1-piperidine | 4-benzyl | 375.218 |
| 102 | H | CH$_2$C(O) | 1-piperidine | 4-benzyl | 389.231 |
| 103 | H | C(O) | 1-piperidine | 4-(3-F)benzyl | 393.209 |
| 104 | H | C(O)N(CH$_2$CO$_2$CH$_3$) | benzyl | 4-amidino | 218 |
| 105 | CH$_2$—CO$_2$Me | C(O) | 1-piperidine | 4-benzyl | 447.242 |
| 106 | CH$_2$—CH$_2$OH | C(O) | 1-piperidine | 4-benzyl | 419.245 |
| 107 | CH$_2$—CO$_2$H | C(O) | 1-piperidine | 4-benzyl | 433 |
| 108 | H | C(O)NH | 4-piperidine | 1-benzyl | 390.229 |
| 109 | H | C(O) | 1-piperidine | 4-benzoyl | 389.198 |
| 110 | H | C(O) | 1-piperazinyl | 4-(3-F)benzyl | 394.205 |
| 111 | H | C(O)NH | benzyl | 4-phenyl | 383.190 |
| 112 | CH=CH—CO$_2$Me | C(O) | piperidine | 4-benzyl | 459 |
| 113 | H | C(O) | piperidine | 4-(2-F)benzyl | 393.209 |

TABLE 8a*

| Ex | C | R$^1$ | Z | A | B | MS or HRMS |
|---|---|---|---|---|---|---|
| 201 | Am | H | C(O)—CH$_2$NH | phenyl | 4-cyclohexyl | 389.232 |
| 202 | Am | H | C(O) | 1-piperazinyl | 4-p-toluene-sulfonyl | 440.176 |
| 203 | Am | H | C(O)NH | 2-pyridyl | 4-(2-aminosulfonyl)phenyl | 449.139 |
| 204 | Am | H | C(O)NH | 1-phenyl | 4-(2-tetrazol-5-yl)phenyl | 437.187 |
| 205 | Am | H | C(O)NH | 1-phenyl | 4-phenyl | 369.171 |
| 206 | Am | H | C(O) | 1-piperazinyl | 4-phenyl-methylsulfonyl | 440.176 |
| 207 | Am | H | C(O)NH | 1-phenyl | 4-cyclohexyl | 375.218 |
| 208 | Am | H | C(O) | 1-piperazinyl | 4-benzyl | 376.214 |
| 209 | Am | Me | C(O)N—(CH$_2$CO$_2$CH$_3$) | benzyl | 3-amidino | 435.217 |
| 210 | Am | Me | C(O)N—(CH$_2$CO$_2$CH$_3$) | benzyl | 4-amidino | 435.213 |
| 211 | Am | Me | C(O)NH | benzyl | 4-(2-aminosulfonyl)phenyl | 476 |
| 212 | Am | Me | C(O)NH | benzyl | 4-phenyl | 397.205 |
| 213 | Am | Me | C(O)CH$_2$ | 1-piperazinyl | 4-benzyl | 389.235 |
| 214 | Am | H | C(O)NH | phenyl | 4-(2-aminosulfonyl)phenyl | 448.144 |
| 215 | Am | H | C(O) | 4-piperidinyl | 1-benzyl | 390.230 |
| 216 | Am | H | C(O) | 1-piperazinyl | 4-phenyl | 362.197 |
| 217 | Am | H | C(O) | 1-piperidinyl | 4-benzyl | 374.210 |
| 218 | Am | Me | C(O)NH | 2-pyridyl | 5-(2-aminosulfonyl)phenyl | 463.155 |
| 219 | CN | H | C(O)NH | 2-Br-phenyl | 4-(2-aminosulfonyl)phenyl | 526.054 |
| 220 | CH$_3$—NH | H | C(O)NH | 2-Me-phenyl | 4-(2-aminosulfonyl)phenyl | 449.164 |
| 221 | Am | H | C(O)NH | 2-F-phenyl | 4-(2-aminosulfonyl)phenyl | 466.134 |
| 222 | CN | H | C(O)NH | 2-Cl-phenyl | 4-(2-aminosulfonyl)phenyl | 482.104 |
| 223 | CN | H | C(O)NH | 2-I-phenyl | 4-(2-aminosulfonyl)phenyl | 574.043 |
| 224 | Am | H | C(O)NH | 2-Me-phenyl | 4-(2-aminosulfonyl)phenyl | 462.156 |
| 225 | Am | H | C(O)NH | 2-Me-phenyl | 4-(2-t-Bu-aminosulfonyl)phenyl | 518.222 |
| 226 | Am | H | (CH$_3$O—C(O)—CH$_2$)CH | phenyl | 4-(2-aminosulfonyl)phenyl | 520.165 |
| 227 | Am | H | (phenyl-CH$_2$)CH | phenyl | 4-(2-aminosulfonyl)phenyl | 538.191 |
| 228 | Am | H | C(O)NH | 2-pyridyl | 4-(2-CF$_3$-phenyl) | 438.152 |

TABLE 8a*-continued

[Structure: indole with R¹ on N, (Z)ₙ-A-B at 3-position, D at 5-position]

| Ex | C | R¹ | Z | A | B | MS or HRMS |
|---|---|---|---|---|---|---|
| 229 | Am | H | C(O)NH | phenyl | 4-(2-ethylamino-sulfonyl)phenyl | 476.176 |
| 230 | Am | H | C(O)NH | phenyl | 4-(2-propylamino-sulfonyl)phenyl | 490.191 |
| 231 | Am | H | C(O)NH (R¹=2-methyl) | 2-I-phenyl | 4-(2-aminosulfonyl)phenyl | 558.057 |
| 232 | Am | H | C(O)NH (R¹=2-methyl) | phenyl | 4-(2-aminosulfonyl)phenyl | 462 |
| 233 | Am | H | C(O)—NCH₃ | phenyl | 4-(2-aminosulfonyl)phenyl | 462 |
| 234 | CH₃O | H | C(O)NH (R¹=2-methyl) | phenyl | 4-(2-t-Bu-aminosulfonyl)phenyl | 506 |
| 235 | Am | H | C(O)—NCH₃ | phenyl | 4-(2-methylamino-sulfonyl)phenyl | 462.160 |

*For all Examples, but 226 and 277, n = 1. For Examples 226 and 227, n = 0.

TABLE 8b

[Structure: indoline with R¹ on N, Z-A-B at 3-position, D at 5-position]

| Ex | D | R¹ | Z | A | B | MS or HRMS |
|---|---|---|---|---|---|---|
| 236 | CN | H | C(O)NH | phenyl | 4-(2-n-Bu-aminosulfonyl)phenyl | |
| 237 | Am | H | C(O)NH | phenyl | 4-(2-propyl-amino-sulfonyl)phenyl | 492.208 |
| 238 (−) | Am | H | C(O)NH | 2-pyridyl | 4-(2-amino-sulfonyl)phenyl | 451.154 |
| 239 | Am | H | C(O)NH | 2-pyridyl | 4-(2-amino-sulfonyl)phenyl | 451.155 |
| 240 | Am | H | C(O)NH | phenyl | 4-(2-N,N-dimethylamino-sulfonyl)phenyl | 450.160 |
| 241 (+) | Am | H | C(O)NH | 2-pyridyl | 4-(2-t-Bu-aminosulfonyl)phenyl | 507.218 |
| 242 (−) | Am | H | C(O)NH | 2-pyridyl | 4-(2-t-Bu-aminosulfonyl)phenyl | 507.218 |
| 243 | NH₂—C(O) | H | C(O)NH | 2-pyridyl | 4-(2-amino-sulfonyl)phenyl | 451.154 |
| 244 | Am | H | C(O)NH | phenyl | 4-(2-t-Bu-amino-sulfonyl)phenyl | 506.4 |

TABLE 8b-continued

| Ex | D | R¹ | Z | A | B | MS or HRMS |
|---|---|---|---|---|---|---|
| 245 | Am | H | C(O)NH | 2-pyridyl | 4-(2-t-Bu-amino-sulfonyl)phenyl | 507.4 |

TABLE 8c

[Structure: indazole with R¹ on N, Z-A-B at 3-position, D at 6-position]

| Ex | D | R¹ | Z | A | B | MS or HRMS |
|---|---|---|---|---|---|---|
| 246 | Am | H | C(O)NH | 2-pyridyl | 4-(2-aminosulfonyl)phenyl | 450.135 |
| 247 | Am | H | C(O)NH | phenyl | 4-(2-aminosulfonyl)phenyl | 449.139 |
| 248 | Am | H | C(O)NH | 2-pyridyl | 4-(2-t-Bu-amino-sulfonyl)phenyl | 450.135 |
| 249 | Am | H | C(O)NH | phenyl | 4-(2-t-Bu-amino-sulfonyl)phenyl | 505.203 |

TABLE 9

[Structure: 6-amidino-indole with (Z)ₙ-A-B on N1]

| Ex | n | Z | A-B |
|---|---|---|---|
| 301 | 1 | C(O) | 4-(2-aminosulfonylphenyl)phenyl |
| 302 | 1 | C(O) | 4-(2-aminosulfonylphenyl)-2-pyridyl |
| 303 | 1 | C(O) | 4-(2-methylaminosulfonyl-phenyl)phenyl |
| 304 | 1 | C(O) | 4-(2-ethylaminosulfonyl-phenyl)-2-pyridyl |
| 305 | 1 | C(O) | 2-aminosulfonyl-4-cyclohexylphenyl |
| 306 | 1 | C(O) | 3-aminosulfonyl-4-t-butyl-2-pyridyl |
| 307 | 1 | C(O) | 2-(5-indazol-5-yl)furanyl |
| 308 | 1 | C(O) | 2-(5-indazol-6-yl)thienyl |
| 309 | 1 | C(O) | 4-(2-tetrazolylphenyl)phenyl |
| 310 | 1 | C(O)NH | 4-(2-aminosulfonylphenyl)phenyl |

TABLE 9-continued

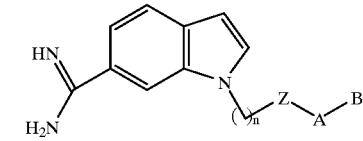

| Ex | n | Z | A-B |
|---|---|---|---|
| 311 | 1 | C(O)NH | 4-(2-aminosulfonylphenyl)-2-pyridyl |
| 312 | 1 | C(O)NH | 4-(2-methylaminosulfonyl-phenyl)phenyl |
| 313 | 1 | C(O)NH | 4-(2-ethylaminosulfonyl-phenyl)-2-pyridyl |
| 314 | 1 | C(O)NH | 2-aminosulfonyl-4-cyclohexylphenyl |
| 315 | 1 | C(O)NH | 3-aminosulfonyl-4-t-butyl-2-pyridyl |
| 316 | 1 | C(O)NH | 2-(5-indazol-5-yl)furanyl |
| 317 | 1 | C(O)NH | 2-(5-indazol-6-yl)thienyl |
| 318 | 1 | C(O)NH | 4-(2-tetrazolylphenyl)phenyl |
| 319 | 1 | NHC(O) | 4-(2-aminosulfonylphenyl)phenyl |
| 320 | 1 | NHC(O) | 4-(2-aminosulfonylphenyl)-2-pyridyl |
| 321 | 1 | NHC(O) | 4-(2-methylaminosulfonyl-phenyl)phenyl |
| 322 | 1 | NHC(O) | 4-(2-ethylaminosulfonyl-phenyl)-2-pyridyl |
| 323 | 1 | NHC(O) | 2-aminosulfonyl-4-cyclohexylphenyl |
| 324 | 1 | NHC(O) | 3-aminosulfonyl-4-t-butyl-2-pyridyl |
| 325 | 1 | NHC(O) | 2-(5-indazol-5-yl)furanyl |
| 326 | 1 | NHC(O) | 2-(5-indazol-6-yl)thienyl |
| 327 | 1 | NHC(O) | 4-(2-tetrazolylphenyl)phenyl |
| 328 | 1 | SO$_2$NH | 4-(2-aminosulfonylphenyl)phenyl |
| 329 | 1 | SO$_2$NH | 4-(2-aminosulfonylphenyl)-2-pyridyl |
| 330 | 1 | SO$_2$NH | 4-(2-methylaminosulfonyl-phenyl)phenyl |
| 331 | 1 | SO$_2$NH | 4-(2-ethylaminosulfonyl-phenyl)-2-pyridyl |
| 332 | 1 | SO$_2$NH | 2-aminosulfonyl-4-cyclohexylphenyl |
| 333 | 1 | SO$_2$NH | 3-aminosulfonyl-4-t-butyl-2-pyridyl |
| 334 | 1 | SO$_2$NH | 2-(5-indazol-5-yl)furanyl |
| 335 | 1 | SO$_2$NH | 2-(5-indazol-6-yl)thienyl |
| 336 | 1 | SO$_2$NH | 4-(2-tetrazolylphenyl)phenyl |
| 337 | 0 | CH(CH$_2$CH$_2$OH)C(O)NH | 4-(2-aminosulfonylphenyl)phenyl |
| 338 | 0 | CH(CH$_2$CH$_2$OH)C(O)NH | 4-(2-aminosulfonylphenyl)-2-pyridyl |
| 339 | 0 | CH(CH$_2$CH$_2$OH)C(O)NH | 4-(2-methylaminosulfonyl-phenyl)phenyl |
| 340 | 0 | CH(CH$_2$CH$_2$OH)C(O)NH | 4-(2-ethylaminosulfonyl-phenyl)-2-pyridyl |
| 341 | 0 | CH(CH$_2$CH$_2$OH)C(O)NH | 2-aminosulfonyl-4-cyclohexylphenyl |
| 342 | 0 | CH(CH$_2$CH$_2$OH)C(O)NH | 3-aminosulfonyl-4-t-butyl-2-pyridyl |
| 343 | 0 | CH(CH$_2$CH$_2$OH)C(O)NH | 2-(5-indazol-5-yl)furanyl |
| 344 | 0 | CH(CH$_2$CH$_2$OH)C(O)NH | 2-(5-indazol-6-yl)thienyl |
| 345 | 0 | CH(CH$_2$CH$_2$OH)C(O)NH | 4-(2-tetrazolylphenyl)phenyl |
| 346 | 0 | CH(CH$_2$-tetrazolyl)C(O)NH | 4-(2-aminosulfonylphenyl)phenyl |
| 347 | 0 | CH(CH$_2$-tetrazolyl)C(O)NH | 4-(2-aminosulfonylphenyl)-2-pyridyl |
| 348 | 0 | CH(CH$_2$-tetrazolyl)C(O)NH | 4-(2-methylaminosulfonyl-phenyl)phenyl |
| 349 | 0 | CH(CH$_2$-tetrazolyl)C(O)NH | 4-(2-ethylaminosulfonyl-phenyl)-2-pyridyl |
| 350 | 0 | CH(CH$_2$-tetrazolyl)C(O)NH | 2-aminosulfonyl-4-cyclohexylphenyl |
| 351 | 0 | CH(CH$_2$-tetrazolyl)C(O)NH | 3-aminosulfonyl-4-t-butyl-2-pyridyl |
| 352 | 0 | CH(CH$_2$-tetrazolyl)C(O)NH | 2-(5-indazol-5-yl)furanyl |
| 353 | 0 | CH(CH$_2$-tetrazolyl)C(O)NH | 2-(5-indazol-6-yl)thienyl |
| 354 | 0 | CH(CH$_2$-tetrazolyl)C(O)NH | 4-(2-tetrazolylphenyl)phenyl |

TABLE 10

| Ex | n | Z | A-B |
|---|---|---|---|
| 401 | 1 | C(O) | 4-(2-aminosulfonylphenyl)phenyl |
| 402 | 1 | C(O) | 4-(2-aminosulfonylphenyl)-2-pyridyl |
| 403 | 1 | C(O) | 4-(2-methylaminosulfonyl-phenyl)phenyl |
| 404 | 1 | C(O) | 4-(2-ethylaminosulfonyl-phenyl)-2-pyridyl |
| 405 | 1 | C(O) | 2-aminosulfonyl-4-cyclohexylphenyl |
| 406 | 1 | C(O) | 3-aminosulfonyl-4-t-butyl-2-pyridyl |
| 407 | 1 | C(O) | 2-(5-indazol-5-yl)furanyl |
| 408 | 1 | C(O) | 2-(5-indazol-6-yl)thienyl |
| 409 | 1 | C(O) | 4-(2-tetrazolylphenyl)phenyl |
| 410 | 1 | C(O)NH | 4-(2-aminosulfonylphenyl)phenyl |
| 411 | 1 | C(O)NH | 4-(2-aminosulfonylphenyl)-2-pyridyl |
| 412 | 1 | C(O)NH | 4-(2-methylaminosulfonyl-phenyl)phenyl |
| 413 | 1 | C(O)NH | 4-(2-ethylaminosulfonyl-phenyl)-2-pyridyl |
| 414 | 1 | C(O)NH | 2-aminosulfonyl-4-cyclohexylphenyl |
| 415 | 1 | C(O)NH | 3-aminosulfonyl-4-t-butyl-2-pyridyl |
| 416 | 1 | C(O)NH | 2-(5-indazol-5-yl)furanyl |
| 417 | 1 | C(O)NH | 2-(5-indazol-6-yl)thienyl |
| 418 | 1 | C(O)NH | 4-(2-tetrazolylphenyl)phenyl |
| 419 | 1 | NHC(O) | 4-(2-aminosulfonylphenyl)phenyl |
| 420 | 1 | NHC(O) | 4-(2-aminosulfonylphenyl)-2-pyridyl |
| 421 | 1 | NHC(O) | 4-(2-methylaminosulfonyl-phenyl)phenyl |
| 422 | 1 | NHC(O) | 4-(2-ethylaminosulfonyl-phenyl)-2-pyridyl |
| 423 | 1 | NHC(O) | 2-aminosulfonyl-4-cyclohexylphenyl |
| 424 | 1 | NHC(O) | 3-aminosulfonyl-4-t-butyl-2-pyridyl |
| 425 | 1 | NHC(O) | 2-(5-indazol-5-yl)furanyl |
| 426 | 1 | NHC(O) | 2-(5-indazol-6-yl)thienyl |
| 427 | 1 | NHC(O) | 4-(2-tetrazolylphenyl)phenyl |

TABLE 10-continued

Structure: indole with HN=C(NH2)- at position 6, and N1 substituted with -(CH2)n-Z-CH2-A-B

| Ex | n | Z | A-B |
|---|---|---|---|
| 428 | 1 | SO₂NH | 4-(2-aminosulfonylphenyl)phenyl |
| 429 | 1 | SO₂NH | 4-(2-aminosulfonylphenyl)-2-pyridyl |
| 430 | 1 | SO₂NH | 4-(2-methylaminosulfonyl-phenyl)phenyl |
| 431 | 1 | SO₂NH | 4-(2-ethylaminosulfonyl-phenyl)-2-pyridyl |
| 432 | 1 | SO₂NH | 2-aminosulfonyl-4-cyclohexylphenyl |
| 433 | 1 | SO₂NH | 3-aminosulfonyl-4-t-butyl-2-pyridyl |
| 434 | 1 | SO₂NH | 2-(5-indazol-5-yl)furanyl |
| 435 | 1 | SO₂NH | 2-(5-indazol-6-yl)thienyl |
| 436 | 1 | SO₂NH | 4-(2-tetrazolylphenyl)phenyl |
| 437 | 0 | CH(CH₂CH₂OH)C(O)NH | 4-(2-aminosulfonylphenyl)phenyl |
| 438 | 0 | CH(CH₂CH₂OH)C(O)NH | 4-(2-aminosulfonylphenyl)-2-pyridyl |
| 439 | 0 | CH(CH₂CH₂OH)C(O)NH | 4-(2-methylaminosulfonyl-phenyl)phenyl |
| 440 | 0 | CH(CH₂CH₂OH)C(O)NH | 4-(2-ethylaminosulfonyl-phenyl)-2-pyridyl |
| 441 | 0 | CH(CH₂CH₂OH)C(O)NH | 2-aminosulfonyl-4-cyclohexylphenyl |
| 442 | 0 | CH(CH₂CH₂OH)C(O)NH | 3-aminosulfonyl-4-t-butyl-2-pyridyl |
| 443 | 0 | CH(CH₂CH₂OH)C(O)NH | 2-(5-indazol-5-1)furanyl |
| 444 | 0 | CH(CH₂CH₂OH)C(O)NH | 2-(5-indazol-6-yl)thienyl |
| 445 | 0 | CH(CH₂CH₂OH)C(O)NH | 4-(2-tetrazolylphenyl)phenyl |
| 446 | 0 | CH(CH₂-tetrazolyl)C(O)NH | 4-(2-aminosulfonylphenyl)phenyl |
| 447 | 0 | CH(CH₂-tetrazolyl)C(O)NH | 4-(2-aminosulfonylphenyl)-2-pyridyl |
| 448 | 0 | CH(CH₂-tetrazolyl)C(O)NH | 4-(2-methylaminosulfonyl-phenyl)phenyl |
| 449 | 0 | CH(CH₂-tetrazolyl)C(O)NH | 4-(2-ethylaminosulfonyl-phenyl)-2-pyridyl |
| 450 | 0 | CH(CH₂-tetrazolyl)C(O)NH | 2-aminosulfonyl-4-cyclohexylphenyl |
| 451 | 0 | CH(CH₂-tetrazolyl)C(O)NH | 3-aminosulfonyl-4-t-butyl-2-pyridyl |
| 452 | 0 | CH(CH₂-tetrazolyl)C(O)NH | 2-(5-indazol-5-yl)furanyl |
| 453 | 0 | CH(CH₂-tetrazolyl)C(O)NH | 2-(5-indazol-6-yl)thienyl |
| 454 | 0 | CH(CH₂-tetrazolyl)C(O)NH | 4-(2-tetrazolylphenyl)phenyl |

TABLE 11

Structure: benzimidazole with HN=C(NH2)- at position 6, and N1 substituted with -(CH2)n-Z-CH2-A-B

| Ex | n | Z | A—B |
|---|---|---|---|
| 501 | 1 | C(O) | 4-(2-aminosulfonylphenyl)-2-pyridyl |
| 502 | 1 | C(O) | 4-(2-methylaminosulfonyl-phenyl)phenyl |
| 503 | 1 | C(O) | 4-(2-ethylaminosulfonyl-phenyl)-2-pyridyl |
| 504 | 1 | C(O) | 2-aminosulfonyl-4-cyclohexylphenyl |
| 505 | 1 | C(O) | 3-aminosulfonyl-4-t-butyl-2-pyridyl |
| 506 | 1 | C(O) | 2-(5-indazol-5-yl)furanyl |
| 507 | 1 | C(O) | 2-(5-indazol-6-yl)thienyl |
| 508 | 1 | C(O) | 4-(2-tetrazolylphenyl)phenyl |
| 509 | 1 | C(O)NH | 4-(2-aminosulfonylphenyl)-2-pyridyl |
| 510 | 1 | C(O)NH | 4-(2-methylaminosulfonyl-phenyl)phenyl |
| 511 | 1 | C(O)NH | 4-(2-ethylaminosulfonyl-phenyl)-2-pyridyl |
| 512 | 1 | C(O)NH | 2-aminosulfonyl-4-cyclohexylphenyl |
| 513 | 1 | C(O)NH | 3-aminosulfonyl-4-t-butyl-2-pyridyl |
| 514 | 1 | C(O)NH | 2-(5-indazol-5-yl)furanyl |
| 515 | 1 | C(O)NH | 2-(5-indazol-6-yl)thienyl |
| 516 | 1 | C(O)NH | 4-(2-tetrazolylphenyl)phenyl |
| 517 | 1 | NHC(O) | 4-(2-aminosulfonylphenyl)phenyl |
| 518 | 1 | NHC(O) | 4-(2-aminosulfonylphenyl)-2-pyridyl |
| 519 | 1 | NHC(O) | 4-(2-methylaminosulfonyl-phenyl)phenyl |
| 520 | 1 | NHC(O) | 4-(2-ethylaminosulfonyl-phenyl)-2-pyridyl |
| 521 | 1 | NHC(O) | 2-aminosulfonyl-4-cyclohexylphenyl |
| 522 | 1 | NHC(O) | 3-aminosulfonyl-4-t-butyl-2-pyridyl |
| 523 | 1 | NHC(O) | 2-(5-indazol-5-yl)furanyl |
| 524 | 1 | NHC(O) | 2-(5-indazol-6-yl)thienyl |
| 525 | 1 | NHC(O) | 4-(2-tetrazolylphenyl)phenyl |
| 526 | 1 | SO₂NH | 4-(2-aminosulfonylphenyl)phenyl |
| 527 | 1 | SO₂NH | 4-(2-aminosulfonylphenyl)-2-pyridyl |
| 528 | 1 | SO₂NH | 4-(2-methylaminosulfonyl-phenyl)phenyl |
| 529 | 1 | SO₂NH | 4-(2-ethylaminosulfonyl-phenyl)-2-pyridyl |
| 530 | 1 | SO₂NH | 2-aminosulfonyl-4-cyclohexylphenyl |
| 531 | 1 | SO₂NH | 3-aminosulfonyl-4-t-butyl-2-pyridyl |
| 532 | 1 | SO₂NH | 2-(5-indazol-5-yl)furanyl |
| 533 | 1 | SO₂NH | 2-(5-indazol-6-yl)thienyl |
| 534 | 1 | SO₂NH | 4-(2-tetrazolylphenyl)phenyl |
| 535 | 0 | CH(CH₂CH₂OH)C(O)NH | 4-(2-aminosulfonylphenyl)phenyl |
| 536 | 0 | CH(CH₂CH₂OH)C(O)NH | 4-(2-aminosulfonylphenyl)-2-pyridyl |
| 537 | 0 | CH(CH₂CH₂OH)C(O)NH | 4-(2-methylaminosulfonyl-phenyl)phenyl |
| 538 | 0 | CH(CH₂CH₂OH)C(O)NH | 4-(2-ethylaminosulfonyl-phenyl)-2-pyridyl |
| 539 | 0 | CH(CH₂CH₂OH)C(O)NH | 2-aminosulfonyl-4-cyclohexylphenyl |
| 540 | 0 | CH(CH₂CH₂OH)C(O)NH | 3-aminosulfonyl-4-t-butyl-2-pyridyl |
| 541 | 0 | CH(CH₂CH₂OH)C(O)NH | 2-(5-indazol-5-yl)furanyl |

TABLE 11-continued

Structure: benzimidazole with HN=C(NH2)- at 6-position, N1-(CH2)n-Z-A-B

| Ex | n | Z | A—B |
|---|---|---|---|
| 542 | 0 | CH(CH₂CH₂OH)C(O)NH | 2-(5-indazol-6-yl)thienyl |
| 543 | 0 | CH(CH₂CH₂OH)C(O)NH | 4-(2-tetrazolylphenyl)phenyl |
| 544 | 0 | CH(CH₂-tetrazolyl)C(O)NH | 4-(2-aminosulfonylphenyl)phenyl |
| 545 | 0 | CH(CH₂-tetrazolyl)C(O)NH | 4-(2-aminosulfonylphenyl)-2-pyridyl |
| 546 | 0 | CH(CH₂-tetrazolyl)C(O)NH | 4-(2-methylaminosulfonyl-phenyl)phenyl |
| 547 | 0 | CH(CH₂-tetrazolyl)C(O)NH | 4-(2-ethylaminosulfonyl-phenyl)-2-pyridyl |
| 548 | 0 | CH(CH₂-tetrazolyl)C(O)NH | 2-aminosulfonyl-4-cyclohexylphenyl |
| 549 | 0 | CH(CH₂-tetrazolyl)C(O)NH | 3-aminosulfonyl-4-t-butyl-2-pyridyl |
| 550 | 0 | CH(CH₂-tetrazolyl)C(O)NH | 2-(5-indazol-5-yl)furanyl |
| 551 | 0 | CH(CH₂-tetrazolyl)C(O)NH | 2-(5-indazol-6-yl)thienyl |
| 552 | 0 | CH(CH₂-tetrazolyl)C(O)NH | 4-(2-tetrazolylphenyl)phenyl |

TABLE 12

Structure: indazole with HN=C(NH2)- at 6-position, N1-(CH2)n-Z-A-B

| Ex | n | Z | A—B |
|---|---|---|---|
| 601 | 1 | C(O) | 4-(2-aminosulfonylphenyl)phenyl |
| 602 | 1 | C(O) | 4-(2-aminosulfonylphenyl)-2-pyridyl |
| 603 | 1 | C(O) | 4-(2-methylaminosulfonyl-phenyl)phenyl |
| 604 | 1 | C(O) | 4-(2-ethylaminosulfonyl-phenyl)-2-pyridyl |
| 605 | 1 | C(O) | 2-aminosulfonyl-4-cyclohexylphenyl |
| 606 | 1 | C(O) | 3-aminosulfonyl-4-t-butyl-2-pyridyl |
| 607 | 1 | C(O) | 2-(5-indazol-5-yl)furanyl |
| 608 | 1 | C(O) | 2-(5-indazol-6-yl)thienyl |
| 609 | 1 | C(O) | 4-(2-tetrazolylphenyl)phenyl |
| 610 | 1 | C(O)NH | 4-(2-aminosulfonylphenyl)phenyl |
| 611 | 1 | C(O)NH | 4-(2-aminosulfonylphenyl-2-pyridyl |
| 612 | 1 | C(O)NH | 4-(2-methylaminosulfonyl-phenyl)phenyl |
| 613 | 1 | C(O)NH | 4-(2-ethylaminosulfonyl-phenyl)-2-pyridyl |
| 614 | 1 | C(O)NH | 2-aminosulfonyl-4-cyclohexylphenyl |
| 615 | 1 | C(O)NH | 3-aminosulfonyl-4-t-butyl-2-pyridyl |
| 616 | 1 | C(O)NH | 2-(5-indazol-5-yl)furanyl |
| 617 | 1 | C(O)NH | 2-(5-indazol-6-yl)thienyl |
| 618 | 1 | C(O)NH | 4-(2-tetrazolylphenyl)phenyl |
| 619 | 1 | NHC(O) | 4-(2-aminosulfonylphenyl)phenyl |
| 620 | 1 | NHC(O) | 4-(2-aminosulfonylphenyl)-2-pyridyl |
| 621 | 1 | NHC(O) | 4-(2-methylaminosulfonyl-phenyl)phenyl |
| 622 | 1 | NHC(O) | 4-(2-ethylaminosulfonyl-phenyl)-2-pyridyl |
| 623 | 1 | NHC(O) | 2-aminosulfonyl-4-cyclohexylphenyl |
| 624 | 1 | NHC(O) | 3-aminosulfonyl-4-t-butyl-2-pyridyl |
| 625 | 1 | NHC(O) | 2-(5-indazol-5-yl)furanyl |
| 626 | 1 | NHC(O) | 2-(5-indazol-6-yl)thienyl |
| 627 | 1 | NHC(O) | 4-(2-tetrazolylphenyl)phenyl |
| 628 | 1 | SO₂NH | 4-(2-aminosulfonylphenyl)phenyl |
| 629 | 1 | SO₂NH | 4-(2-aminosulfonylphenyl)-2-pyridyl |
| 630 | 1 | SO₂NH | 4-(2-methylaminosulfonyl-phenyl)phenyl |
| 631 | 1 | SO₂NH | 4-(2-ethylaminosulfonyl-phenyl)-2-pyridyl |
| 632 | 1 | SO₂NH | 2-aminosulfonyl-4-cyclohexylphenyl |
| 633 | 1 | SO₂NH | 3-aminosulfonyl-4-t-butyl-2-pyridyl |
| 634 | 1 | SO₂NH | 2-(5-indazol-5-yl)furanyl |
| 635 | 1 | SO₂NH | 2-(5-indazol-6-yl)thienyl |
| 636 | 1 | SO₂NH | 4-(2-tetrazolylphenyl)phenyl |
| 637 | 0 | CH(CH₂CH₂OH)C(O)NH | 4-(2-aminosulfonylphenyl)phenyl |
| 638 | 0 | CH(CH₂CH₂OH)C(O)NH | 4-(2-aminosulfonylphenyl)-2-pyridyl |
| 639 | 0 | CH(CH₂CH₂OH)C(O)NH | 4-(2-methylaminosulfonyl-phenyl)phenyl |
| 640 | 0 | CH(CH₂CH₂OH)C(O)NH | 4-(2-ethylaminosulfonyl-phenyl)-2-pyridyl |
| 641 | 0 | CH(CH₂CH₂OH)C(O)NH | 2-aminosulfonyl-4-cyclohexylphenyl |
| 642 | 0 | CH(CH₂CH₂OH)C(O)NH | 3-aminosulfonyl-4-t-butyl-2-pyridyl |
| 643 | 0 | CH(CH₂CH₂OH)C(O)NH | 2-(5-indazol-5-yl)furanyl |
| 644 | 0 | CH(CH₂CH₂OH)C(O)NH | 2-(5-indazol-6-yl)thienyl |
| 645 | 0 | CH(CH₂CH₂OH)C(O)NH | 4-(2-tetrazolylphenyl)phenyl |
| 646 | 0 | CH(CH₂-tetrazolyl)C(O)NH | 4-(2-aminosulfonylphenyl)phenyl |
| 647 | 0 | CH(CH₂-tetrazolyl)C(O)NH | 4-(2-aminosulfonylphenyl)-2-pyridyl |
| 648 | 0 | CH(CH₂-tetrazolyl)C(O)NH | 4-(2-methylaminosulfonyl-phenyl)phenyl |
| 649 | 0 | CH(CH₂-tetrazolyl)C(O)NH | 4-(2-ethylaminosulfonyl-phenyl)-2-pyridyl |
| 650 | 0 | CH(CH₂-tetrazolyl)C(O)NH | 2-aminosulfonyl-4-cyclohexylphenyl |
| 651 | 0 | CH(CH₂-tetrazolyl)C(O)NH | 3-aminosulfonyl-4-t-butyl-2-pyridyl |
| 652 | 0 | CH(CH₂-tetrazolyl)C(O)NH | 2-(5-indazol-5-yl)furanyl |
| 653 | 0 | CH(CH₂-tetrazolyl)C(O)NH | 2-(5-indazol-6-yl)thienyl |
| 654 | 0 | CH(CH₂-tetrazolyl)C(O)NH | 4-(2-tetrazolylphenyl)phenyl |

TABLE 13

| Ex | n | Z | A—B |
|---|---|---|---|
| 701 | 1 | C(O) | 4-(2-aminosulfonylphenyl)phenyl |
| 702 | 1 | C(O) | 4-(2-aminosulfonylphenyl)-2-pyridyl |
| 703 | 1 | C(O) | 4-(2-methylaminosulfonyl-phenyl)phenyl |
| 704 | 1 | C(O) | 4-(2-ethylaminosulfonyl-phenyl)-2-pyridyl |
| 705 | 1 | C(O) | 2-aminosulfonyl-4-cyclohexylphenyl |
| 706 | 1 | C(O) | 3-aminosulfonyl-4-t-butyl-2-pyridyl |
| 707 | 1 | C(O) | 2-(5-indazol-5-yl)furanyl |
| 708 | 1 | C(O) | 2-(5-indazol-6-yl)thienyl |
| 709 | 1 | C(O) | 4-(2-tetrazolylphenyl)phenyl |
| 710 | 1 | C(O)NH | 4-(2-methylaminosulfonyl-phenyl)phenyl |
| 711 | 1 | C(O)NH | 4-(2-ethylaminosulfonyl-phenyl)-2-pyridyl |
| 712 | 1 | C(O)NH | 2-aminosulfonyl-4-cyclohexylphenyl |
| 713 | 1 | C(O)NH | 3-aminosulfonyl-4-t-butyl-2-pyridyl |
| 714 | 1 | C(O)NH | 2-(5-indazol-5-yl)furanyl |
| 715 | 1 | C(O)NH | 2-(5-indazol-6-yl)thienyl |
| 716 | 1 | C(O)NH | 4-(2-tetrazolylphenyl)phenyl |
| 717 | 1 | NHC(O) | 4-(2-aminosulfonylphenyl)phenyl |
| 718 | 1 | NHC(O) | 4-(2-aminosulfonylphenyl)-2-pyridyl |
| 719 | 1 | NHC(O) | 4-(2-methylaminosulfonyl-phenyl)phenyl |
| 720 | 1 | NHC(O) | 4-(2-ethylaminosulfonyl-phenyl)-2-pyridyl |
| 721 | 1 | NHC(O) | 2-aminosulfonyl-4-cyclohexylphenyl |
| 722 | 1 | NHC(O) | 3-aminosulfonyl-4-t-butyl-2-pyridyl |
| 723 | 1 | NHC(O) | 2-(5-indazol-5-yl)furanyl |
| 724 | 1 | NHC(O) | 2-(5-indazol-6-yl)thienyl |
| 725 | 1 | NHC(O) | 4-(2-tetrazolylphenyl)phenyl |
| 726 | 1 | $SO_2NH$ | 4-(2-aminosulfonylphenyl)phenyl |
| 727 | 1 | $SO_2NH$ | 4-(2-aminosulfonylphenyl)-2-pyridyl |
| 728 | 1 | $SO_2NH$ | 4-(2-methylaminosulfonyl-phenyl)phenyl |
| 729 | 1 | $SO_2NH$ | 4-(2-ethylaminosulfonyl-phenyl)-2-pyridyl |
| 730 | 1 | $SO_2NH$ | 2-aminosulfonyl-4-cyclohexylphenyl |
| 731 | 1 | $SO_2NH$ | 3-aminosulfonyl-4-t-butyl-2-pyridyl |
| 732 | 1 | $SO_2NH$ | 2-(5-indazol-5-yl)furanyl |
| 733 | 1 | $SO_2NH$ | 2-(5-indazol-6-yl)thienyl |
| 734 | 1 | $SO_2NH$ | 4-(2-tetrazolylphenyl)phenyl |
| 735 | 0 | $CH(CH_2CH_2OH)C(O)NH$ | 4-(2-aminosulfonylphenyl)phenyl |
| 736 | 0 | $CH(CH_2CH_2OH)C(O)NH$ | 4-(2-aminosulfonylphenyl)-2-pyridyl |
| 737 | 0 | $CH(CH_2CH_2OH)C(O)NH$ | 4-(2-methylaminosulfonyl-phenyl)phenyl |
| 738 | 0 | $CH(CH_2CH_2OH)C(O)NH$ | 4-(2-ethylaminosulfonyl-phenyl)-2-pyridyl |
| 739 | 0 | $CH(CH_2CH_2OH)C(O)NH$ | 2-aminosulfonyl-4-cyclohexylphenyl |
| 740 | 0 | $CH(CH_2CH_2OH)C(O)NH$ | 3-aminosulfonyl-4-t-butyl-2-pyridyl |
| 741 | 0 | $CH(CH_2CH_2OH)C(O)NH$ | 2-(5-indazol-5-yl)furanyl |
| 742 | 0 | $CH(CH_2CH_2OH)C(O)NH$ | 2-(5-indazol-6-yl)thienyl |
| 743 | 0 | $CH(CH_2CH_2OH)C(O)NH$ | 4-(2-tetrazolylphenyl)phenyl |
| 744 | 0 | $CH(CH_2\text{-tetrazolyl})C(O)NH$ | 4-(2-aminosulfonylphenyl)phenyl |
| 745 | 0 | $CH(CH_2\text{-tetrazolyl})C(O)NH$ | 4-(2-aminosulfonylphenyl)-2-pyridyl |
| 746 | 0 | $CH(CH_2\text{-tetrazolyl})C(O)NH$ | 4-(2-methylaminosulfonyl-phenyl)phenyl |
| 747 | 0 | $CH(CH_2\text{-tetrazolyl})C(O)NH$ | 4-(2-ethylaminosulfonyl-phenyl)-2-pyridyl |
| 748 | 0 | $CH(CH_2\text{-tetrazolyl})C(O)NH$ | 2-aminosulfonyl-4-cyclohexylphenyl |
| 749 | 0 | $CH(CH_2\text{-tetrazolyl})C(O)NH$ | 3-aminosulfonyl-4-t-butyl-2-pyridyl |
| 750 | 0 | $CH(CH_2\text{-tetrazolyl})C(O)NH$ | 2-(5-indazol-5-yl)furanyl |
| 751 | 0 | $CH(CH_2\text{-tetrazolyl})C(O)NH$ | 2-(5-indazol-6-yl)thienyl |
| 752 | 0 | $CH(CH_2\text{-tetrazolyl})C(O)NH$ | 4-(2-tetrazolylphenyl)phenyl |

TABLE 14

| Ex | n | Z | A—B |
|---|---|---|---|
| 801 | 1 | C(O) | 4-(2-aminosulfonylphenyl)phenyl |
| 802 | 1 | C(O) | 4-(2-aminosulfonylphenyl)-2-pyridyl |
| 803 | 1 | C(O) | 4-(2-methylaminosulfonyl-phenyl)phenyl |
| 804 | 1 | C(O) | 4-(2-ethylaminosulfonyl-phenyl)-2-pyridyl |
| 805 | 1 | C(O) | 2-aminosulfonyl-4-cyclohexylphenyl |
| 806 | 1 | C(O) | 3-aminosulfonyl-4-t-butyl-2-pyridyl |
| 807 | 1 | C(O) | 2-(5-indazol-5-yl)furanyl |
| 808 | 1 | C(O) | 2-(5-indazol-6-yl)thienyl |
| 809 | 1 | C(O) | 4-(2-tetrazolylphenyl)phenyl |
| 810 | 1 | C(O)NH | 4-(2-aminosulfonylphenyl)phenyl |
| 811 | 1 | C(O)NH | 4-(2-aminosulfonylphenyl)-2-pyridyl |
| 812 | 1 | C(O)NH | 4-(2-methylaminosulfonyl-phenyl)phenyl |
| 813 | 1 | C(O)NH | 4-(2-ethylaminosulfonyl-phenyl-2-pyridyl |
| 814 | 1 | C(O)NH | 2-aminosulfonyl-4-cyclohexylphenyl |
| 815 | 1 | C(O)NH | 3-aminosulfonyl-4-t-butyl-2-pyridyl |
| 816 | 1 | C(O)NH | 2-(5-indazol-5-yl)furanyl |
| 817 | 1 | C(O)NH | 2-(5-indazol-6-yl)thienyl |
| 818 | 1 | C(O)NH | 4-(2-tetrazolylphenyl)phenyl |
| 819 | 1 | NHC(O) | 4-(2-aminosulfonylphenyl)phenyl |

TABLE 14-continued

| Ex | n | Z | A—B |
|---|---|---|---|
| 820 | 1 | NHC(O) | 4-(2-aminosulfonylphenyl)-2-pyridyl |
| 821 | 1 | NHC(O) | 4-(2-methylaminosulfonyl-phenyl)phenyl |
| 822 | 1 | NHC(O) | 4-(2-ethylaminosulfonyl-phenyl)-2-pyridyl |
| 823 | 1 | NHC(O) | 2-aminosulfonyl-4-cyclohexylphenyl |
| 824 | 1 | NHC(O) | 3-aminosulfonyl-4-t-butyl-2-pyridyl |
| 825 | 1 | NHC(O) | 2-(5-indazol-5-yl)furanyl |
| 826 | 1 | NHC(O) | 2-(5-indazol-6-yl)thienyl |
| 827 | 1 | NHC(O) | 4-(2-tetrazolylphenyl)phenyl |
| 828 | 1 | SO$_2$NH | 4-(2-aminosulfonylphenyl)phenyl |
| 829 | 1 | SO$_2$NH | 4-(2-aminosulfonylphenyl)-2-pyridyl |
| 830 | 1 | SO$_2$NH | 4-(2-methylaminosulfonyl-phenyl)phenyl |
| 831 | 1 | SO$_2$NH | 4-(2-ethylaminosulfonyl-phenyl)-2-pyridyl |
| 832 | 1 | SO$_2$NH | 2-aminosulfonyl-4-cyclohexylphenyl |
| 833 | 1 | SO$_2$NH | 3-aminosulfonyl-4-t-butyl-2-pyridyl |
| 834 | 1 | SO$_2$NH | 2-(5-indazol-5-yl)furanyl |
| 835 | 1 | SO$_2$NH | 2-(5-indazol-6-yl)thienyl |
| 836 | 1 | SO$_2$NH | 4-(2-tetrazolylphenyl)phenyl |
| 837 | 0 | CH(CH$_2$CH$_2$OH)C(O)NH | 4-(2-aminosulfonylphenyl)phenyl |
| 838 | 0 | CH(CH$_2$CH$_2$OH)C(O)NH | 4-(2-aminosulfonylphenyl)-2-pyridyl |
| 839 | 0 | CH(CH$_2$CH$_2$OH)C(O)NH | 4-(2-methylaminosulfonyl-phenyl)phenyl |
| 840 | 0 | CH(CH$_2$CH$_2$OH)C(O)NH | 4-(2-ethylaminosulfonyl-phenyl)-2-pyridyl |
| 841 | 0 | CH(CH$_2$CH$_2$OH)C(O)NH | 2-aminosulfonyl-4-cyclohexylphenyl |
| 842 | 0 | CH(CH$_2$CH$_2$OH)C(O)NH | 3-aminosulfonyl-4-t-butyl-2-pyridyl |
| 843 | 0 | CH(CH$_2$CH$_2$OH)C(O)NH | 2-(5-indazol-5-yl)furanyl |
| 844 | 0 | CH(CH$_2$CH$_2$OH)C(O)NH | 2-(5-indazol-6-yl)thienyl |
| 845 | 0 | CH(CH$_2$CH$_2$OH)C(O)NH | 4-(2-tetrazolylphenyl)phenyl |
| 846 | 0 | CH(CH$_2$-tetrazolyl)C(O)NH | 4-(2-aminosulfonylphenyl)phenyl |
| 847 | 0 | CH(CH$_2$-tetrazolyl)C(O)NH | 4-(2-aminosulfonylphenyl)-2-pyridyl |
| 848 | 0 | CH(CH$_2$-tetrazolyl)C(O)NH | 4-(2-methylaminosulfonyl-phenyl)phenyl |
| 849 | 0 | CH(CH$_2$-tetrazolyl)C(O)NH | 4-(2-ethylaminosulfonyl-phenyl)-2-pyridyl |
| 850 | 0 | CH(CH$_2$-tetrazolyl)C(O)NH | 2-aminosulfonyl-4-cyclohexylphenyl |
| 851 | 0 | CH(CH$_2$-tetrazolyl)C(O)NH | 3-aminosulfonyl-4-t-butyl-2-pyridyl |
| 852 | 0 | CH(CH$_2$-tetrazolyl)C(O)NH | 2-(5-indazol-5-yl)furanyl |
| 853 | 0 | CH(CH$_2$-tetrazolyl)C(O)NH | 2-(5-indazol-6-yl)thienyl |
| 854 | 0 | CH(CH$_2$-tetrazolyl)C(O)NH | 4-(2-tetrazolylphenyl)phenyl |

TABLE 15

| Ex | n | Z | A—B |
|---|---|---|---|
| 901 | 1 | C(O) | 4-(2-aminosulfonylphenyl)phenyl |
| 902 | 1 | C(O) | 4-(2-aminosulfonylphenyl)-2-pyridyl |
| 903 | 1 | C(O) | 4-(2-methylaminosulfonyl-phenyl)phenyl |
| 904 | 1 | C(O) | 4-(2-ethylaminosulfonyl-phenyl)-2-pyridyl |
| 905 | 1 | C(O) | 2-aminosulfonyl-4-cyclohexylphenyl |
| 906 | 1 | C(O) | 3-aminosulfonyl-4-t-butyl-2-pyridyl |
| 907 | 1 | C(O) | 2-(5-indazol-5-yl)furanyl |
| 908 | 1 | C(O) | 2-(5-indazol-6-yl)thienyl |
| 909 | 1 | C(O) | 4-(2-tetrazolylphenyl)phenyl |
| 910 | 1 | C(O)NH | 4-(2-aminosulfonylphenyl)phenyl |
| 911 | 1 | C(O)NH | 4-(2-aminosulfonylphenyl)-2-pyridyl |
| 912 | 1 | C(O)NH | 4-(2-methylaminosulfonyl-phenyl)phenyl |
| 913 | 1 | C(O)NH | 4-(2-ethylaminosulfonyl-phenyl)-2-pyridyl |
| 914 | 1 | C(O)NH | 2-aminosulfonyl-4-cyclohexylphenyl |
| 915 | 1 | C(O)NH | 3-aminosulfonyl-4-t-butyl-2-pyridyl |
| 916 | 1 | C(O)NH | 2-(5-indazol-5-yl)furanyl |
| 917 | 1 | C(O)NH | 2-(5-indazol-6-yl)thienyl |
| 918 | 1 | C(O)NH | 4-(2-tetrazolylphenyl)phenyl |
| 919 | 1 | NHC(O) | 4-(2-aminosulfonylphenyl)phenyl |
| 920 | 1 | NHC(O) | 4-(2-aminosulfonylphenyl)-2-pyridyl |
| 921 | 1 | NHC(O) | 4-(2-methylaminosulfonyl-phenyl)phenyl |
| 922 | 1 | NHC(O) | 4-(2-ethylaminosulfonyl-phenyl)-2-pyridyl |
| 923 | 1 | NHC(O) | 2-aminosulfonyl-4-cyclohexylphenyl |
| 924 | 1 | NHC(O) | 3-aminosulfonyl-4-t-butyl-2-pyridyl |
| 925 | 1 | NHC(O) | 2-(5-indazol-5-yl)furanyl |
| 926 | 1 | NHC(O) | 2-(5-indazol-6-yl)thienyl |
| 927 | 1 | NHC(O) | 4-(2-tetrazolylphenyl)phenyl |
| 928 | 1 | SO$_2$NH | 4-(2-aminosulfonylphenyl)phenyl |
| 929 | 1 | SO$_2$NH | 4-(2-aminosulfonylphenyl)-2-pyridyl |
| 930 | 1 | SO$_2$NH | 4-(2-methylaminosulfonyl-phenyl)phenyl |
| 931 | 1 | SO$_2$NH | 4-(2-ethylaminosulfonyl-phenyl)-2-pyridyl |
| 932 | 1 | SO$_2$NH | 2-aminosulfonyl-4-cyclohexylphenyl |
| 933 | 1 | SO$_2$NH | 3-aminosulfonyl-4-t-butyl-2-pyridyl |
| 934 | 1 | SO$_2$NH | 2-(5-indazol-5-yl)furanyl |
| 935 | 1 | SO$_2$NH | 2-(5-indazol-6-yl)thienyl |
| 936 | 1 | SO$_2$NH | 4-(2-tetrazolylphenyl)phenyl |
| 937 | 0 | CH(CH$_2$CH$_2$OH)C(O)NH | 4-(2-aminosulfonylphenyl)phenyl |
| 938 | 0 | CH(CH$_2$CH$_2$OH)C(O)NH | 4-(2-aminosulfonylphenyl)-2-pyridyl |
| 939 | 0 | CH(CH$_2$CH$_2$OH)C(O)NH | 4-(2-methylaminosulfonyl-phenyl)phenyl |
| 940 | 0 | CH(CH$_2$CH$_2$OH)C(O)NH | 4-(2-ethylaminosulfonyl-phenyl)-2-pyridyl |

TABLE 15-continued

Structure: benzofuran-5-carboxamidine with 3-position substituent —(CH₂)ₙ—Z—A—B

| Ex | n | Z | A—B |
|---|---|---|---|
| 941 | 0 | CH(CH₂CH₂OH)C(O)NH | 2-aminosulfonyl-4-cyclohexylphenyl |
| 942 | 0 | CH(CH₂CH₂OH)C(O)NH | 3-aminosulfonyl-4-t-butyl-2-pyridyl |
| 943 | 0 | CH(CH₂CH₂OH)C(O)NH | 2-(5-indazol-5-yl)furanyl |
| 944 | 0 | CH(CH₂CH₂OH)C(O)NH | 2-(5-indazol-6-yl)thienyl |
| 945 | 0 | CH(CH₂CH₂OH)C(O)NH | 4-(2-tetrazolylphenyl)phenyl |
| 946 | 0 | CH(CH₂-tetrazolyl)C(O)NH | 4-(2-aminosulfonylphenyl)phenyl |
| 947 | 0 | CH(CH₂-tetrazolyl)C(O)NH | 4-(2-aminosulfonylphenyl)-2-pyridyl |
| 948 | 0 | CH(CH₂-tetrazolyl)C(O)NH | 4-(2-methylaminosulfonyl-phenyl)phenyl |
| 949 | 0 | CH(CH₂-tetrazolyl)C(O)NH | 4-(2-ethylaminosulfonyl-phenyl)-2-pyridyl |
| 950 | 0 | CH(CH₂-tetrazolyl)C(O)NH | 2-aminosulfonyl-4-cyclohexylphenyl |
| 951 | 0 | CH(CH₂-tetrazolyl)C(O)NH | 3-aminosulfonyl-4-t-butyl-2-pyridyl |
| 952 | 0 | CH(CH₂-tetrazolyl)C(O)NH | 2-(5-indazol-5-yl)furanyl |
| 953 | 0 | CH(CH₂-tetrazolyl)C(O)NH | 2-(5-indazol-6-yl)thienyl |
| 954 | 0 | CH(CH₂-tetrazolyl)C(O)NH | 4-(2-tetrazolylphenyl)phenyl |

TABLE 16

Structure: benzothiophene-5-carboxamidine with 3-position substituent —(CH₂)ₙ—Z—A—B

| Ex | n | Z | A-B |
|---|---|---|---|
| 1001 | 1 | C(O) | 4-(2-aminosulfonylphenyl)phenyl |
| 1002 | 1 | C(O) | 4-(2-aminosulfonylphenyl)-2-pyridyl |
| 1003 | 1 | C(O) | 4-(2-methylaminosulfonyl-phenyl) phenyl |
| 1004 | 1 | C(O) | 4-(2-ethylaminosulfonyl-phenyl)-2-pyridyl |
| 1005 | 1 | C(O) | 2-aminosulfonyl-4-cyclohexylphenyl |
| 1006 | 1 | C(O) | 3-aminosulfonyl-4-t-butyl-2-pyridyl |
| 1007 |   | C(O) | 2-(5-indazol-5-yl)furanyl |
| 1008 | 1 | C(O) | 2-(5-indazol-6-yl)thienyl |
| 1009 | 1 | C(O) | 4-(2-tetrazolylphenyl)phenyl |
| 1010 | 1 | C(O)NH | 4-(2-aminosulfonylphenyl)phenyl |
| 1011 | 1 | C(O)NH | 4-(2-aminosulfonylphenyl)-2-pyridyl |
| 1012 | 1 | C(O)NH | 4-(2-methylaminosulfonyl-phenyl)phenyl |
| 1013 | 1 | C(O)NH | 4-(2-ethylaminosulfonyl-phenyl)-2-pyridyl |
| 1014 | 1 | C(O)NH | 2-aminosulfonyl-4-cyclohexylphenyl |
| 1015 | 1 | C(O)NH | 3-aminosulfonyl-4-t-butyl-2-pyridyl |
| 1016 | 1 | C(O)NH | 2-(5-indazol-5-yl)furanyl |
| 1017 | 1 | C(O)NH | 2-(5-indazol-6-yl)thienyl |
| 1018 | 1 | C(O)NH | 4-(2-tetrazolylphenyl)phenyl |
| 1019 | 1 | NHC(O) | 4-(2-aminosulfonylphenyl)phenyl |
| 1020 | 1 | NHC(O) | 4-(2-aminosulfonylphenyl)-2-pyridyl |
| 1021 | 1 | NHC(O) | 4-(2-methylaminosulfonyl-phenyl)phenyl |
| 1022 | 1 | NHC(O) | 4-(2-ethylaminosulfonyl-phenyl)-2-pyridyl |
| 1023 | 1 | NHC(O) | 2-aminosulfonyl-4-cyclohexylphenyl |
| 1024 | 1 | NHC(O) | 3-aminosulfonyl-4-t-butyl-2-pyridyl |
| 1025 | 1 | NHC(O) | 2-(5-indazol-5-yl)furanyl |
| 1026 | 1 | NHC(O) | 2-(5-indazol-6-yl)thienyl |
| 1027 | 1 | NHC(O) | 4-(2-tetrazolylphenyl)phenyl |
| 1028 | 1 | SO₂NH | 4-(2-aminosulfonylphenyl)phenyl |
| 1029 | 1 | SO₂NH | 4-(2-aminosulfonylphenyl)-2-pyridyl |
| 1030 | 1 | SO₂NH | 4-(2-methylaminosulfonyl-phenyl)phenyl |
| 1031 | 1 | SO₂NH | 4-(2-ethylaminosulfonyl-phenyl)-2-pyridyl |
| 1032 | 1 | SO₂NH | 2-aminosulfonyl-4-cyclohexylphenyl |
| 1033 | 1 | SO₂NH | 3-aminosulfonyl-4-t-butyl-2-pyridyl |
| 1034 | 1 | SO₂NH | 2-(5-indazol-5-yl)furanyl |
| 1035 | 1 | SO₂NH | 2-(5-indazol-6-yl)thienyl |
| 1036 | 1 | SO₂NH | 4-(2-tetrazolylphenyl)phenyl |
| 1037 | 0 | CH(CH₂CH₂OH)C(O)NH | 4-(2-aminosulfonylphenyl)phenyl |
| 1038 | 0 | CH(CH₂CH₂OH)C(O)NH | 4-(2-aminosulfonylphenyl)-2-pyridyl |
| 1039 | 0 | CH(CH₂CH₂OH)C(O)NH | 4-(2-methylaminosulfonyl-phenyl)phenyl |
| 1040 | 0 | CH(CH₂CH₂OH)C(O)NH | 4-(2-ethylaminosulfonyl-phenyl)-2-pyridyl |
| 1041 | 0 | CH(CH₂CH₂OH)C(O)NH | 2-aminosulfonyl-4-cyclohexylphenyl |
| 1042 | 0 | CH(CH₂CH₂OH)C(O)NH | 3-aminosulfonyl-4-t-butyl-2-pyridyl |
| 1043 | 0 | CH(CH₂CH₂OH)C(O)NH | 2-(5-indazol-5-yl)furanyl |
| 1044 | 0 | CH(CH₂CH₂OH)C(O)NH | 2-(5-indazol-6-yl)thienyl |
| 1045 | 0 | CH(CH₂CH₂OH)C(O)NH | 4-(2-tetrazolylphenyl)phenyl |
| 1046 | 0 | CH(CH₂-tetrazolyl)C(O)NH | 4-(2-aminosulfonylphenyl)phenyl |
| 1047 | 0 | CH(CH₂-tetrazolyl)C(O)NH | 4-(2-aminosulfonylphenyl)-2-pyridyl |
| 1048 | 0 | CH(CH₂-tetrazolyl)C(O)NH | 4-(2-methylaminosulfonyl-phenyl)phenyl |
| 1049 | 0 | CH(CH₂-tetrazolyl)C(O)NH | 4-(2-ethylaminosulfonyl-phenyl)-2-pyridyl |
| 1050 | 0 | CH(CH₂-tetrazolyl)C(O)NH | 2-aminosulfonyl-4-cyclohexylphenyl |
| 1051 | 0 | CH(CH₂-tetrazolyl)C(O)NH | 3-aminosulfonyl-4-t-butyl-2-pyridyl |
| 1052 | 0 | CH(CH₂-tetrazolyl)C(O)NH | 2-(5-indazol-5-yl)furanyl |
| 1053 | 0 | CH(CH₂-tetrazolyl)C(O)NH | 2-(5-indazol-6-yl)thienyl |
| 1054 | 0 | CH(CH₂-tetrazolyl)C(O)NH | 4-(2-tetrazolylphenyl)phenyl |

TABLE 17

| Ex | n | Z | R¹ | A-B |
|---|---|---|---|---|
| 1101 | 1 | C(O) | H | 3-acetyl-4-benzylpiperidine |
| 1102 | 1 | C(O) | H | 4-(4-fluorobenzyl)piperidine |
| 1103 | 1 | C(O) | H | 4-(2,3-difluorobenzyl)piperidine |
| 1104 | 1 | C(O) | H | 4-(2-chloro-4-fluorobenzyl)piperidine |
| 1105 | 1 | C(O) | CH₂CH₂OH | 3-acetyl-4-benzylpiperidine |
| 1106 | 1 | C(O) | CH₂CH₂OH | 4-(3-fluorobenzyl)piperidine |
| 1107 | 1 | C(O) | CH₂CH₂OH | 4-(4-fluorobenzyl)piperidine |
| 1108 | 1 | C(O) | CH₂CH₂OH | 4-(2,3-difluorobenzyl)piperidine |
| 1109 | 1 | C(O) | CH₂CH₂OH | 4-(2-chloro-4-fluorobenzyl)piperidine |
| 1110 | 1 | C(O) | CH₂OCH₃ | 4-benzylpiperidine |
| 1111 | 1 | C(O) | CH₂OCH₃ | 3-acetyl-4-benzylpiperidine |
| 1112 | 1 | C(O) | CH₂OCH₃ | 4-(3-fluorobenzyl)piperidine |
| 1113 | 1 | C(O) | CH₂OCH₃ | 4-(4-fluorobenzyl)piperidine |
| 1114 | 1 | C(O) | CH₂OCH₃ | 4-(2,3-difluorobenzyl)piperidine |
| 1115 | 1 | C(O) | CH₂OCH₃ | 4-(2-chloro-4-fluorobenzyl)piperidine |
| 1116 | 1 | C(O) | CH₂CH₂-tetrazolyl | 4-benzylpiperidine |
| 1117 | 1 | C(O) | CH₂CH₂-tetrazolyl | 3-acetyl-4-benzylpiperidine |
| 1118 | 1 | C(O) | CH₂CH₂-tetrazolyl | 4-(3-fluorobenzyl)piperidine |
| 1119 | 1 | C(O) | CH₂CH₂-tetrazolyl | 4-(4-fluorobenzyl)piperidine |
| 1120 | 1 | C(O) | CH₂CH₂-tetrazolyl | 4-(2,3-difluorobenzyl)piperidine |
| 1121 | 1 | C(O) | CH₂CH₂-tetrazolyl | 4-(2-chloro-4-fluorobenzyl)piperidine |
| 1122 | 1 | C(O)NH | H | 3-acetyl-4-benzylpiperidine |
| 1123 | 1 | C(O)NH | H | 4-(3-fluorobenzyl)piperidine |
| 1124 | 1 | C(O)NH | H | 4-(4-fluorobenzyl)piperidine |
| 1125 | 1 | C(O)NH | H | 4-(2,3-difluorobenzyl)piperidine |
| 1126 | 1 | C(O)NH | H | 4-(2-chloro-4-fluorobenzyl)piperidine |
| 1127 | 1 | C(O)NH | CH₂CH₂OH | 4-benzylpiperidine |
| 1128 | 1 | C(O)NH | CH₂CH₂OH | 3-acetyl-4-benzylpiperidine |
| 1129 | 1 | C(O)NH | CH₂CH₂OH | 4-(3-fluorobenzyl)piperidine |
| 1130 | 1 | C(O)NH | CH₂CH₂OH | 4-(4-fluorobenzyl)piperidine |
| 1131 | 1 | C(O)NH | CH₂CH₂OH | 4-(2,3-difluorobenzyl)piperidine |
| 1132 | 1 | C(O)NH | CH₂CH₂OH | 4-(2-chloro-4-fluorobenzyl)piperidine |
| 1133 | 1 | C(O)NH | CH₂OCH₃ | 4-benzylpiperidine |
| 1134 | 1 | C(O)NH | CH₂OCH₃ | 3-acetyl-4-benzylpiperidine |
| 1135 | 1 | C(O)NH | CH₂OCH₃ | 4-(3-fluorobenzyl)piperidine |
| 1136 | 1 | C(O)NH | CH₂OCH₃ | 4-(4-fluorobenzyl)piperidine |
| 1137 | 1 | C(O)NH | CH₂OCH₃ | 4-(2,3-difluorobenzyl)piperidine |
| 1138 | 1 | C(O)NH | CH₂OCH₃ | 4-(2-chloro-4-fluorobenzyl)piperidine |
| 1139 | 1 | C(O)NH | CH₂CH₂-tetrazolyl | 4-benzylpiperidine |
| 1140 | 1 | C(O)NH | CH₂CH₂-tetrazolyl | 3-acetyl-4-benzylpiperidine |
| 1141 | 1 | C(O)NH | CH₂CH₂-tetrazolyl | 4-(3-fluorobenzyl)piperidine |
| 1142 | 1 | C(O)NH | CH₂CH₂-tetrazolyl | 4-(4-fluorobenzyl)piperidine |
| 1143 | 1 | C(O)NH | CH₂CH₂-tetrazolyl | 4-(2,3-difluorobenzyl)piperidine |
| 1144 | 1 | C(O)NH | CH₂CH₂-tetrazolyl | 4-(2-chloro-4-fluorobenzyl)piperidine |
| 1145 | 1 | SO₂NH | H | 4-benzylpiperidine |
| 1146 | 1 | SO₂NH | H | 3-acetyl-4-benzylpiperidine |
| 1147 | 1 | SO₂NH | H | 4-(3-fluorobenzyl)piperidine |
| 1148 | 1 | SO₂NH | H | 4-(4-fluorobenzyl)piperidine |
| 1149 | 1 | SO₂NH | H | 4-(2,3-difluorobenzyl)piperidine |
| 1150 | 1 | SO₂NH | H | 4-(2-chloro-4-fluorobenzyl)piperidine |
| 1151 | 1 | SO₂NH | CH₂CH₂OH | 4-benzylpiperidine |
| 1152 | 1 | SO₂NH | CH₂CH₂OH | 3-acetyl-4-benzylpiperidine |
| 1153 | 1 | SO₂NH | CH₂CH₂OH | 4-(3-fluorobenzyl)piperidine |
| 1154 | 1 | SO₂NH | CH₂CH₂OH | 4-(4-fluorobenzyl)piperidine |
| 1155 | 1 | SO₂NH | CH₂CH₂OH | 4-(2,3-difluorobenzyl)piperidine |
| 1156 | 1 | SO₂NH | CH₂CH₂OH | 4-(2-chloro-4-fluorobenzyl)piperidine |
| 1157 | 1 | SO₂NH | CH₂OCH₃ | 4-benzylpiperidine |
| 1158 | 1 | SO₂NH | CH₂OCH₃ | 3-acetyl-4-benzylpiperidine |
| 1159 | 1 | SO₂NH | CH₂OCH₃ | 4-(3-fluorobenzyl)piperidine |
| 1160 | 1 | SO₂NH | CH₂OCH₃ | 4-(4-fluorobenzyl)piperidine |
| 1161 | 1 | SO₂NH | CH₂OCH₃ | 4-(2,3-difluorobenzyl)piperidine |
| 1162 | 1 | SO₂NH | CH₂OCH₃ | 4-(2-chloro-4-fluorobenzyl)piperidine |
| 1163 | 1 | SO₂NH | CH₂CH₂-tetrazolyl | 4-benzylpiperidine |
| 1164 | 1 | SO₂NH | CH₂CH₂-tetrazolyl | 3-acetyl-4-benzylpiperidine |
| 1165 | 1 | SO₂NH | CH₂CH₂-tetrazolyl | 4-(3-fluorobenzyl)piperidine |
| 1166 | 1 | SO₂NH | CH₂CH₂-tetrazalyl | 4-(4-fluorobenzyl)piperidine |
| 1167 | 1 | SO₂NH | CH₂CH₂-tetrazolyl | 4-(2,3-difluorobenzyl)piperidine |
| 1168 | 1 | SO₂NH | CH₂CH₂-tetrazolyl | 4-(2-chloro-4-fluorobenzy1)piperidine |

TABLE 18

| Ex | n | Z | R¹ | A-B |
|---|---|---|---|---|
| 1201 | 1 | C(O) | H | 4-benzylpiperidine |
| 1202 | 1 | C(O) | H | 3-acetyl-4-benzylpiperidine |
| 1203 | 1 | C(O) | H | 4-(3-fluorobenzyl)piperidine |
| 1204 | 1 | C(O) | H | 4-(4-fluorobenzyl)piperidine |
| 1205 | 1 | C(O) | H | 4-(2,3-difluorobenzyl)piperidine |
| 1206 | 1 | C(O) | H | 4-(2-chloro-4-fluorobenzyl)piperidine |
| 1207 | 1 | C(O) | CH₂CH₂OH | 4-benzylpiperidine |
| 1208 | 1 | C(O) | CH₂CH₂OH | 3-acetyl-4-benzylpiperidine |
| 1209 | 1 | C(O) | CH₂CH₂OH | 4-(3-fluorobenzyl)piperidine |

TABLE 18-continued

[Structure: indoline with HN=C(NH2)- at 6-position, R1 at 3-position, N1 substituted with -(CH2)n-Z-A-B]

| Ex | n | Z | R¹ | A-B |
|---|---|---|---|---|
| 1210 | 1 | C(O) | CH₂CH₂OH | 4-(4-fluorobenzyl)piperidine |
| 1211 | 1 | C(O) | CH₂CH₂OH | 4-(2,3-difluorobenzyl)piperidine |
| 1212 | 1 | C(O) | CH₂CH₂OH | 4-(2-chloro-4-fluorobenzyl)piperidine |
| 1213 | 1 | C(O) | CH₂OCH₃ | 4-benzylpiperidine |
| 1214 | 1 | C(O) | CH₂OCH₃ | 3-acetyl-4-benzylpiperidine |
| 1215 | 1 | C(O) | CH₂OCH₃ | 4-(3-fluorobenzyl)piperidine |
| 1216 | 1 | C(O) | CH₂OCH₃ | 4-(4-fluorobenzyl)piperidine |
| 1217 | 1 | C(O) | CH₂OCH₃ | 4-(2,3-difluorobenzyl)piperidine |
| 1218 | 1 | C(O) | CH₂OCH₃ | 4-(2-chloro-4-fluorobenzyl)piperidine |
| 1219 | 1 | C(O) | CH₂CH₂-tetrazolyl | 4-benzylpiperidine |
| 1220 | 1 | C(O) | CH₂CH₂-tetrazolyl | 3-acetyl-4-benzylpiperidine |
| 1221 | 1 | C(O) | CH₂CH₂-tetrazolyl | 4-(3-fluorobenzyl)piperidine |
| 1222 | 1 | C(O) | CH₂CH₂-tetrazolyl | 4-(4-fluorobenzyl)piperidine |
| 1223 | 1 | C(O) | CH₂CH₂-tetrazolyl | 4-(2,3-difluorobenzyl)piperidine |
| 1224 | 1 | C(O) | CH₂CH₂-tetrazolyl | 4-(2-chloro-4-fluorobenzyl)piperidine |
| 1225 | 1 | C(O)NH | H | 4-benzylpiperidine |
| 1226 | 1 | C(O)NH | H | 3-acetyl-4-benzylpiperidine |
| 1227 | 1 | C(O)NH | H | 4-(3-fluorobenzyl)piperidine |
| 1228 | 1 | C(O)NH | H | 4-(4-fluorobenzyl)piperidine |
| 1229 | 1 | C(O)NH | H | 4-(2,3-difluorobenzyl)piperidine |
| 1230 | 1 | C(O)NH | H | 4-(2-chloro-4-fluorobenzyl)piperidine |
| 1231 | 1 | C(O)NH | CH₂CH₂OH | 4-benzylpiperidine |
| 1232 | 1 | C(O)NH | CH₂CH₂OH | 3-acetyl-4-benzylpiperidine |
| 1233 | 1 | C(O)NH | CH₂CH₂OH | 4-(3-fluorobenzyl)piperidine |
| 1234 | 1 | C(O)NH | CH₂CH₂OH | 4-(4-fluorobenzyl)piperidine |
| 1235 | 1 | C(O)NH | CH₂CH₂OH | 4-(2,3-difluorobenzyl)piperidine |
| 1236 | 1 | C(O)NH | CH₂CH₂OH | 4-(2-chloro-4-fluorobenzyl)piperidine |
| 1237 | 1 | C(O)NH | CH₂OCH₃ | 4-benzylpiperidine |
| 1238 | 1 | C(O)NH | CH₂OCH₃ | 3-acetyl-4-benzylpiperidine |
| 1239 | 1 | C(O)NH | CH₂OCH₃ | 4-(3-fluorobenzyl)piperidine |
| 1240 | 1 | C(O)NH | CH₂OCH₃ | 4-(4-fluorobenzyl)piperidine |
| 1241 | 1 | C(O)NH | CH₂OCH₃ | 4-(2,3-difluorobenzyl)piperidine |
| 1242 | 1 | C(O)NH | CH₂OCH₃ | 4-(2-chloro-4-fluorobenzyl)piperidine |
| 1243 | 1 | C(O)NH | CH₂CH₂-tetrazolyl | 4-benzylpiperidine |
| 1244 | 1 | C(O)NH | CH₂CH₂-tetrazolyl | 3-acetyl-4-benzylpiperidine |
| 1245 | 1 | C(O)NH | CH₂CH₂-tetrazolyl | 4-(3-fluorobenzyl)piperidine |
| 1246 | 1 | C(O)NH | CH₂CH₂-tetrazolyl | 4-(4-fluorobenzyl)piperidine |
| 1247 | 1 | C(O)NH | CH₂CH₂-tetrazolyl | 4-(2,3-difluorobenzyl)piperidine |
| 1248 | 1 | C(O)NH | CH₂CH₂-tetrazolyl | 4-(2-chloro-4-fluorobenzyl)piperidine |
| 1249 | 1 | SO₂NH | H | 4-benzylpiperidine |
| 1250 | 1 | SO₂NH | H | 3-acetyl-4-benzylpiperidine |
| 1251 | 1 | SO₂NH | H | 4-(3-fluorobenzyl)piperidine |
| 1252 | 1 | SO₂NH | H | 4-(4-fluorobenzyl)piperidine |
| 1253 | 1 | SO₂NH | H | 4-(2,3-difluorobenzyl)piperidine |
| 1254 | 1 | SO₂NH | H | 4-(2-chloro-4-fluorobenzyl)piperidine |
| 1255 | 1 | SO₂NH | CH₂CH₂OH | 4-benzylpiperidine |
| 1256 | 1 | SO₂NH | CH₂CH₂OH | 3-acetyl-4-benzylpiperidine |
| 1257 | 1 | SO₂NH | CH₂CH₂OH | 4-(3-fluorobenzyl)piperidine |
| 1258 | 1 | SO₂NH | CH₂CH₂OH | 4-(4-fluorobenzyl)piperidine |
| 1259 | 1 | SO₂NH | CH₂CH₂OH | 4-(2,3-difluorobenzyl)piperidine |
| 1260 | 1 | SO₂NH | CH₂CH₂OH | 4-(2-chloro-4-fluorobenzyl)piperidine |
| 1261 | 1 | SO₂NH | CH₂OCH₃ | 4-benzylpiperidine |
| 1262 | 1 | SO₂NH | CH₂OCH₃ | 3-acetyl-4-benzylpiperidine |
| 1263 | 1 | SO₂NH | CH₂OCH₃ | 4-(3-fluorobenzyl)piperidine |
| 1264 | 1 | SO₂NH | CH₂OCH₃ | 4-(4-fluorobenzyl)piperidine |
| 1265 | 1 | SO₂NH | CH₂OCH₃ | 4-(2,3-difluorobenzyl)piperidine |
| 1266 | 1 | SO₂NH | CH₂OCH₃ | 4-(2-chloro-4-fluorobenzyl)piperidine |
| 1267 | 1 | SO₂NH | CH₂CH₂-tetrazolyl | 4-benzylpiperidine |
| 1268 | 1 | SO₂NH | CH₂CH₂-tetrazolyl | 3-acetyl-4-benzylpiperidine |
| 1269 | 1 | SO₂NH | CH₂CH₂-tetrazolyl | 4-(3-fluorobenzyl)piperidifle |
| 1270 | 1 | SO₂NH | CH₂CH₂-tetrazolyl | 4-(4-fluorobenzyl)piperidine |
| 1271 | 1 | SO₂NH | CH₂CH₂-tetrazolyl | 4-(2,3-difluorobenzyl)piperidine |
| 1272 | 1 | SO₂NH | CH₂CH₂-tetrazolyl | 4-(2-chloro-4-fluorobenzyl)piperidine |

TABLE 19

[Structure: indazole with HN=C(NH2)- at 6-position, R1 at 3-position, N1 substituted with -(CH2)n-Z-A-B]

| Ex | n | Z | R¹ | A-B |
|---|---|---|---|---|
| 1301 | 1 | C(O) | H | 4-benzylpiperidine |
| 1302 | 1 | C(O) | H | 3-acetyl-4-benzylpiperidine |
| 1303 | 1 | C(O) | H | 4-(3-fluorobenzyl)piperidine |
| 1304 | 1 | C(O) | H | 4-(4-fluorobenzyl)piperidine |
| 1305 | 1 | C(O) | H | 4-(2,3-difluorobenzyl)piperidine |
| 1306 | 1 | C(O) | H | 4-(2-chloro-4-fluorobenzyl)piperidine |
| 1307 | 1 | C(O) | CH₂CH₂OH | 4-benzylpiperidine |
| 1308 | 1 | C(O) | CH₂CH₂OH | 3-acetyl-4-benzylpiperidine |
| 1309 | 1 | C(O) | CH₂CH₂OH | 4-(3-fluorobenzyl)piperidine |
| 1310 | 1 | C(O) | CH₂CH₂OH | 4-(4-fluorobenzyl)piperidine |
| 1311 | 1 | C(O) | CH₂CH₂OH | 4-(2,3-difluorobenzyl)piperidine |
| 1312 | 1 | C(O) | CH₂CH₂OH | 4-(2-chloro-4-fluorobenzyl)piperidine |

TABLE 19-continued

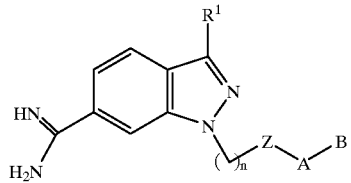

| Ex | n | Z | R¹ | A-B |
|---|---|---|---|---|
| 1313 | 1 | C(O) | CH₂OCH₃ | 4-benzylpiperidine |
| 1314 | 1 | C(O) | CH₂OCH₃ | 3-acetyl-4-benzylpiperidine |
| 1315 | 1 | C(O) | CH₂OCH₃ | 4-(3-fluorobenzyl)piperidine |
| 1316 | 1 | C(O) | CH₂OCH₃ | 4-(4-fluorobenzyl)piperidine |
| 1317 | 1 | C(O) | CH₂OCH₃ | 4-(2,3-difluorobenzyl)piperidine |
| 1318 | 1 | C(O) | CH₂OCH₃ | 4-(2-chloro-4-fluorobenzyl)piperidine |
| 1319 | 1 | C(O) | CH₂CH₂-tetrazolyl | 4-benzylpiperidine |
| 1320 | 1 | C(O) | CH₂CH₂-tetrazolyl | 3-acetyl-4-benzylpiperidine |
| 1321 | 1 | C(O) | CH₂CH₂-tetrazolyl | 4-(3-fluorobenzyl)piperidine |
| 1322 | 1 | C(O) | CH₂CH₂-tetrazolyl | 4-(4-fluorobenzyl)piperidine |
| 1323 | 1 | C(O) | CH₂CH₂-tetrazolyl | 4-(2,3-difluorobenzyl)piperidine |
| 1324 | 1 | C(O) | CH₂CH₂-tetrazolyl | 4-(2-chloro-4-fluorobenzyl)piperidine |
| 1325 | 1 | C(O)NH | H | 4-benzylpiperidine |
| 1326 | 1 | C(O)NH | H | 3-acetyl-4-benzylpiperidine |
| 1327 | 1 | C(O)NH | H | 4-(3-fluorobenzyl)piperidine |
| 1328 | 1 | C(O)NH | H | 4-(4-fluorobenzyl)piperidine |
| i329 | 1 | C(O)NH | H | 4-(2,3-difluorobenzyl)piperidine |
| 1330 | 1 | C(O)NH | H | 4-(2-chloro-4-fluorobenzyl)piperidine |
| 1331 | 1 | C(O)NH | CH₂CH₂OH | 4-benzylpiperidine |
| 1332 | 1 | C(O)NH | CH₂CH₂OH | 3-acetyl-4-benzylpiperidine |
| 1333 | 1 | C(O)NH | CH₂CH₂OH | 4-(3-fluorobenzyl)piperidine |
| 1334 | 1 | C(O)NH | CH₂CH₂OH | 4-(4-fluorobenzyl)piperidine |
| 1335 | 1 | C(O)NH | CH₂CH₂OH | 4-(2,3-difluorobenzyl)piperidine |
| 1336 | 1 | C(O)NH | CH₂CH₂OH | 4-(2-chloro-4-fluorobenzyl)piperidine |
| 1337 | 1 | C(O)NH | CH₂OCH₃ | 4-benzylpiperidine |
| 1338 | 1 | C(O)NH | CH₂OCH₃ | 3-acetyl-4-benzylpiperidine |
| 1339 | 1 | C(O)NH | CH₂OCH₃ | 4-(3-fluorobenzyl)piperidine |
| 1340 | 1 | C(O)NH | CH₂OCH₃ | 4-(4-fluorobenzyl)piperidine |
| 1341 | 1 | C(O)NH | CH₂OCH₃ | 4-(2,3-difluorobenzyl)piperidine |
| 1342 | 1 | C(O)NH | CH₂OCH₃ | 4-(2-chloro-4-fluorobenzyl)piperidine |
| 1343 | 1 | C(O)NH | CH₂CH₂-tetrazolyl | 4-benzylpiperidine |
| 1344 | 1 | C(O)NH | CH₂CH₂-tetrazolyl | 3-acetyl-4-benzylpiperidine |
| 1345 | 1 | C(O)NH | CH₂CH₂-tetrazolyl | 4-(3-fluorobenzyl)piperidine |
| 1346 | 1 | C(O)NH | CH₂CH₂-tetrazolyl | 4-(4-fluorobenzyl)piperidine |
| 1347 | 1 | C(O)NH | CH₂CH₂-tetrazolyl | 4-(2,3-difluorobenzyl)piperidine |
| 1348 | 1 | C(O)NH | CH₂CH₂-tetrazolyl | 4-(2-chloro-4-fluorobenzyl)piperidine |
| 1349 | 1 | SO₂NH | H | 4-benzylpiperidine |
| 1350 | 1 | SO₂NH | H | 3-acetyl-4-benzylpiperidine |
| 1351 | 1 | SO₂NH | H | 4-(3-fluorobenzyl)piperidine |
| 1352 | 1 | SO₂NH | H | 4-(4-fluorobenzyl)piperidine |
| 1353 | 1 | SO₂NH | H | 4-(2,3-difluorobenzyl)piperidine |
| 1354 | 1 | SO₂NH | H | 4-(2-chloro-4-fluorobenzyl)piperidine |
| 1355 | 1 | SO₂NH | CH₂CH₂OH | 4-benzylpiperidine |
| 1356 | 1 | SO₂NH | CH₂CH₂OH | 3-acetyl-4-benzylpiperidine |

TABLE 19-continued

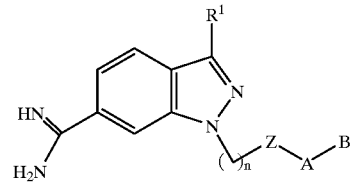

| Ex | n | Z | R¹ | A-B |
|---|---|---|---|---|
| 1357 | 1 | SO₂NH | CH₂CH₂OH | 4-(3-fluorobenzyl)piperidine |
| 1358 | 1 | SO₂NH | CH₂CH₂OH | 4-(4-fluorobenzyl)piperidine |
| 1359 | 1 | SO₂NH | CH₂CH₂OH | 4-(2,3-difluorobenzyl)piperidine |
| 1360 | 1 | SO₂NH | CH₂CH₂OH | 4-(2-chloro-4-fluorobenzyl)piperidine |
| 1361 | 1 | SO₂NH | CH₂OCH₃ | 4-benzylpiperidine |
| 1362 | 1 | SO₂NH | CH₂OCH₃ | 3-acetyl-4-benzylpiperidine |
| 1363 | 1 | SO₂NH | CH₂OCH₃ | 4-(3-fluorobenzyl)piperidine |
| 1364 | 1 | SO₂NH | CH₂OCH₃ | 4-(4-fluorobenzyl)piperidine |
| 1365 | 1 | SO₂NH | CH₂OCH₃ | 4-(2,3-difluorobenzyl)piperidine |
| 1366 | 1 | SO₂NH | CH₂OCH₃ | 4-(2-chloro-4-fluorobenzyl)piperidine |
| 1367 | 1 | SO₂NH | CH₂CH₂-tetrazolyl | 4-benzylpiperidine |
| 1368 | 1 | SO₂NH | CH₂CH₂-tetrazolyl | 3-acetyl-4-benzylpiperidine |
| 1369 | 1 | SO₂NH | CH₂CH₂-tetrazolyl | 4-(3-fluorobenzyl)piperidine |
| 1370 | 1 | SO₂NH | CH₂CH₂-tetrazolyl | 4-(4-fluorobenzyl)piperidine |
| 1371 | 1 | SO₂NH | CH₂CH₂-tetrazolyl | 4-(2,3-difluorobenzyl)piperidine |
| 1372 | 1 | SO₂NH | CH₂CH₂-tetrazolyl | 4-(2-chloro-4-fluorobenzyl)piperidine |

TABLE 20

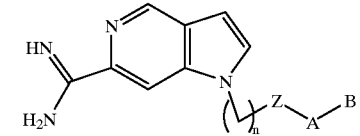

| Ex | n | Z | A-B |
|---|---|---|---|
| 1401 | 1 | C(O) | 4-(2-aminosulfonylphenyl)phenyl |
| 1402 | 1 | C(O) | 4-(2-aminosulfonylphenyl)-2-pyridyl |
| 1403 | 1 | C(O) | 4-(2-methylaminosulfonyl-phenyl)phenyl |
| 1404 | 1 | C(O) | 4-(2-ethylaminosulfonyl-phenyl)-2-pyridyl |
| 1405 | 1 | C(O) | 2-aminosulfonyl-4-cyclohexylphenyl |
| 1406 | 1 | C(O) | 3-aminosulfonyl-4-t-butyl-2-pyridyl |
| 1407 | 1 | C(O) | 2-(5-indazol-5-yl)furanyl |
| 1408 | 1 | C(O) | 2-(5-indazol-6-yl)thienyl |
| 1409 | 1 | C(O) | 4-(2-tetrazolylphenyl)phenyl |
| 1410 | 1 | C(O)NH | 4-(2-aminosulfonylphenyl)phenyl |
| 1411 | 1 | C(O)NH | 4-(2-aminosulfonylphenyl)-2-pyridyl |
| 1412 | 1 | C(O)NH | 4-(2-methylaminosulfonyl-phenyl)phenyl |
| 1413 | 1 | C(O)NH | 4-(2-ethylaminosulfonyl-phenyl)-2-pyridyl |
| 1414 | 1 | C(O)NH | 2-aminosulfonyl-4-cyclohexylphenyl |

TABLE 20-continued

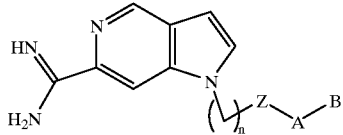

| Ex | n | Z | A-B |
|---|---|---|---|
| 1415 | 1 | C(O)NH | 3-aminosulfonyl-4-t-butyl-2-pyridyl |
| 1416 | 1 | C(O)NH | 2-(5-indazol-5-yl)furanyl |
| 1417 | 1 | C(O)NH | 2-(5-indazol-6-yl)thienyl |
| 1418 | 1 | C(O)NH | 4-(2-tetrazolylphenyl)phenyl |
| 1419 | 1 | NHC(O) | 4-(2-aminosulfonylphenyl)phenyl |
| 1420 | 1 | NHC(O) | 4-(2-aminosulfonylphenyl)-2-pyridyl |
| 1421 | 1 | NHC(O) | 4-(2-methylaminosulfonyl-phenyl)phenyl |
| 1422 | 1 | NHC(O) | 4-(2-ethylaminosulfonyl-phenyl)-2-pyridyl |
| 1423 | 1 | NHC(O) | 2-aminosulfonyl-4-cyclohexylphenyl |
| 1424 | 1 | NHC(O) | 3-aminosulfonyl-4-t-butyl-2-pyridyl |
| 1425 | 1 | NHC(O) | 2-(5-indazol-5-yl)furanyl |
| 1426 | 1 | NHC(O) | 2-(5-indazol-6-yl)thienyl |
| 1427 | 1 | NHC(O) | 4-(2-tetrazolylphenyl)phenyl |
| 1428 | 1 | SO$_2$NH | 4-(2-aminosulfonylphenyl)phenyl |
| 1429 | 1 | SO$_2$NH | 4-(2-aminosulfonylphenyl)-2-pyridyl |
| 1430 | 1 | SO$_2$NH | 4-(2-methylaminosulfonyl-phenyl)phenyl |
| 1431 | 1 | SO$_2$NH | 4-(2-ethylaminosulfonyl-phenyl)-2-pyridyl |
| 1432 | 1 | SO$_2$NH | 2-aminosulfonyl-4-cyclohexylphenyl |
| 1433 | 1 | SO$_2$NH | 3-aminosulfonyl-4-t-butyl-2-pyridyl |
| 1434 | 1 | SO$_2$NH | 2-(5-indazol-5-yl)furanyl |
| 1435 | 1 | SO$_2$NH | 2-(5-indazol-6-yl)thienyl |
| 1436 | 1 | SO$_2$NH | 4-(2-tetrazolylphenyl)phenyl |
| 1437 | 0 | CH(CH$_2$CH$_2$OH)C(O)NH | 4-(2-aminosulfonylphenyl)phenyl |
| 1438 | 0 | CH(CH$_2$CH$_2$OH)C(O)NH | 4-(2-aminosulfonylphenyl)-2-pyridyl |
| 1439 | 0 | CH(CH$_2$CH$_2$OH)C(O)NH | 4-(2-methylaminosulfonyl-phenyl)phenyl |
| 1440 | 0 | CH(CH$_2$CH$_2$OH)C(O)NH | 4-(2-ethylaminosulfonyl-phenyl)-2-pyridyl |
| 1441 | 0 | CH(CH$_2$CH$_2$OH)C(O)NH | 2-aminosulfonyl-4-cyclohexylphenyl |
| 1442 | 0 | CH(CH$_2$CH$_2$OH)C(O)NH | 3-aminosulfonyl-4-t-butyl-2-pyridyl |
| 1443 | 0 | CH(CH$_2$CH$_2$OH)C(O)NH | 2-(5-indazol-5-yl)furanyl |
| 1444 | 0 | CH(CH$_2$CH$_2$OH)C(O)NH | 2-(5-indazol-6-yl)thienyl |
| 1445 | 0 | CH(CH$_2$CH$_2$OH)C(O)NH | 4-(2-tetrazolylphenyl)phenyl |
| 1446 | 0 | CH(CH$_2$-tetrazolyl)C(O)NH | 4-(2-aminosulfonylphenyl)phenyl |
| 1447 | 0 | CH(CH$_2$-tetrazolyl)C(O)NH | 4-(2-aminosulfonylphenyl)-2-pyridyl |
| 1448 | 0 | CH(CH$_2$-tetrazolyl)C(O)NH | 4-(2-methylaminosulfonyl-phenyl)phenyl |
| 1449 | 0 | CH(CH$_2$-tetrazolyl)C(O)NH | 4-(2-ethylaminosulfonyl-phenyl)-2-pyridyl |
| 1450 | 0 | CH(CH$_2$-tetrazolyl)C(O)NH | 2-aminosulfonyl-4-cyclohexylphenyl |
| 1451 | 0 | CH(CH$_2$-tetrazolyl)C(O) NH | 3-aminosulfonyl-4-t-butyl-2-pyridyl |

TABLE 20-continued

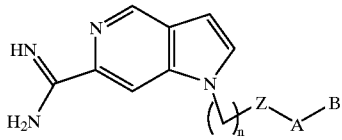

| Ex | n | Z | A-B |
|---|---|---|---|
| 1452 | 0 | CH(CH$_2$-tetrazolyl)C(O)NH | 2-(5-indazol-5-yl)furanyl |
| 1453 | 0 | CH(CH$_2$-tetrazolyl)C(O)NH | 2-(5-indazol-6-yl)thienyl |
| 1454 | 0 | CH(CH$_2$-tetrazolyl)C(O)NH | 4-(2-tetrazolylphenyl)phenyl |

TABLE 21

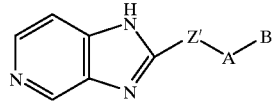

| Ex | Z' | A-B |
|---|---|---|
| 1501 | CH$_2$C(O)NH | 4-(2-aminosulfonylphenyl)phenyl |
| 1502 | CH$_2$C(O)NH | 4-(2-aminosulfonylphenyl)-2-pyridyl |
| 1503 | CH$_2$C(O)NH | 4-(2-methylaminosulfonyl-phenyl)phenyl |
| 1504 | CH$_2$C(O)NH | 4-(2-ethylaminosulfonyl-phenyl)-2-pyridyl |
| 1505 | CH$_2$C(O)NH | 2-aminosulfonyl-4-cyclohexylphenyl |
| 1506 | CH$_2$C(O)NH | 3-aminosulfonyl-4-t-butyl-2-pyridyl |
| 1507 | CH$_2$C(O)NH | 2-(5-indazol-5-yl)furanyl |
| 1508 | CH$_2$C(O)NH | 2-(5-indazol-6-yl)thienyl |
| 1509 | CH$_2$C(O)NH | 4-(2-tetrazolylphenyl)phenyl |
| 1510 | CH$_2$CH$_2$C(O)NH | 4-(2-aminosulfonylphenyl)phenyl |
| 1511 | CH$_2$CH$_2$C(O)NH | 4-(2-aminosulfonylphenyl)-2-pyridyl |
| 1512 | CH$_2$CH$_2$C(O)NH | 4-(2-tert-butylaminosulfonyl-phenyl)phenyl |
| 1513 | CH$_2$CH$_2$C(O)NH | 4-(2-ethylaminosulfonyl-phenyl)-2-pyridyl |
| 1514 | CH$_2$CH$_2$C(O)NH | 2-aminosulfonyl-4-cyclohexylphenyl |
| 1515 | CH$_2$CH$_2$C(O)NH | 3-aminosulfonyl-4-t-butyl-2-pyridyl |
| 1516 | CH$_2$CH$_2$C(O)NH | 2-(5-indazol-5-yl)furanyl |
| 1517 | CH$_2$CH$_2$C(O)NH | 2-(5-indazol-6-yl)thienyl |
| 1518 | CH$_2$CH$_2$C(O)NH | 4-(2-tetrazolylphenyl)phenyl |
| 1519 | SCH$_2$C(O)NH | 4-(2-aminosulfonylphenyl)phenyl |
| 1520 | SCH$_2$C(O)NH | 4-(2-aminosulfonylphenyl)-2-pyridyl |
| 1521 | SCH$_2$C(O)NH | 4-(2-methylaminosulfonyl-phenyl)phenyl |
| 1522 | SCH$_2$C(O)NH | 4-(2-ethylaminosulfonyl-phenyl)-2-pyridyl |
| 1523 | SCH$_2$C(O)NH | 2-aminosulfonyl-4-cyclohexylphenyl |
| 1524 | SCH$_2$C(O)NH | 3-aminosulfonyl-4-t-butyl-2-pyridyl |
| 1525 | SCH$_2$C(O)NH | 2-(5-indazol-5-yl)furanyl |
| 1526 | SCH$_2$C(O)NH | 2-(5-indazol-6-yl) thienyl |
| 1527 | SCH$_2$C(O)NH | 4-(2-tetrazolylphenyl)phenyl |

UTILITY

The compounds of this invention are useful as anticoagulants for the treatment or prevention of thromboembolic disorders in mammals. The term "thromboembolic disorders" as used herein includes arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, cerebral embolism, kidney embolisms, and pulmonary embolisms. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Kabi Pharmacia, Franklin, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o - v_s)/v_s = I/(K_i (1+S/K_m))$$

where:

$v_o$ is the velocity of the control in the absence of inhibitor;

$v_s$ is the velocity in the presence of inhibitor;

I is the concentration of inhibitor;

$K_i$ is the dissociation constant of the enzyme:inhibitor complex;

S is the concentration of substrate;

$K_m$ is the Michaelis constant.

Using the methodology described above, a number of compounds of the present invention were found to exhibit a $K_i$ of ≦5 μm, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing which contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose which produces 50% inhibition of thrombus formation) are estimated by linear regression.

The compounds of formula (I) are also considered to be useful as inhibitors of serine proteases, notably human thrombin, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm which arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 5 μm, thereby confirming the utility of the compounds of the invention as effective thrombin inhibitors.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin, as well as other factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include IIb/IIIa antagonists, thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471,651 A2, the disclosures of which are hereby incorporated herein by reference.

The term thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but no compound of the present invention, then one would conclude factor Xa was present.

DOSAGE AND FORMULATION

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences,* Mack Publishing Company, a standard reference text in this field.

Representative useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of Formula I are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

What is claimed as new and desired to be secured by Letter Patent of United States is:

1. A compound of formula I:

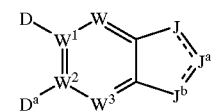

or stereoisomer or pharmaceutically acceptable salt form thereof wherein:

W and $W^3$ are CH;

$W^1$ and $W^2$ are selected from C and CH;

one of D and $D^a$ is selected from CN, $C(=NR^7)NR^8R^9$, $NHC(=NR^7)NR^8R^9$, $NR^8CH(=NR^7)$, $C(O)NR^8R^9$, and $(CH_2)_rNR^8R^9$, and the other is absent;

one of $J^a$ and $J^b$ is substituted by $-(CH_2)_n-Z-A-B$;

J, $J^a$, and $J^b$ combine to form pyrazole substituted with 0–2 $R^1$;

$R^1$ is selected from H, $C_{1-4}$ alkyl, $(CH_2)_rOR^3$, $(CH_2)_r NR^3R^3{}'$, $(CH_2)_rC(=O)R^2$, $(CH_2)_r(CH=CH)(CH_2)_rC(=O)R^2$, $(CH_2)_rNR^3C(O)R^2$, $(CH_2)_rSO_2R^4$, $(CH_2)_rR^3SO_2R^4$, and $(CH_2)_r$-5-membered heterocyclic group having 1–4 heteroatoms selected from N, O, and S;

$R^2$ is selected from H, $OR^3$, $C_{1-4}$ alkyl, $NR^3R^3{}'$, $CF_3$, and $C_{3-10}$ carbocyclic group substituted with 0–2 $R^6$;

$R^3$ and $R^3{}'$ are independently selected from H, $C_{1-4}$ alkyl, and $C_{3-10}$ carbocyclic group substituted with 0–2 $R^6$;

$R^4$ is selected from $C_{1-4}$ alkyl, $NR^3R^3{}'$, and $C_{3-10}$ carbocyclic group substituted with 0–2 $R^6$;

Z is selected from CH=CH, $CH((CH_2)_mQ(CH_2)_mR^5)$, $CH((CH_2)_mQ(CH_2)_mR^5)C(O)NR^3$, $CH((CH_2)_mC(O)(CH_2)_mR^{5a})$, $N((CH_2)_qQ(CH_2)_mR^5)$, $N(Q'(CH_2)_mR^5)$, $C(O)N((CH_2)_mQ'(CH_2)_mR^{5a})$, $C(O)(CH_2)_r$, $C(O)O(CH_2)_r$, $OC(O)(CH_2)_r$, $C(O)(CH_2)_rNR^3(CH_2)_r$, $NR^3C(O)(CH_2)_r$, $OC(O)NR^3(CH_2)_r$, $NR^3C(O)O(CH_2)_r$, $NR^3C(O)NR^3(CH_2)_r$, $S(O)_p(CH_2)_r$, $SO_2CH_2$, $SCH_2C(O)NR^3$, $SO_2NR^3(CH_2)_r$, $NR^3SO_2(CH_2)_r$, and $NR^3SO_2NR^3(CH_2)_r$;

Q is selected from a bond, O, $NR^3$, C(O), $C(O)NR^3$, $NR^3C(O)$, $SO_2$, $NR^3SO_2$, and $SO_2NR^3$;

Q' is selected from a bond, C(O), $C(O)NR^3$, $SO_2$, and $SO_2NR^3$;

$R^5$ is selected from H, $C_{1-4}$ alkyl, $C_{3-10}$ carbocyclic group substituted with 0–2 $R^6$, and 5–10 membered heterocyclic group containing from 1–3 heteroatoms selected from the group consisting of N, O, and S substituted with 0–2 $R^6$, provided that when Q is $SO_2$ or $NR^3SO_2$, $R^5$ is other than H and when Q' is $SO_2$, $R^5$ is other than H;

$R^{5a}$ is selected from $NHR^5$, $OR^5$, and $R^5$;

A is pyridine substituted with 0–2 $R^6$;

B is selected from:
X—Y, $C_{3-6}$ alkyl, $NR^3R^3{}'$, $C(=NR^3)NR^3R^3{}'$, $NR^3C(=NR^3)NR^3R^3{}'$,
benzyl substituted with 0–2 $R^6$,
$C_{3-10}$ carbocyclic group substituted with 0–2 $R^6$, and
5–10 membered heterocyclic group containing from 1–3 heteroatoms selected from the group consisting of N, O, and S substituted with 0–2 $R^6$;

X is selected from $C_{1-4}$ alkylene, —C(O)—, —C(O)$CR^3R^3{}'$—, —$CR^3R^3{}'$C(O), —S(O)$_p$—, —S(O)

87

$_pCR^3R^{3'}$—, —$CR^3R^{3'}S(O)_p$—, —$S(O)_2NR^3$—, —$NR^3S(O)_2$—, —$C(O)NR^3$—, —$NR^3C(O)$—, —$NR^3$—, —$NR^3CR^3R^{3'}$—, —$CR^3R^{3'}NR^3$—, O, —$CR^3R^{3'}O$—, and —$OCR^3R^{3'}$—;

Y is selected from:
  $C_{3-10}$ carbocyclic group substituted with 0–2 $R^6$, and
  5–10 membered heterocyclic group containing from 1–3 heteroatoms selected from the group consisting of N, O, and S substituted with 0–2 $R^6$;

$R^6$ is selected from H, OH, $(CH_2)_nOR^3$, halo, $C_{1-4}$ alkyl, CN, $NO_2$, $(CH_2)_rNR^3R^{3'}$, $(CH_2)_rC(O)R^3$, $NR^3C(O)R^{3'}$, $NR^3C(O)NR^3R^{3'}$, $CH(=NH)NH_2$, $NHC(=NH)NH_2$, $SO_2NR^3R^{3'}$, $CONHSO_2R^4$, $NR^3SO_2NR^3R^{3'}$, $NR^3SO_2$—$C_{1-4}$ alkyl, and ($C_{1-4}$ alkyl)-tetrazolyl;

$R^7$ is selected from H, OH, $C_{1-6}$ alkyl, $C_{1-6}$ alkylcarbonyl, $C_{1-6}$ alkoxy, $C_{1-4}$ alkoxycarbonyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$ is selected from H, $C_{1-6}$ alkyl and $(CH_2)_n$-phenyl;

$R^9$ is selected from H, $C_{1-6}$ alkyl and $(CH_2)_n$-phenyl;

n is selected from 0, 1, 2, 3, and 4;

m is selected from 0, 1, and 2;

p is selected from 0, 1, and 2;

q is selected from 1 and 2; and, r is selected from 0, 1, 2, 3, and 4;

provided that:
  (a) Z is other than $CH_2$; and,
  (b) if Z is $CH((CH_2)_mQ(CH_2)_mR^5)$ or $CH((CH_2)_mC(O)(CH_2)_mR^{5a})$, then B is other than X—Y, a $C_{3-10}$ carbocyclic group or a 5–10 membered heterocyclic group;
  (c) $R^5$, B, and Y are other than piperazine and piperidine.

2. A compound according to claim 1, wherein the compound is of formula II:

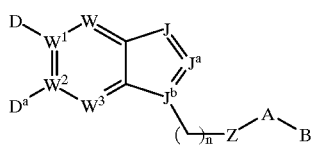

II or a stereoisomer or pharmaceutically acceptable salt, wherein:

$R^1$ is selected from H, $C_{1-4}$ alkyl, $(CH_2)_rOR^3$, $(CH_2)_rNR^3R^{3'}$, $(CH_2)_rC(=O)R^2$, $(CH_2)_rNR^3C(=O)R^2$, $(CH_2)_rSO_2R^4$, $(CH_2)_rNR^3SO_2R^4$, and $(CH_2)_r$-5-membered heterocyclic group having 1–4 heteroatoms selected from N, O, and S;

$R^2$ is selected from H, $OR^3$, $C_{1-4}$ alkyl, $NR^3R^{3'}$, and $CF_3$;

$R^3$ and $R^{3'}$ are independently selected from H, $C_{1-4}$ alkyl, and phenyl;

$R^4$ is selected from $C_{1-4}$ alkyl, phenyl and $NR^3R^{3'}$;

Z is selected from CH=CH, $CH((CH_2)_mQ(CH_2)_mR^5)$, $CH((CH_2)_mQ(CH_2)_mR^5)C(O)NR^3$, $CH((CH_2)_mC(O)(CH_2)_mR^{5a})$, $N((CH_2)_qQ(CH_2)_mR^5)$, $N(Q'(CH_2)_mR^5)$, $C(O)N((CH_2)_mQ'(CH_2)_mR^{5a})$, C(O), $C(O)CH_2$, C(O)O, OC(O), $C(O)(CH_2)_rNR^3(CH_2)_r$, $NR^3C(O)$, OC(O)$NR^3$, $NR^3C(O)O$, $NR^3C(O)NR^3$, $S(O)_p$, $SO_2CH_2$, $SO_2NR^3$, $NR^3SO_2$, and $NR^3SO_2NR^3$;

88

B is selected from:
  X—Y, $C_{3-6}$ alkyl,
  benzyl substituted with 0–2 $R^6$,
  $C_{3-10}$ carbocyclic group substituted with 0–2 $R^6$, and
  5–10 membered heterocyclic group containing from 1–3 heteroatoms selected from the group consisting of N, O, and S substituted with 0–2 $R^6$; and, $R^6$ is selected from H, OH, $(CH_2)_nOR^3$, halo, $C_{1-4}$ alkyl, CN, $NO_2$, $(CH_2)_rNR^3R^{3'}$, $(CH_2)_rC(O)R^3$, $NR^3C(O)R^{3'}$, $NR^3C(O)NR^3R^{3'}$, $SO_2NR^3R^{3'}$, $CONHSO_2R^4$, $NR^3SO_2NR^3R^{3'}$, $NR^3SO_2$—$C_{1-4}$ alkyl and ($C_{1-4}$ alkyl)-tetrazolyl.

3. A compound according to claim 2, wherein:

$R^1$ is selected from H, $C_{1-4}$ alkyl, $(CH_2)_rOR^3$, $(CH_2)_rNR^3R^{3'}$, $(CH_2)_rC(=O)R^2$, $(CH_2)_rNR^3C(=O)R^2$, $(CH_2)_rSO_2R^4$, and $(CH_2)_rNR^3SO_2R^4$;

Z is selected from $CH((CH_2)_mQ(CH_2)_mR^5)$, $CH((CH_2)_m(CH_2)_mR^5)C(O)NR^3$, $CH((CH_2)_mC(O)(CH_2)_mR^{5a})$, $N((CH_2)_qQ(CH_2)_mR^5)$, $N(Q'(CH_2)_mR^5)$, $C(O)N((CH_2)_m Q'(CH_2)_mR^{5a})$, C(O), $C(O)CH_2$, $C(O)(CH_2)_rNR^3(CH_2)_r$, $NR^3C(O)$, $NR^3C(O)NR^3$, $S(O)_2$, $SO_2CH_2$, $SO_2NR^3$, $NR^3SO_2$, and $NR^3SO_2NR^3$;

B is selected from:
  X—Y, $C_{3-6}$ alkyl,
  benzyl substituted with 0–2 $R^6$,
  $C_{5-6}$ carbocyclic group substituted with 0–2 $R^6$, and
  5–6 membered heterocyclic group containing from 1–3 heteroatoms selected from the group consisting of N, O, and S substituted with 0–2 $R^6$;

X is selected from —C(O)—, —$C(O)CR^3R^{3'}$—, —$S(O)_2$—, —$S(O)_pCR^3R^{3'}$—, —$S(O)_2NR^3$—, —$C(O)NR^3$—, —$NR^3$—, —$NR^3CR^3R^{3'}$—, and O;

Y is selected from:
  $C_{5-6}$ carbocyclic group substituted with 0–2 $R^6$, and
  5–6 membered heterocyclic group containing from 1–3 heteroatoms selected from the group consisting of N, O, and S substituted with 0–2 $R^6$;

$R^6$ is selected from H, OH, $(CH_2)_nOR^3$, halo, $C_{1-4}$ alkyl, CN, $NO_2$, $(CH_2)_rNR^3R^{3'}$, $(CH_2)_rC(O)R^3$, $NR^3C(O)R^{3'}$, $NR^3C(O)NR^3R^{3'}$, $SO_2NR^3R^{3'}$, $CONHSO_2R^4$, $NR^3SO_2NR^3R^{3'}$, $NR^3SO_2$—$C_{1-4}$ alkyl and ($C_{1-4}$ alkyl)-tetrazolyl;

n is selected from 0, 1, and 2; and, r is selected from 0, 1, and 2.

4. A pharmaceutical composition, comprising: a pharmaceutically acceptable carrier and a therapeutically effective amount of a compound according to claim 1 or a pharmaceutically acceptable salt thereof.

5. A pharmaceutical composition, comprising: a pharmaceutically acceptable carrier and a therapeutically effective amount of a compound according to claim 2 or a pharmaceutically acceptable salt thereof.

6. A method for treating or preventing a thromboembolic disorder, comprising: administering to a patient in need thereof a therapeutically effective amount of a compound according to claim 1 or a pharmaceutically acceptable salt thereof.

7. A method for treating a thromboembolic disorder, comprising: administering to a patient in need thereof a therapeutically effective amount of a compound according to claim 2 or a pharmaceutically acceptable salt thereof.

* * * * *